United States Patent
Yoshioka et al.

(10) Patent No.: US 10,736,517 B2
(45) Date of Patent: Aug. 11, 2020

(54) NON-CONTACT BLOOD-PRESSURE MEASURING DEVICE AND NON-CONTACT BLOOD-PRESSURE MEASURING METHOD

(71) Applicant: Panasonic Intellectual Property Management Co., Ltd., Osaka (JP)

(72) Inventors: Mototaka Yoshioka, Osaka (JP); Jun Ozawa, Nara (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 1258 days.

(21) Appl. No.: 14/873,229

(22) Filed: Oct. 2, 2015

(65) Prior Publication Data

US 2016/0100766 A1 Apr. 14, 2016

(30) Foreign Application Priority Data

Oct. 9, 2014 (JP) .................................. 2014-208206

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0064* (2013.01); *A61B 5/0082* (2013.01);
(Continued)

(58) Field of Classification Search
CPC ... A61B 5/0064; A61B 5/0082; A61B 5/0205; A61B 5/02108; A61B 5/022;
(Continued)

(56) References Cited

U.S. PATENT DOCUMENTS 7,128,714 B1* 10/2006 Antonelli ............... A61B 5/021
600/485
2003/0212336 A1* 11/2003 Lee ..................... A61B 5/02416
600/504
(Continued)

FOREIGN PATENT DOCUMENTS

JP 2-003926 U 1/1990
JP 5-329110 12/1993
(Continued)

*Primary Examiner* — Baisakhi Roy
(74) *Attorney, Agent, or Firm* — Wenderoth, Lind & Ponack, LLP

(57) ABSTRACT

A non-contact blood-pressure measuring device includes: an image acquiring section that acquires a skin image obtained by capturing skin of a user; a pulse-wave timing calculating section that calculates, as a pulse-wave timing, time information indicative of a time at which time-varying luminance in the skin image reaches a peak; a millimeter-wave acquiring section that acquires a signal of a radio wave reflected by the user; a heartbeat timing calculating section that calculates, as a heartbeat timing, time information indicative of a time at which a time-varying distance to the user obtained on the basis of the signal of the radio wave acquired by the millimeter-wave acquiring section reaches a peak; and a blood-pressure determining section that determines blood pressure of the user on the basis of a time difference between the pulse-wave timing and the heartbeat timing.

20 Claims, 47 Drawing Sheets

(51) Int. Cl.
*G01S 13/88* (2006.01)
*A61B 5/11* (2006.01)
*A61B 5/05* (2006.01)
*A61B 5/021* (2006.01)
*A61B 5/024* (2006.01)
*A61B 5/022* (2006.01)
*A61B 5/113* (2006.01)

(52) U.S. Cl.
CPC .......... *A61B 5/0507* (2013.01); *A61B 5/1113* (2013.01); *A61B 5/7278* (2013.01); *G01S 13/88* (2013.01); *A61B 5/022* (2013.01); *A61B 5/024* (2013.01); *A61B 5/02108* (2013.01); *A61B 5/11* (2013.01); *A61B 5/113* (2013.01)

(58) Field of Classification Search
CPC .......... A61B 5/0245; A61B 2560/0242; A61B 2562/0219; A61B 5/0022; A61B 5/02007
See application file for complete search history.

(56) References Cited

U.S. PATENT DOCUMENTS

| | | | |
|---|---|---|---|
| 2008/0018456 A1* | 1/2008 | Kato | A61B 5/0002 340/539.12 |
| 2009/0015464 A1 | 1/2009 | Fukuda | |
| 2011/0054328 A1 | 3/2011 | Hyogo et al. | |
| 2011/0216941 A1* | 9/2011 | Saijo | G06K 9/00355 382/103 |
| 2012/0289788 A1* | 11/2012 | Jain | G06F 19/3418 600/301 |
| 2013/0245465 A1 | 9/2013 | Kasama | |
| 2013/0267859 A1* | 10/2013 | Okuda | A61B 5/0245 600/500 |
| 2014/0088378 A1* | 3/2014 | Muzet | A61B 5/02125 600/301 |
| 2016/0058385 A1* | 3/2016 | Ajima | A61B 5/6898 600/485 |
| 2016/0143544 A1* | 5/2016 | Tanaka | A61B 5/0015 600/479 |
| 2016/0317041 A1* | 11/2016 | Porges | A61B 5/7235 |

FOREIGN PATENT DOCUMENTS

| | | |
|---|---|---|
| JP | 2002-288758 | 10/2002 |
| JP | 2011-050438 | 3/2011 |
| JP | 2011-107165 | 6/2011 |
| JP | 2013-192620 | 9/2013 |
| JP | 2014-188237 | 10/2014 |

* cited by examiner

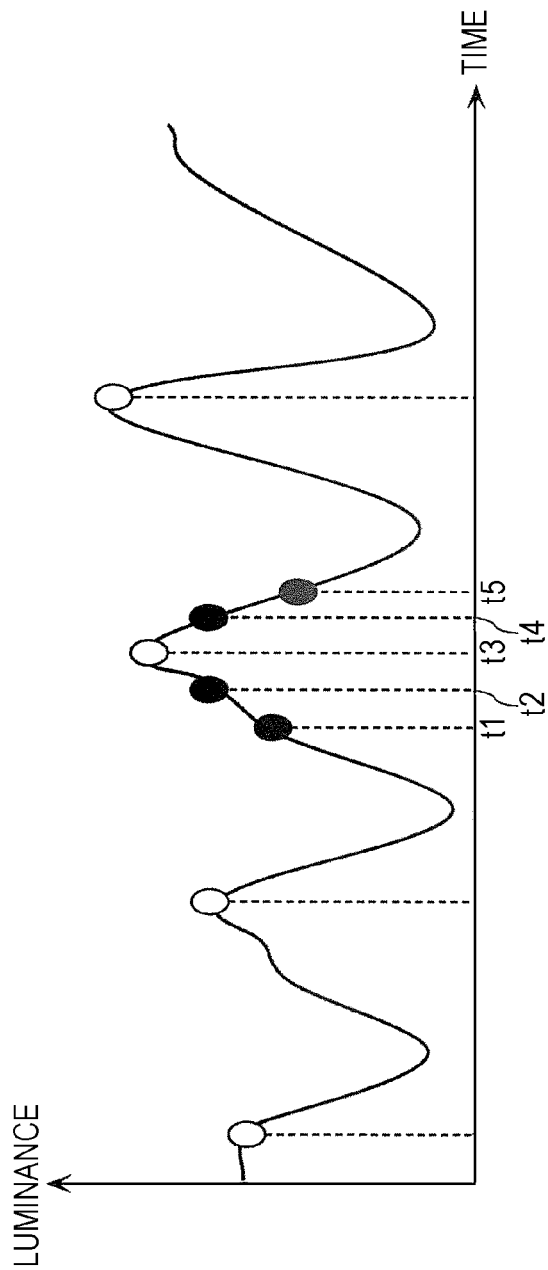

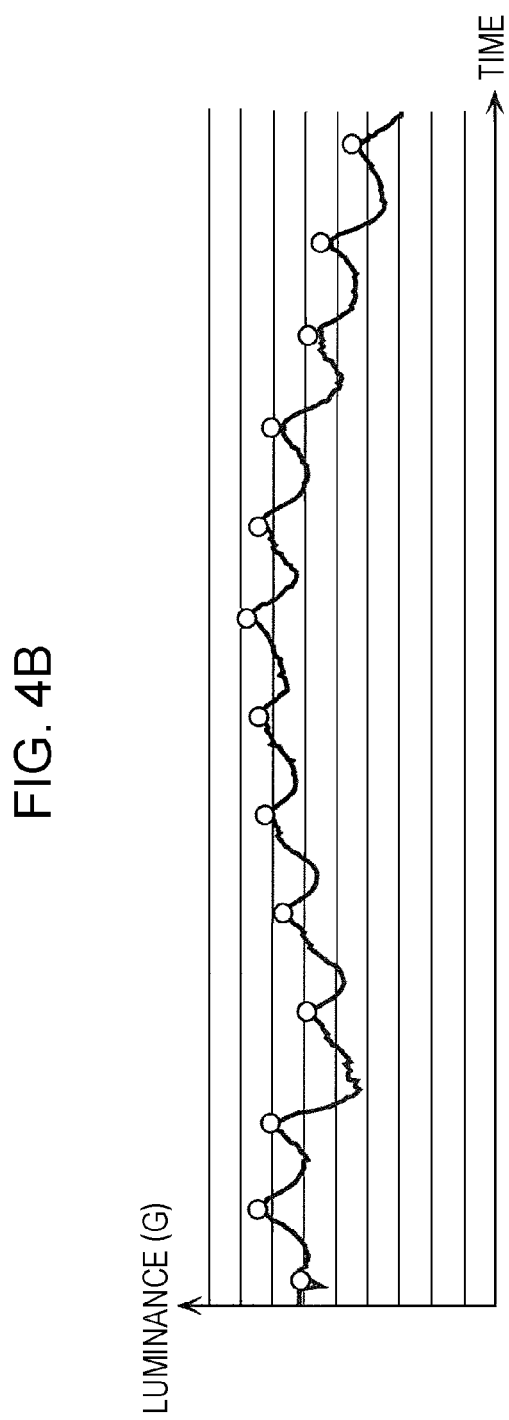

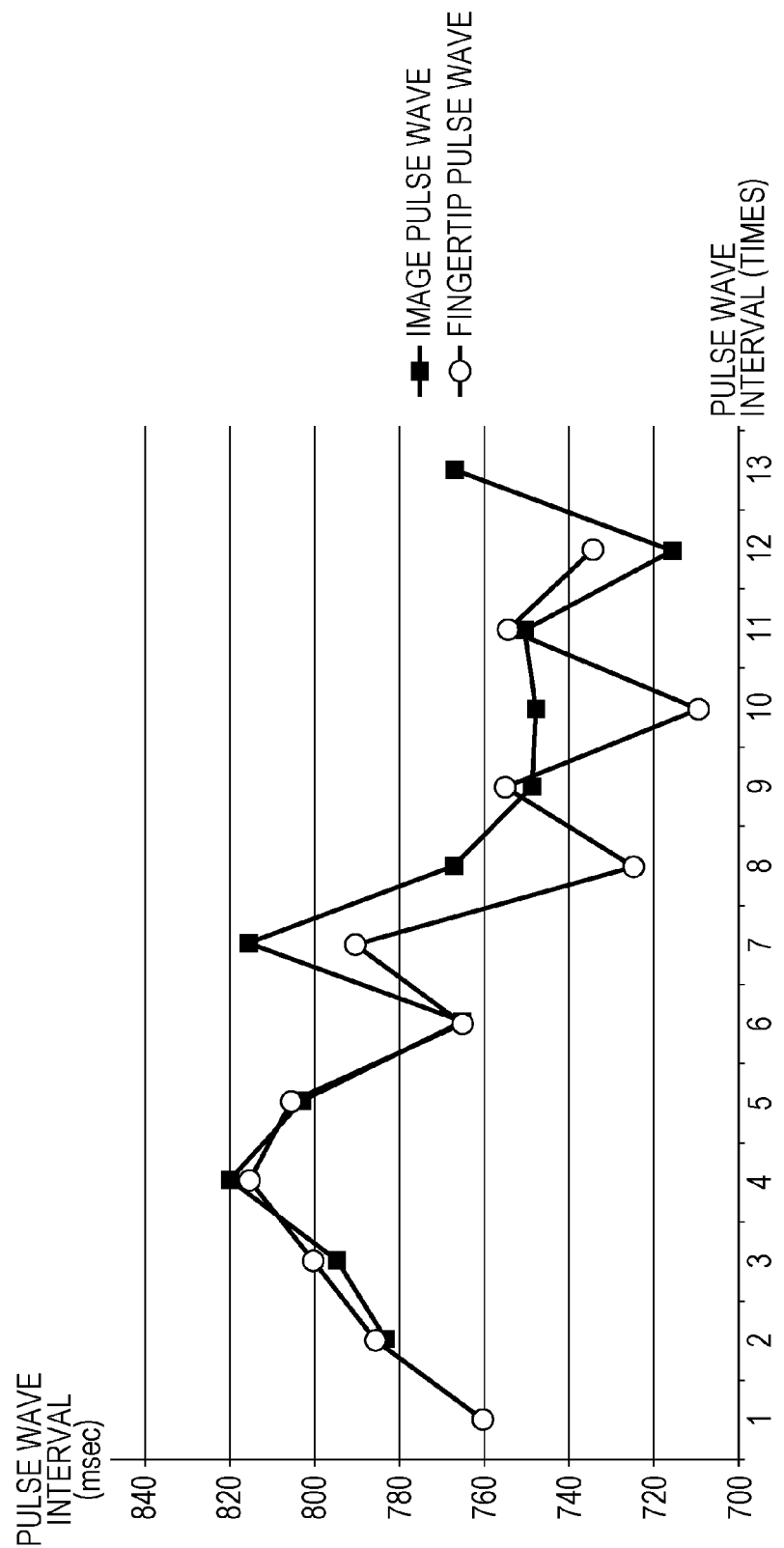

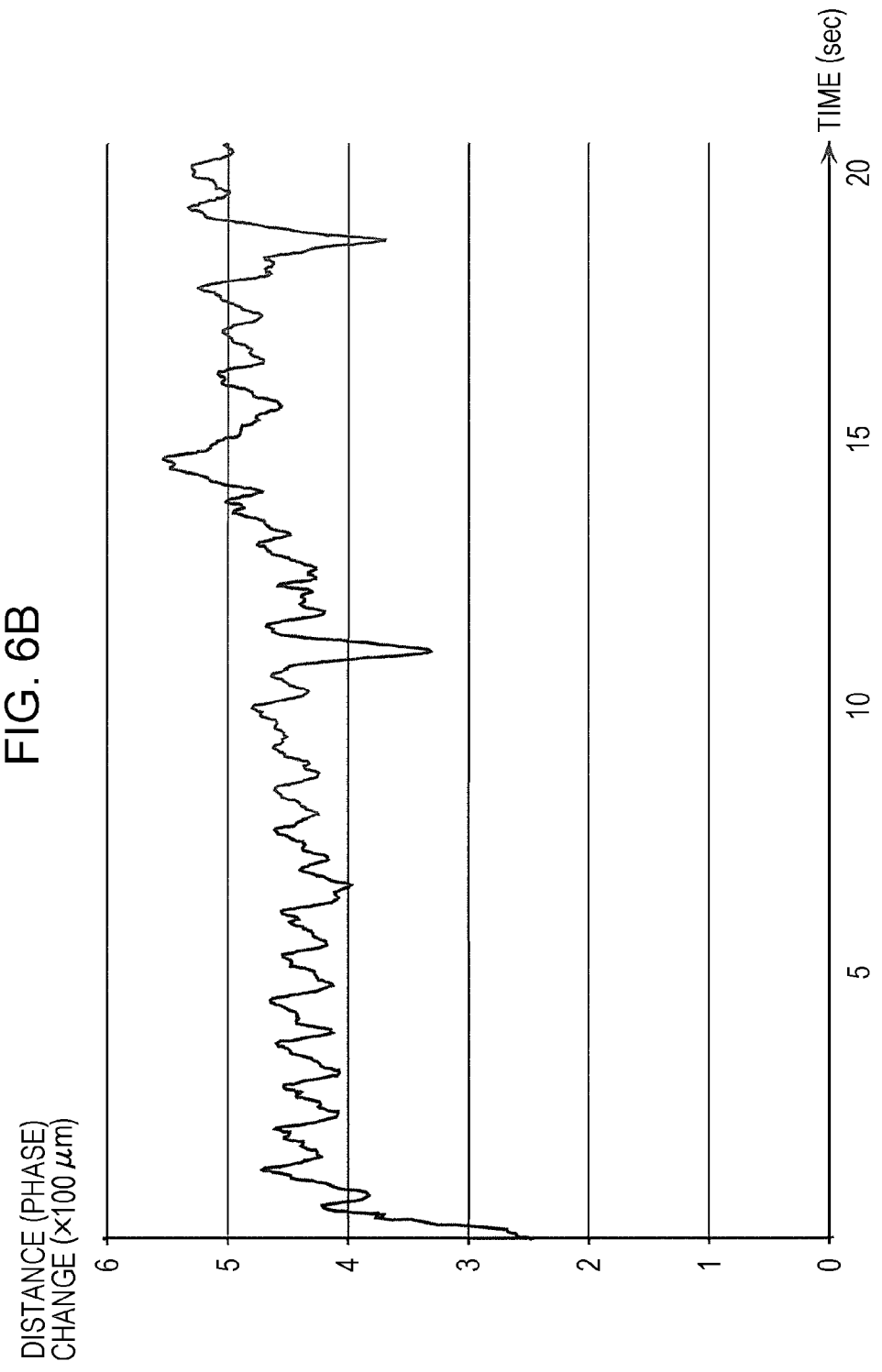

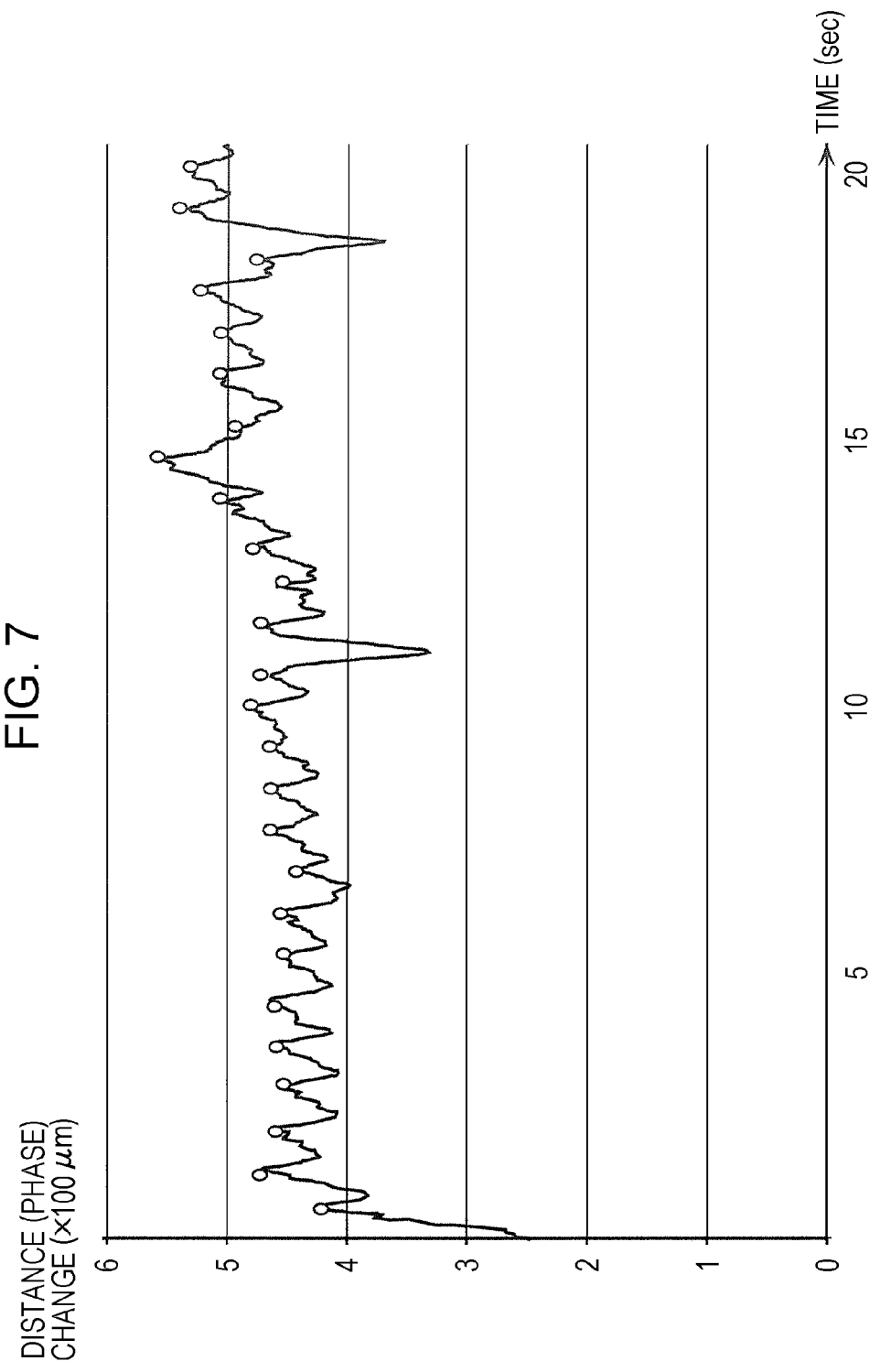

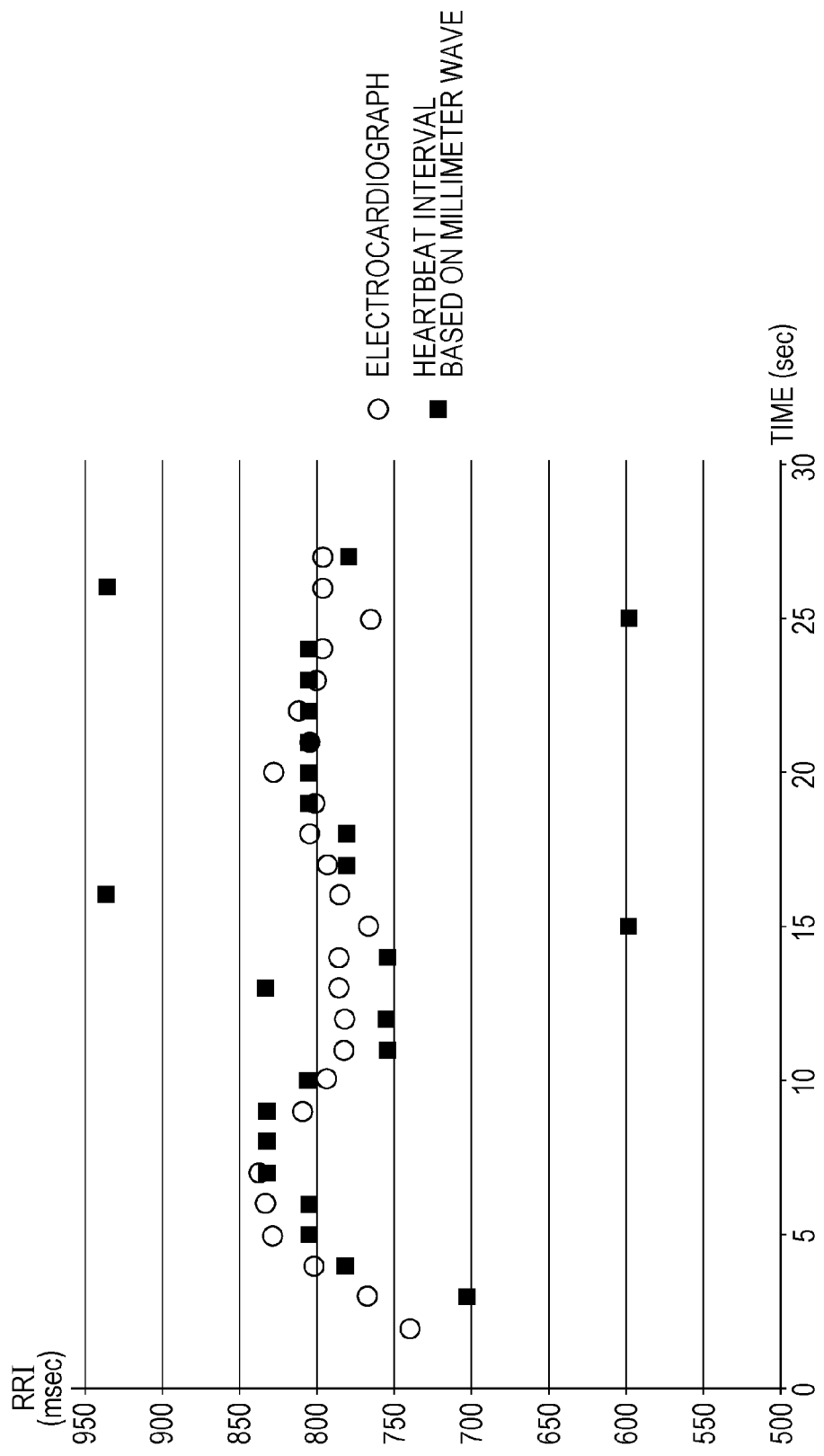

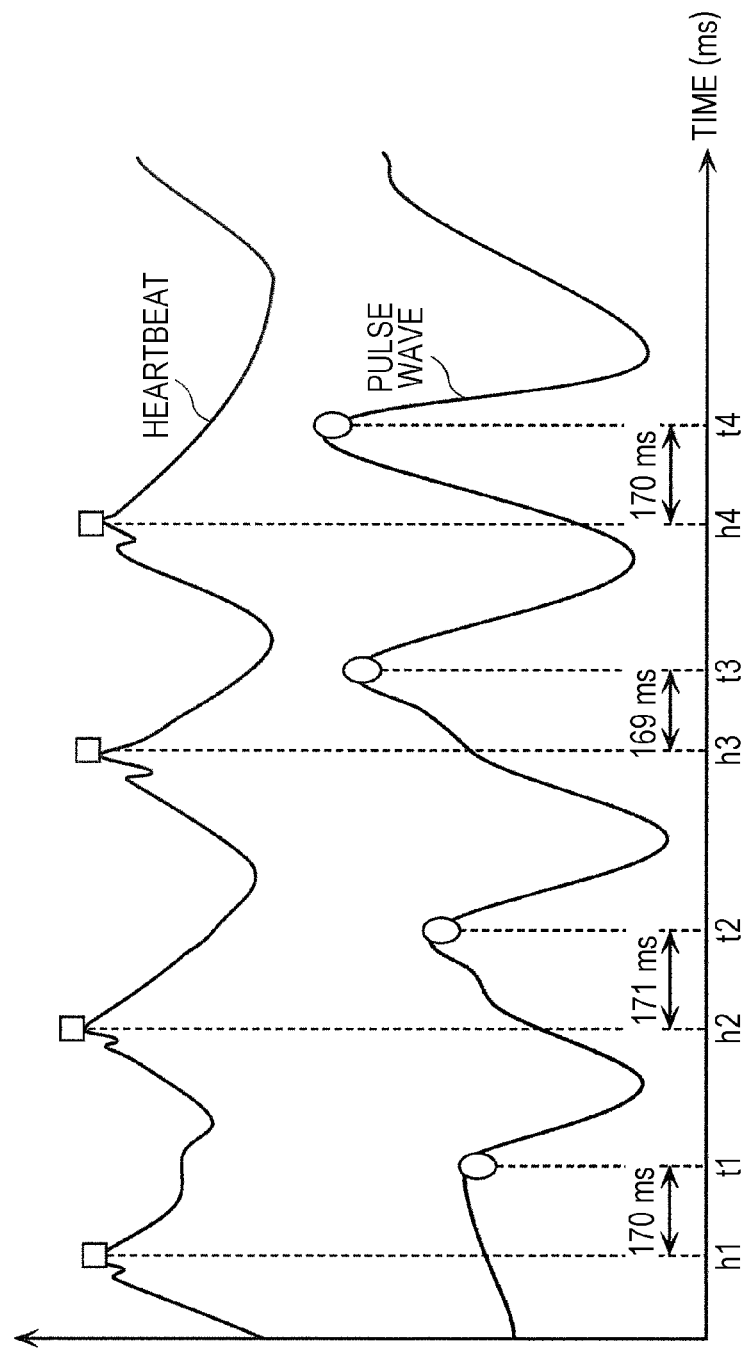

FIG. 15

| USER TYPE | COEFFICIENT α | COEFFICIENT β |
|---|---|---|
| STANDARD (TO 139 mmHg) | −0.8 | 250 |
| HIGH BLOOD PRESSURE (140 mmHg TO 159 mmHg) | −0.9 | 280 |
| . . | . . | . . |

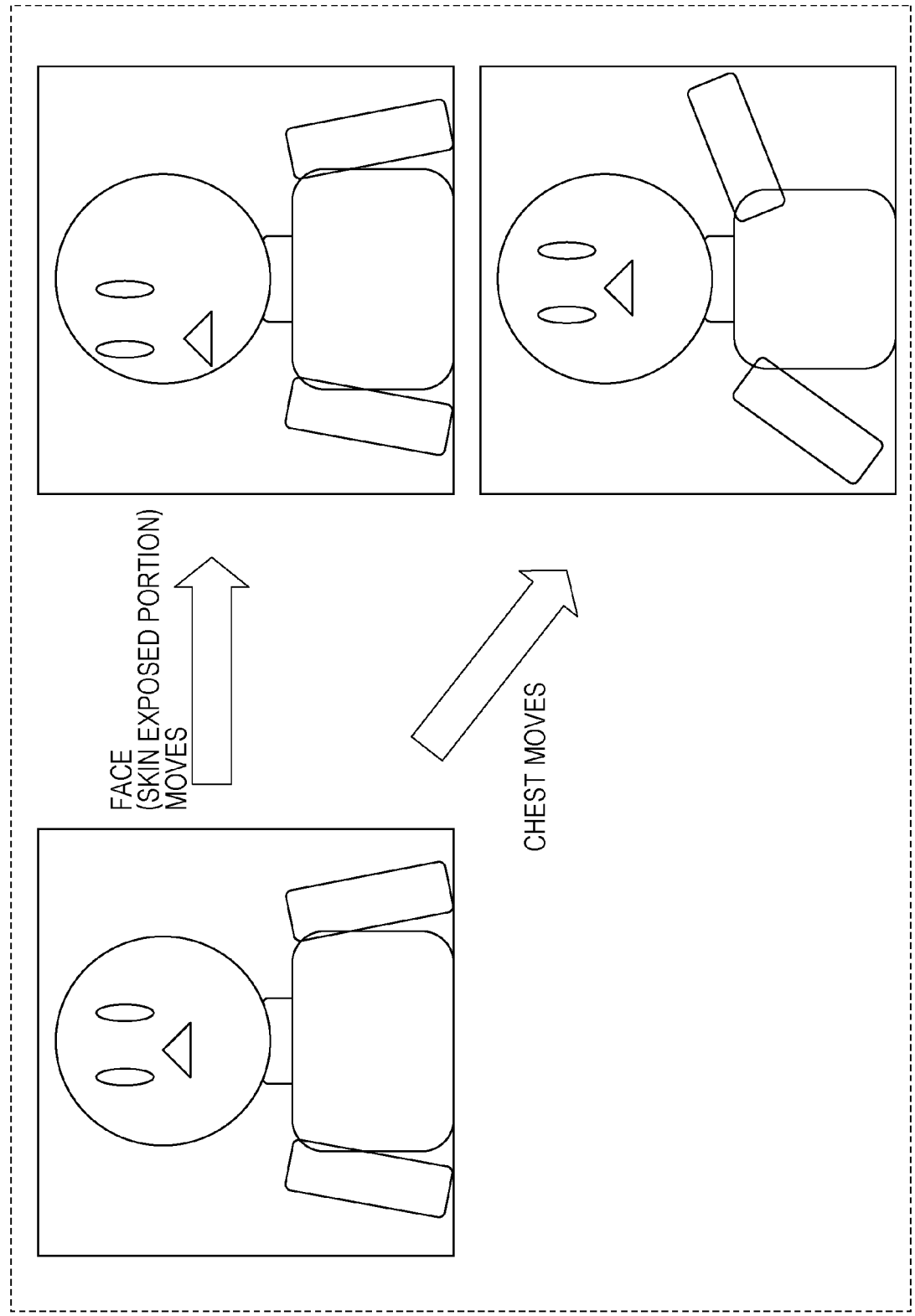

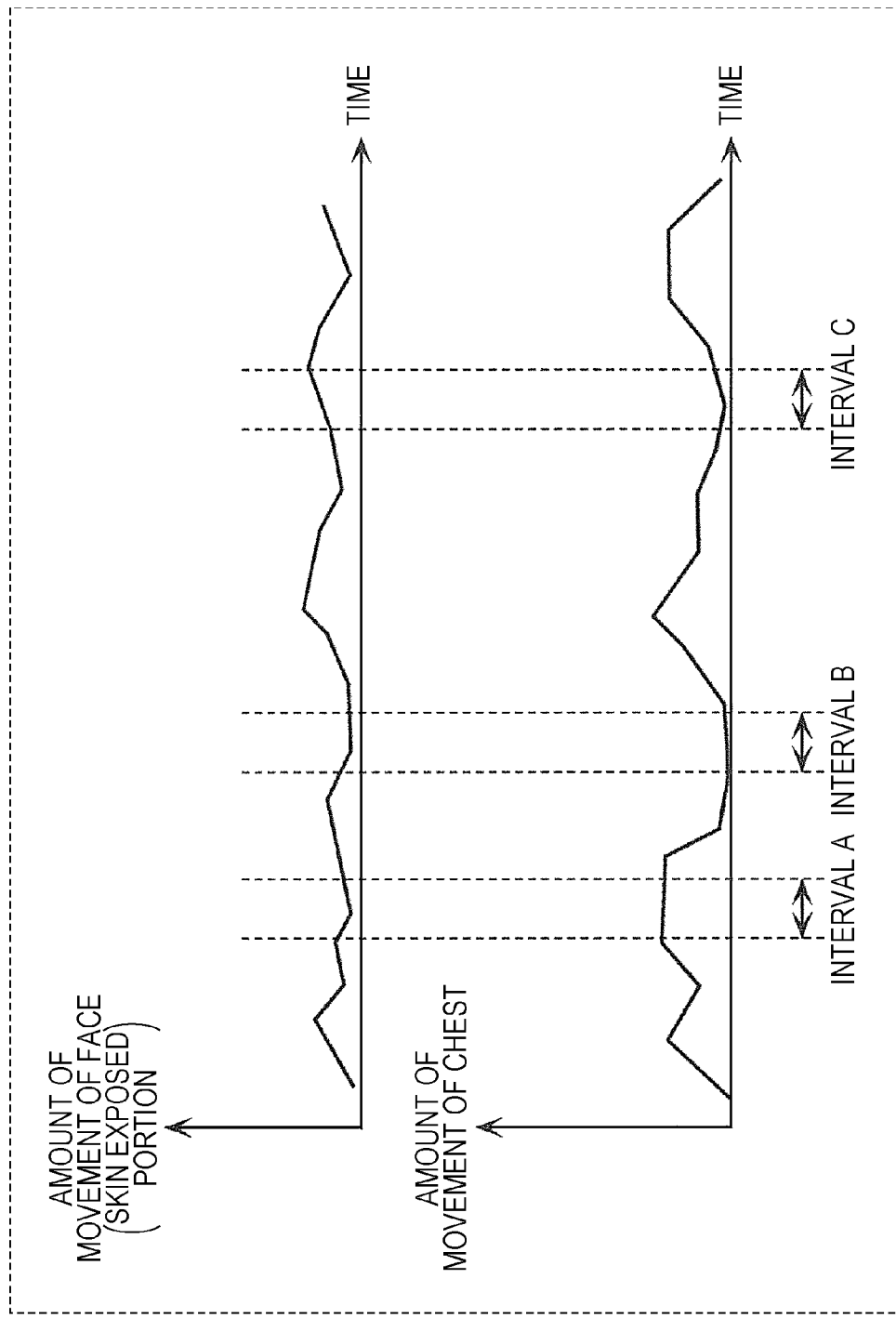

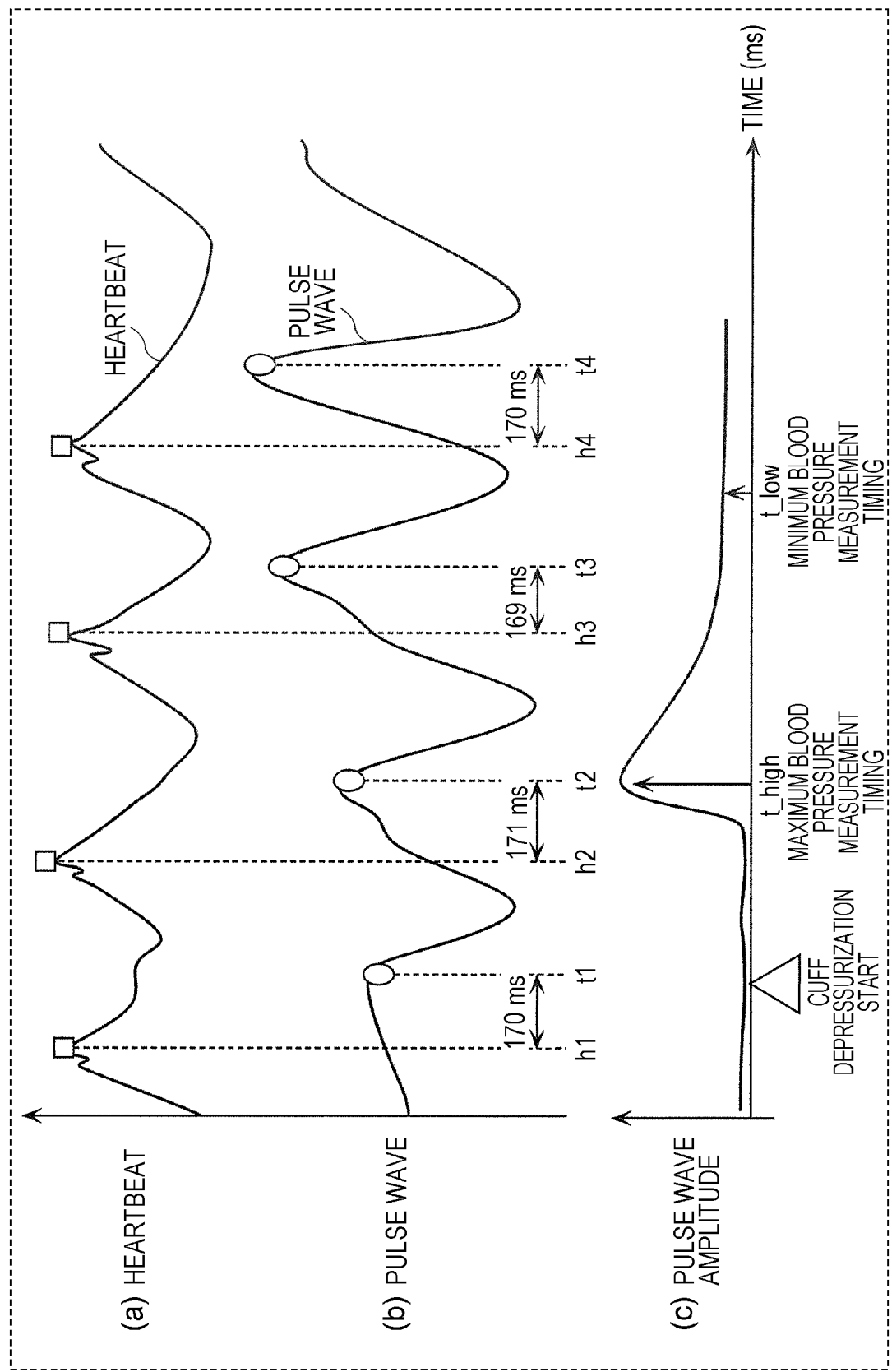

NON-CONTACT BLOOD-PRESSURE MEASURING DEVICE AND NON-CONTACT BLOOD-PRESSURE MEASURING METHOD

BACKGROUND

1. Technical Field

The present disclosure relates to A non-contact blood-pressure measuring device and a non-contact blood-pressure measuring method.

2. Description of the Related Art

Japanese Patent No. 5443899 discloses a device for estimating blood pressure from a time difference (pulse wave propagation period) between an electrocardiographic R-wave and a pulse wave obtained at a fingertip.

However, in the conventional art disclosed in Japanese Patent No. 5443899, it is necessary to attach an electrode, for example, to a chest in order to measure an electrocardiographic R-wave and to attach a pulse-wave measuring unit, for example, to a fingertip. This is inconvenient.

SUMMARY

One non-limiting and exemplary embodiment provides a non-contact blood-pressure measuring device that measures blood pressure in a non-contact manner.

In one general aspect, the techniques disclosed here feature a non-contact blood-pressure measuring device including: an image acquirer that acquires a skin image obtained by capturing skin of a user; a pulse-wave timing calculator that calculates a temporal change of luminance in the skin image by using the skin image and calculates, as a pulse-wave timing, time information indicative of a time at which the luminance reaches a peak; a radio wave acquirer that acquires a signal of a radio wave reflected by the user and received by a reception antenna; a heartbeat timing calculator that calculates a temporal change of a distance between the user and the reception antenna by using the signal of the radio wave acquired by the radio wave acquirer and calculates, as a heartbeat timing, time information indicative of a time at which the distance reaches a peak; and a blood-pressure determiner that determines blood pressure of the user on the basis of a time difference between the pulse-wave timing and the heartbeat timing.

The non-contact blood-pressure measuring device according to the present disclosure can measure blood pressure in a non-contact manner.

It should be noted that general or specific embodiments may be implemented as a system, a method, an integrated circuit, a computer program, a computer-readable storage medium such as a CD-ROM, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 4A is a second explanatory diagram for explaining calculation of a pulse-wave timing in Embodiment 1;

FIG. 4B is a third explanatory diagram for explaining calculation of a pulse-wave timing in Embodiment 1;

FIG. 5 is an explanatory diagram for explaining a calculated pulse-wave timing in Embodiment 1;

FIG. 6B is a first explanatory diagram for explaining calculation of a heartbeat timing in Embodiment 1;

FIG. 7 is a second explanatory diagram for explaining calculation of a heartbeat timing in Embodiment 1;

FIG. 8 is an explanatory diagram for explaining a calculated heartbeat timing in Embodiment 1;

FIG. 9 is an explanatory diagram for explaining processing for determining blood pressure on the basis of a pulse-wave timing and a heartbeat timing in Embodiment 1;

FIG. 15 is an explanatory diagram illustrating an example of models accumulated in a model accumulating section in Embodiment 1;

FIG. 20D is an explanatory diagram for explaining processing of a posture measuring section in Modification 1 of Embodiment 1;

FIG. 20E is an explanatory diagram for explaining a method for determining a measurement timing in Modification 1 of Embodiment 1;

FIG. 20H is an explanatory diagram for explaining a timing of determination of a parameter in Modification 2 of Embodiment 1;

DETAILED DESCRIPTION

Figure 1:
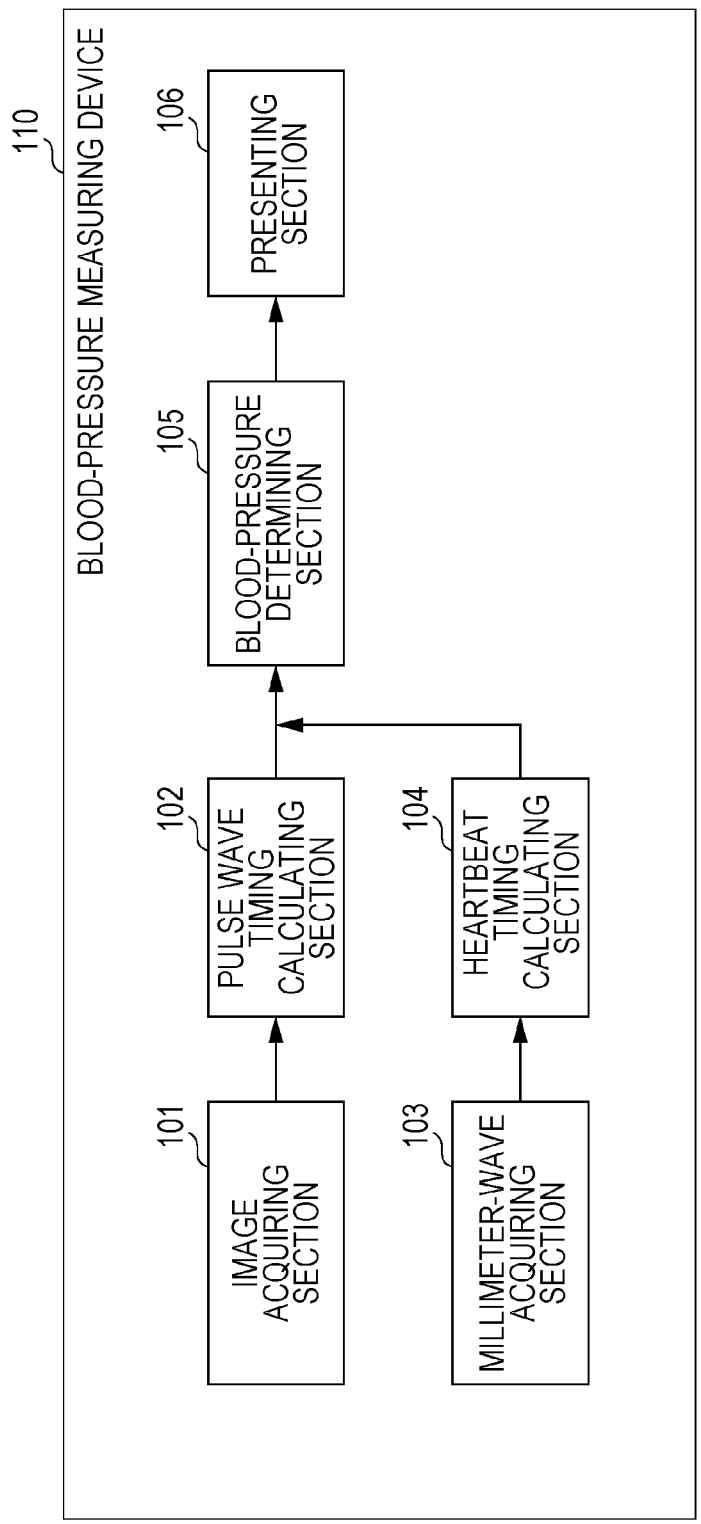
FIG. 1 is a first block diagram illustrating a configuration of a non-contact blood-pressure measuring device according to Embodiment 1.

Underlying Knowledge Forming Basis of the Present Disclosure

Blood pressure is a barometer essential for health, and it is recommended that blood pressure be frequently measured. Not only users with high blood pressure, but also users with low blood pressure sometimes temporarily get high blood pressure due to factors such as stress, smoking, and nocturnal hypertension. Therefore, frequent and routine measurement and management of blood pressure lead to promotion of health.

In the conventional art disclosed in Japanese Patent No. 5443899, it is necessary to attach an electrode, for example, to a chest in order to measure an electrocardiographic R-wave and to attach a pulse-wave measuring unit, for example, to a fingertip. This is inconvenient.

In view of this, the present disclosure provides a non-contact blood-pressure measuring device that measures blood pressure in a non-contact manner.

Specifically, the present disclosure provides a non-contact blood-pressure measuring device that measures blood pressure in a non-contact manner by using a change of image information such as luminance of a skin portion such as a face or a hand and a change of signal information of a chest obtained by using a millimeter wave sensor.

In order to attain such an object, a non-contact blood-pressure measuring device according to one aspect of the present disclosure includes: an image acquirer that acquires a skin image obtained by capturing skin of a user; a pulse-wave timing calculator that calculates a temporal change of luminance in the skin image by using the skin image and calculates, as a pulse-wave timing, time information indicative of a time at which the luminance reaches a peak; a radio wave acquirer that acquires a signal of a radio wave reflected by the user and received by a reception antenna; a heartbeat timing calculator that calculates a temporal change of a distance between the user and the reception antenna by using the signal of the radio wave acquired by the radio wave acquirer and calculates, as a heartbeat timing, time information indicative of a time at which the distance reaches a peak; and a blood-pressure determiner that determines blood pressure of the user on the basis of a time difference between the pulse-wave timing and the heartbeat timing.

According to the arrangement, the non-contact blood-pressure measuring device calculates a pulse-wave timing of a user (subject) in a non-contact manner on the basis of a skin image, calculates a heartbeat timing of the user in a non-contact manner on the basis of a signal of a radio wave, and determines blood pressure of the user by using the pulse-wave timing and the heartbeat timing. As described above, acquired from the user are the skin image and the signal of the radio wave, and these pieces of information are acquired in a non-contact manner. Therefore, the non-contact blood-pressure measuring device can measure blood pressure in a non-contact manner.

Furthermore, since the user can easily measure blood pressure in a non-contact manner by using the non-contact blood-pressure measuring device, it is possible to easily measure blood pressure under a routine environment. It is therefore possible to promote health of the user.

For example, the non-contact blood-pressure measuring device is arranged to further include a posture measurer that measures an amount of change of a posture of the user on the basis of the skin image acquired by the image acquirer; the blood-pressure determiner determining the blood pressure on the basis of a time difference between the pulse-wave timing calculated on the basis of the skin image acquired by the image acquirer during a period in which the amount of change measured by the posture measurer is equal to or lower than a predetermined threshold value and the heartbeat timing calculated on the basis of the radio wave acquired by the radio wave acquirer during the period.

According to the arrangement, the non-contact blood-pressure measuring device measures the blood pressure of the user in a case where the amount of change of the posture of the user is relatively small and is suitable for measurement of blood pressure by the non-contact blood-pressure measuring device. In a case where the change of the posture of the user is large, the accuracy of blood pressure that is output by the non-contact blood-pressure measuring device decreases. Therefore, the non-contact blood-pressure measuring device can avoid output of an inaccurate measurement result.

For example, the image acquirer acquires the skin image obtained by capturing a portion including the skin of the user and a chest of the user; the posture measurer measures, as the amount of change, an amount of movement of a skin portion of the skin image or an amount of movement of a chest portion of the skin image; and the blood-pressure determiner that determines the blood pressure on the basis of a time difference between the pulse-wave timing calculated on the basis of the skin image acquired by the image acquirer during a period in which the amount of movement of the skin portion or the chest portion measured by the posture measurer is equal to or lower than a predetermined threshold value and the heartbeat timing calculated on the basis of the radio wave acquired by the radio wave acquirer during the period.

According to the arrangement, the non-contact blood-pressure measuring device acquires the amount of change of the posture of the user, specifically, from the user's skin and chest. Therefore, the non-contact blood-pressure measuring device can avoid output of an inaccurate measurement result.

For example, the image acquirer includes an acquirer for posture measurement that acquires an image obtained by capturing the user from a direction different from a direction in which the radio wave acquirer acquires a radio wave; and the posture measurer measures the amount of change on the basis of the image acquired by the acquirer for posture measurement.

According to the arrangement, the non-contact blood-pressure measuring device can acquire a change of the posture of the user on the basis of an image that is acquired from a direction in which a change of the posture of the user can be more easily detected. It is assumed that the image acquired for calculation of a pulse-wave timing is an image obtained by capturing the front of the user. Meanwhile, the accuracy of calculation of a pulse-wave timing is much lower in a case where the user moves forward and backward than in a case where the user moves sideways. Therefore, by acquiring a change of the posture of the user on the basis of an image that is obtained by capturing the user not from the front but from the side or an oblique direction of the user, it is possible to more accurately acquire a change of the posture of the user. Therefore, the non-contact blood-pressure measuring device can avoid output of an inaccurate measurement result.

For example, the blood-pressure determiner determines the blood pressure on the basis the time difference between the pulse-wave timing calculated by the pulse-wave timing calculator and the heartbeat timing calculated by the heartbeat timing calculator by using a predetermined relational expression including a predetermined parameter and the time difference.

According to the arrangement, the non-contact blood-pressure measuring device can determine the blood pressure of the user, specifically, by calculating blood pressure on the basis of a time difference between a pulse-wave timing and a heartbeat timing by using a relational expression.

For example, the non-contact blood-pressure measuring device further includes a cuff-type blood pressure measurer that measures the blood pressure of the user by using a cuff; and the blood-pressure determiner determines the predetermined parameter included in the relational expression by using the blood pressure of the user measured by the cuff-type blood pressure measurer.

According to the arrangement, the non-contact blood-pressure measuring device determines a parameter included in the relational expression used to determine the blood pressure of the user by using a result of cuff-type blood pressure measurement, which is used for conventional blood pressure measurement. Therefore, the non-contact blood-pressure measuring device can more accurately measure the blood pressure of the user.

For example, the pulse-wave timing calculator calculates a plurality of pulse-wave timings; the heartbeat timing calculator calculates a plurality of heartbeat timings that correspond to the respective calculated pulse-wave timings; and the blood-pressure determiner determines the predetermined parameter included in the relational expression on the basis of (i) a time difference determined on the basis of a pair of pulse-wave timing and heartbeat timing included in a period from a first timing at which maximum blood pressure is measured by the cuff-type blood pressure measurer to a second timing at which minimum blood pressure is measured by the cuff-type blood pressure measurer, (ii) a time difference determined on the basis of a pair of pulse-wave timing and heartbeat timing that is closest to the first timing, or (iii) a time difference determined on the basis of a pair of pulse-wave timing and heartbeat timing that is closest to the second timing, among pairs of pulse-wave timing and heartbeat timing that correspond to each other.

According to the arrangement, the non-contact blood-pressure measuring device determines a parameter included in the relational expression by using a pulse-wave timing and a heartbeat timing acquired at a timing that is relatively close to a timing of cuff-type blood pressure measurement. Therefore, the non-contact blood-pressure measuring device can more accurately measure the blood pressure of the user.

For example, the skin image is a skin image obtained by capturing skin of a portion anterior to a portion at which the cuff-type blood pressure measurer is attached among portions of an arm of the user.

According to the arrangement, the non-contact blood-pressure measuring device calculates a pulse-wave timing on the basis of a skin image of a portion, such as a hand, anterior to an arm of the user at which cuff-type blood pressure measurement is performed. The parameter included in the relational expression can be more accurately determined by using blood pressure obtained by the cuff-type blood pressure measurement from the arm of the user at which cuff-type blood pressure measurement is performed and blood pressure obtained on the basis of a time difference between the pulse-wave timing and the heartbeat timing. Therefore, the non-contact blood-pressure measuring device can more accurately measure the blood pressure of the user.

For example, the pulse-wave timing is a timing at which the luminance changes from a state in which it rises or remains constant over passage of time to a state in which it falls over passage of time.

According to the arrangement, the non-contact blood-pressure measuring device can more accurately acquire a pulse-wave timing of the user. It is known that the luminance in the skin image decreases due to a pulse wave of the user. Therefore, the non-contact blood-pressure measuring device can more accurately acquire a timing of a pulse wave of the user not just by searching for a peak of the luminance, but by acquiring a timing of a decrease of the luminance.

For example, the pulse-wave timing calculator calculates a plurality of pulse-wave timings; the heartbeat timing calculator calculates a plurality of heartbeat timings that correspond to the respective calculated pulse-wave timings; and the blood-pressure determiner calculates a plurality of time differences on the basis of respective pairs of pulse-wave timing and heartbeat timing that correspond to each other and determines the blood pressure on the basis of a value obtained by performing statistical processing on the calculated plurality of time differences.

According to the arrangement, the non-contact blood-pressure measuring device measures the blood pressure of the user and presents the blood pressure to the user every time a heartbeat of the user occurs. This allows the user to obtain a measurement result in a relatively short period of time from the start of measurement of blood pressure by the non-contact blood-pressure measuring device and to obtain successive measurement results of the blood pressure.

For example, the pulse-wave timing calculator calculates a plurality of pulse-wave timings; the heartbeat timing calculator calculates a plurality of heartbeat timings that correspond to the respective calculated pulse-wave timings; and the non-contact blood-pressure measuring device further includes a first presenter that presents, in association with respective acquisition times, a plurality of time differences between respective pairs of pulse-wave timing and heartbeat timing that correspond to each other.

According to the arrangement, the non-contact blood-pressure measuring device presents successively-measured blood pressure to the user. This allows the user to grasp a transition of the blood pressure thanks to the presentation by the non-contact blood-pressure measuring device.

For example, the non-contact blood-pressure measuring device further includes: a model accumulator in which candidates of the predetermined parameter included in the relational expression are stored; and an acceptor that accepts profile information including at least one of height, weight, age, and blood pressure of the user, the blood-pressure determiner determining a candidate to be used to determine the blood pressure among the candidates stored in the model accumulator on the basis of the profile information accepted by the acceptor and determines the blood pressure by using the relational expression including the determined candidate.

According to the arrangement, the non-contact blood-pressure measuring device can determine, on the basis of the profile information of the user, a relational expression for determining blood pressure on the basis of the pulse-wave timing and the heartbeat timing. This makes it possible to further improve the accuracy of the determined blood pressure.

For example, the non-contact blood-pressure measuring device further includes a second presenter that presents information designating a position of a body of the user so that the body of the user is located at a position suitable for acquisition of the skin image by the image acquirer and for acquisition of the radio wave by the radio wave acquirer.

According to the arrangement, the non-contact blood-pressure measuring device presents information to the user so that the body of the user is located at a position suitable for blood pressure measurement by the non-contact blood-pressure measuring device. In a case where the user changes the position of the body in accordance with this information, the accuracy of information acquired by the non-contact blood-pressure measuring device (especially the radio wave acquirer) improves. It is therefore possible to more accurately determine the blood pressure of the user.

For example, the second presenter further presents, to the user, instruction information instructing the user to stay still, to be at rest, to inhale, or to exhale when the image acquirer acquires the skin image and when the radio wave acquirers acquires the radio wave.

According to the arrangement, the non-contact blood-pressure measuring device gives the user an instruction concerning movement of the body of the user or a timing of breathing. This allows the non-contact blood-pressure measuring device (especially the radio wave acquirer) to acquire information while the user is moving his or her body in a manner suitable for measurement or is breathing at a timing suitable for measurement. It is therefore possible to more accurately determine the blood pressure of the user.

For example, the second presenter further presents the skin image to the user instantaneously every time the skin image is acquired by the image acquirer.

This allows the non-contact blood-pressure measuring device to be used as a mirror even in a case where the non-contact blood-pressure measuring device does not include a physical mirror.

For example, the non-contact blood-pressure measuring device further includes: a skin region specifier that specifies a skin region which is a predetermined skin portion in the skin image acquired by the image acquirer; a chest region specifier that specifies a chest region which is a chest portion of the user in the skin image acquired by the image acquirer; and a respiratory component calculator that calculates a respiratory component included in a time-varying movement vector of a feature point within the chest region specified by the chest region specifier, the pulse-wave timing calculator calculating the pulse-wave timing on the basis of time-varying luminance in the skin region, and the heartbeat timing calculator calculating the heartbeat timing on the basis of a time-varying distance to the user obtained on the basis of the signal of the radio wave acquired by the radio wave acquirer and the respiratory component calculated by the respiratory component calculator.

According to the arrangement, the non-contact blood-pressure measuring device calculates a heartbeat timing by further using a respiratory component obtained on the basis of an image. By thus using not only a heartbeat timing obtained on the basis of a signal of a radio wave, but also a respiratory component obtained on the basis of an image, it is possible to improve the accuracy of a calculated heartbeat timing.

For example, the heartbeat timing calculator calculates the heartbeat timing on the basis of a radio wave acquired by the radio wave acquirer during a predetermined period including a peak or a bottom of the respiratory component that periodically changes over passage of time.

According to the arrangement, the non-contact blood-pressure measuring device can calculate a heartbeat timing by using an image and a signal of a radio wave that are obtained from the user during a period including a peak or a bottom of a respiratory component in the image, which is a period less affected by breathing. This makes it possible to further improve the accuracy of the determined blood pressure.

For example, the heartbeat timing calculator calculates a frequency of the respiratory component that periodically changes over passage of time and calculates the heartbeat timing by filtering a periodical change in a frequency band including the calculated frequency in the signal of the radio wave acquired by the radio wave acquirer.

According to the arrangement, the non-contact blood-pressure measuring device can more accurately calculate a heartbeat timing by filtering a frequency of a periodical fluctuation of the respiratory component.

For example, the heartbeat timing calculator calculates the heartbeat timing by performing adaptive filtering by using the respiratory component and the signal of the radio wave acquired by the radio wave acquirer.

According to the arrangement, the non-contact blood-pressure measuring device can more accurately calculate a heartbeat timing by adaptive filtering.

For example, the chest region specifier further specifies a shoulder line of the user included in the skin image, sets the feature point on the specified shoulder line, and calculates the respiratory component by using the set feature point.

According to the arrangement, the non-contact blood-pressure measuring device acquires a respiratory component of the user from a shoulder line of the user in the image. In a case where feature points are set on the shoulder line of the user, feature points (corresponding points) can be more easily obtained at each point in time over passage of time, and therefore a respiratory component can be more accurately acquired. This makes it possible to further improve the accuracy of the determined blood pressure.

A non-contact blood-pressure measuring method according to one aspect of the present disclosure includes: (a) acquiring a skin image obtained by capturing skin of a user; (b) calculating, as a pulse-wave timing, time information indicative of a time at which time-varying luminance in the skin image reaches a peak; (c) acquiring a signal of a radio wave reflected by the user; (d) calculating, as a heartbeat timing, time information indicative of a time at which a time-varying distance to the user obtained on the basis of the signal of the radio wave acquired in the (c) acquiring reaches a peak; and (e) determining blood pressure of the user on the basis of a time difference between the pulse-wave timing and the heartbeat timing.

This produces effects similar to those produced by the non-contact blood-pressure measuring device.

It should be noted that these general or specific embodiments may be implemented as a system, a method, an integrated circuit, a computer program, a computer-readable storage medium such as a CD-ROM, or any selective combination thereof.

Embodiments are described below with reference to the drawings.

Note that the embodiments described below illustrate general or specific examples. Numerical values, shapes, materials, constituent elements, positions of the constituent elements, forms of connection of the constituent elements, steps, the order of steps, and the like described in the embodiments below are merely examples and do not limit the present disclosure. Furthermore, constituent elements that are not described in independent claims, which recite the highest concepts, among the constituent elements described in the embodiments below are described as optional constituent elements.

Embodiment 1

In the present embodiment, a non-contact blood-pressure measuring device that measures blood pressure in a non-contact manner is described.

Figure 2A:
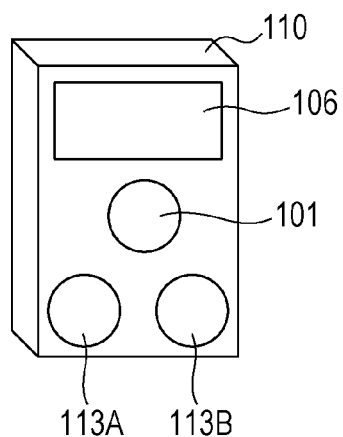
FIG. 2A is a first appearance diagram of the non-contact blood-pressure measuring device according to Embodiment 1.
Figure 2B:
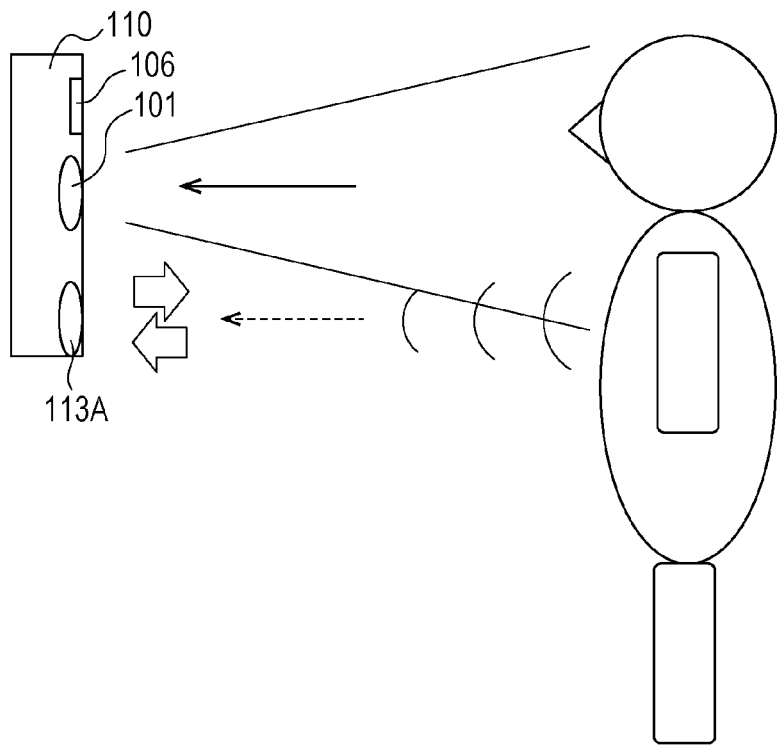
FIG. 2B is a schematic view illustrating how the non-contact blood-pressure measuring device according to Embodiment 1 is used by a user.

A non-contact blood-pressure measuring device 110 according to the present embodiment is described below. FIG. 1 is a first block diagram illustrating a configuration of the non-contact blood-pressure measuring device 110 according to the present embodiment. FIG. 2A is an appearance diagram of the non-contact blood-pressure measuring device 110 according to the present embodiment. FIG. 2B is a schematic view illustrating a state in which the non-contact blood-pressure measuring device 110 according to the present embodiment is being used by a user.

As illustrated in FIG. 1, the non-contact blood-pressure measuring device 110 includes an image acquiring section 101, a pulse-wave timing calculating section 102, a millimeter-wave acquiring section 103, a heartbeat timing calculating section 104, a blood-pressure determining section 105, and a presenting section 106.

Specifically, the non-contact blood-pressure measuring device 110 includes the image acquiring section 101 that acquires a skin image obtained by capturing a user's skin, the pulse-wave timing calculating section 102 that calculates, as a pulse-wave timing, time information indicative of a time at which time-varying luminance in the skin image reaches a peak, the millimeter-wave acquiring section 103 that acquires a signal of a millimeter-wave reflected by the user, the heartbeat timing calculating section 104 that calculates, as a heartbeat timing, time information indicative of a time at which a time-varying distance to the user obtained from the signal of the millimeter-wave acquired by the millimeter-wave acquiring section 103 reaches a peak, and the blood-pressure determining section 105 that determines blood pressure of the user on the basis of a time difference between the pulse-wave timing and the heartbeat timing. These functional blocks will be described later in detail.

FIG. 2A illustrates an example of an external shape of the non-contact blood-pressure measuring device 110. As illustrated in FIG. 2A, the functional blocks of the non-contact blood-pressure measuring device 110 are disposed in a single chassis.

A transmitting section 113A that transmits a millimeter wave, a receiving section 113B that receives a millimeter wave, the image acquiring section 101 that captures an image, and the presenting section 106 that presents information are provided on a front surface of the chassis of the non-contact blood-pressure measuring device 110.

A millimeter wave emitted by the transmitting section 113A is reflected by a person, and the reflected signal is received by the receiving section 113B. Presence of the person or movement of the person is thus detected. In the present disclosure, the non-contact blood-pressure measuring device 110 detects a heartbeat that occurs due to heart contraction on the basis of the signal reflected by the chest of the person. Furthermore, the image acquiring section 101 captures an image of the face or a hand of the person and detects a pulsebeat, for example, on the basis of a change of luminance in the image. Then, the non-contact blood-pressure measuring device 110 determines blood pressure on the basis of a pulse wave propagation period, which is a time difference between the heartbeat and the pulsebeat, and the presenting section 106 presents the determined blood pressure. Details of the constituent elements and the present disclosure are described below.

Image Acquiring Section 101

The image acquiring section 101 acquires a skin image, which is an image obtained by capturing skin of the face or a hand of a person. The skin image is an image that is obtained by capturing an identical portion of the person at a plurality of successive timings. The skin image is, for example, a moving image or a plurality of still images.

The image acquiring section 101 may acquire a skin image by capturing an image or may acquire a skin image by acquiring data of a skin image captured by another device or the like. In a case where the image acquiring section 101 acquires a skin image by capturing an image, the image acquiring section 101 is realized by a camera or the like including an image sensor such as a CCD (Charge Coupled Device) or a CMOS (Complementary Metal Oxide Semiconductor Image Sensor).

Pulse-Wave Timing Calculating Section 102

The pulse-wave timing calculating section 102 calculates a pulse-wave timing on the basis of a change of time-varying luminance of the skin image acquired by the image acquiring section 101.

In general, when a heart contracts, blood is delivered from the heart, and the delivered blood reaches a face, a hand, or the like. The luminance of the face or the hand in a captured image changes depending on the amount of component in the blood such as hemoglobin.

In an image captured by using visible light, a large change of luminance appears in image information of a frequency band including the vicinity of a frequency corresponding to green. For example, the luminance of green in pixels that correspond to the face or the hand to which a relatively large amount of blood has been supplied is lower than that in pixels that correspond to the face or the hand to which a relatively small amount of blood has been supplied. Therefore, the pulse-wave timing calculating section 102 calculates a timing of a pulse wave by using a temporal change of the luminance in the skin image. Note that a timing of a pulse wave is a time at which a peak of the waveform of the pulse wave is obtained. That is, the pulse-wave timing calculating section 102 calculates, as a pulse-wave timing, time information indicative of a time at which time-varying luminance in the skin image reaches a peak.

Figure 3:
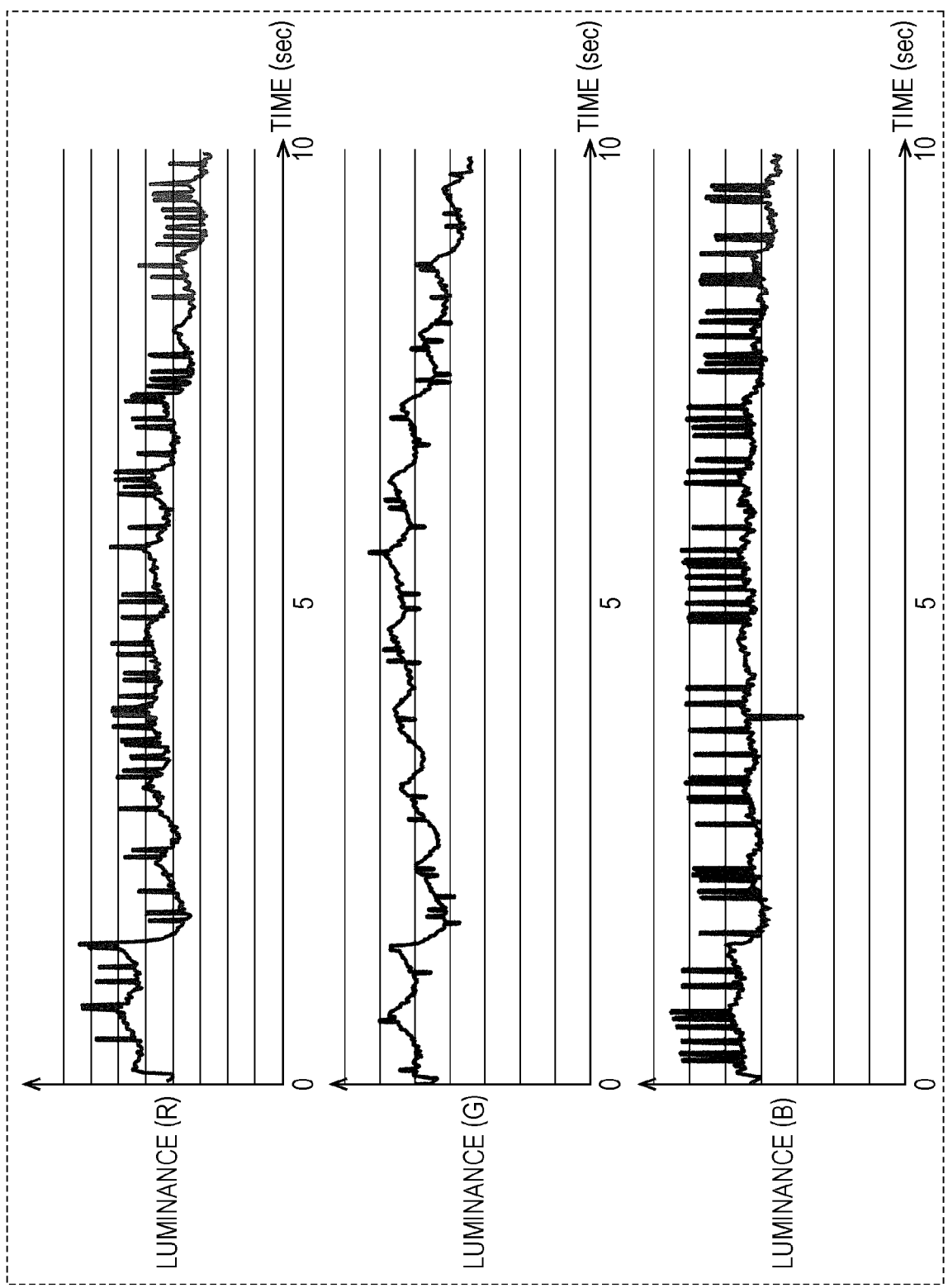
FIG. 3 is a first explanatory diagram for explaining calculation of a pulse-wave timing in Embodiment 1.

FIG. 3 is a first explanatory diagram for explaining calculation of a pulse-wave timing in the present embodiment. Specifically, FIG. 3 is a diagram illustrating a change of luminance of each of red (R), green (G), and blue (B) components of a cheek region of an image which the image acquiring section 101 acquires by capturing a human face. In FIG. 3, the horizontal axis represents a time, and the vertical axis represents a change of luminance.

As is clear from FIG. 3, the luminance of R, G, and B (hereinafter simply referred to as "RGB") periodically changes due to pulse waves. An image captured under a routine environment contains noise due to scattering light or various factors, and it is desirable that a signal change caused by a pulse wave be calculated after subjecting the image to signal processing such as filtering. In the present embodiment, a change of the luminance of G in an image that has been subjected to low-pass filtering is used. Note that various methods can be used to calculate a timing of arrival of a pulse wave on the basis of the time-varying luminance. For example, local search such as hill climbing can be used.

Note that a more accurate pulse-wave timing can be calculated in a case where a peak is calculated as a timing at which luminance changes from a state where it rises or remains constant over passage of time to a state where it falls over passage of time.

FIG. 4A is a second explanatory diagram for explaining calculation of a pulse-wave timing in the present embodiment. Specifically, FIG. 4A is a diagram for explaining calculation of a pulse-wave timing. In FIG. 4A, the pulse-wave timing calculating section 102 sets a time t2 as a current reference point. The pulse-wave timing calculating section 102 compares a luminance value at the time t2 with a luminance value at a time t1, which is one time point earlier than the time t2, and with a luminance value at a time t3, which is one time point later than the time t2, and thus determines whether or not the luminance value at the reference point is larger than both of the luminance value at the time t1 and the luminance value at the time t3. In this case, the luminance value at the time t2 is larger than the luminance value at the time t1 but is smaller than the luminance value at the time t3. Therefore, the result of the determination is "NO", and the reference point is incremented to the time t3.

The pulse-wave timing calculating section 102 performs similar determination while setting the time t3 as a reference point. Specifically, the luminance value at the time t3 is larger than that at the time t2, which is one time point earlier than the time t3, and that at a time t4, which is one time point later than the time t3, and therefore the result of the determination is "YES". Therefore, the pulse-wave timing calculating section 102 determines that the reference point has reached a local peak and specifies the time t3 as a timing at which a pulse wave started to arrive.

FIG. 4B is a third explanatory diagram for explaining calculation of a pulse-wave timing in the present embodiment. Specifically, FIG. 4B is a graph illustrating a change of the luminance of G in an image that has been subjected to low-pass filtering. In FIG. 4B, pulse-wave timings calculated by peak search are indicated by the white circles.

FIG. 5 is an explanatory diagram for explaining calculated pulse-wave timings in the present embodiment. Specifically, FIG. 5 is a diagram for explaining that the timings calculated as described above are due to pulse waves.

FIG. 5 illustrates pulse-wave timings that are measured by attaching a photoelectric fingertip pulse wave measurement instrument to a fingertip of a person. Furthermore, FIG. 5 also illustrates pulse-wave timings calculated on the basis of a change of luminance in a captured moving image of a face. FIG. 5 illustrates transitions of time intervals (time intervals between a pulse wave and a next pulse wave) between the pulse-wave timings calculated by these two methods. In FIG. 5, the white circles are pulse waves obtained by using the fingertip pulse wave measurement instrument, and the black rectangles are pulse waves obtained from the moving image. In FIG. 5, the horizontal axis represents a pulse wave interval, and the vertical axis represents the duration (millisecond) of the pulse wave interval.

As illustrated in FIG. 5, a time interval between pulse waves is not constant and fluctuates between approximately 700 ms and 820 ms. As is clear from FIG. 5, pulse wave intervals having a very high time correlation with pulse wave intervals between fingertip pulse waves can also be obtained on the basis of a change of luminance in the face image. This shows that not only the number of pulse waves per minute, but also timings of pulse waves at which blood flows into the face can be detected with relatively high accuracy by using the change of the luminance in the image.

Note that a method of peak search is not limited to hill climbing and can be an autocorrelation method, a method using a differential function, or other peak search methods. Alternatively, since pulse waves are extracted, it is also possible to use knowledge-based processing such as processing for obtaining a peak interval, for example, between 1000 ms and 333 ms on the basis of knowledge of a general pulse wave (for example, from 60 bpm to 180 bpm). This achieves robust pulse wave timing extraction under a routine environment.

Millimeter-Wave Acquiring Section 103

See FIG. 1 again. The millimeter-wave acquiring section 103 is a control circuit that acquires a signal of a millimeter-wave reflected by a person. The millimeter-wave acquiring section 103 may include a reception antenna and acquire a signal of a millimeter-wave by receiving the millimeter wave via the reception antenna. Alternatively, the millimeter-wave acquiring section 103 may acquire a signal of a millimeter-wave by acquiring data of the signal of the millimeter-wave received by another device or the like.

In a case where the millimeter-wave acquiring section 103 receives a millimeter wave, the millimeter-wave acquiring section 103 is constituted by transmitting and receiving circuits of a radar utilizing a millimeter wave band. Specifically, the millimeter-wave acquiring section 103 has the transmitting section 113A (transmitting circuit) that transmits a millimeter wave and the receiving section 113B (receiving circuit) that receives a millimeter wave. The millimeter-wave acquiring section 103 detects a distance to a target on the basis of a time difference between a time of transmission of a transmission wave and a time of reception of a reflected wave, which is the transmission wave reflected by the target. Furthermore, the millimeter-wave acquiring section 103 detects movement or speed of the target on the basis of a phase or frequency difference between the transmission wave and the reflected wave. Furthermore, the millimeter-wave acquiring section 103 detects a distance to an object on the basis of a difference in arrival direction obtained by using an array antenna. Note that various techniques such as a technique (Japanese Patent No. 5198603) using code modulation for the purpose of preventing collision of cars or for higher accuracy are known as a technique of a millimeter wave radar, and detail of the millimeter wave radar are not limited in particular.

The phase of the millimeter wave acquired by the millimeter-wave acquiring section 103 changes depending on a change of the distance between the millimeter-wave acquiring section 103 and the person that occurs due to a beat of the heart of the person. Accordingly, in a case where the millimeter-wave acquiring section 103 successively acquires a millimeter wave, the acquired millimeter waves include information on a time-series change of the distance between the millimeter-wave acquiring section 103 and the person. In the present embodiment, the distance between the millimeter-wave acquiring section 103 and the person is a distance between the reception antenna and the person.

Note that similar processing can also be achieved by using a radio wave in a band different from a millimeter wave band. In this case, a radio-wave acquiring section is used instead of the millimeter-wave acquiring section 103. The radio-wave acquiring section is similar to the millimeter-wave acquiring section 103 except for that the radio-wave acquiring section uses a radio wave in a band different from a millimeter wave band.

Figure 6A:
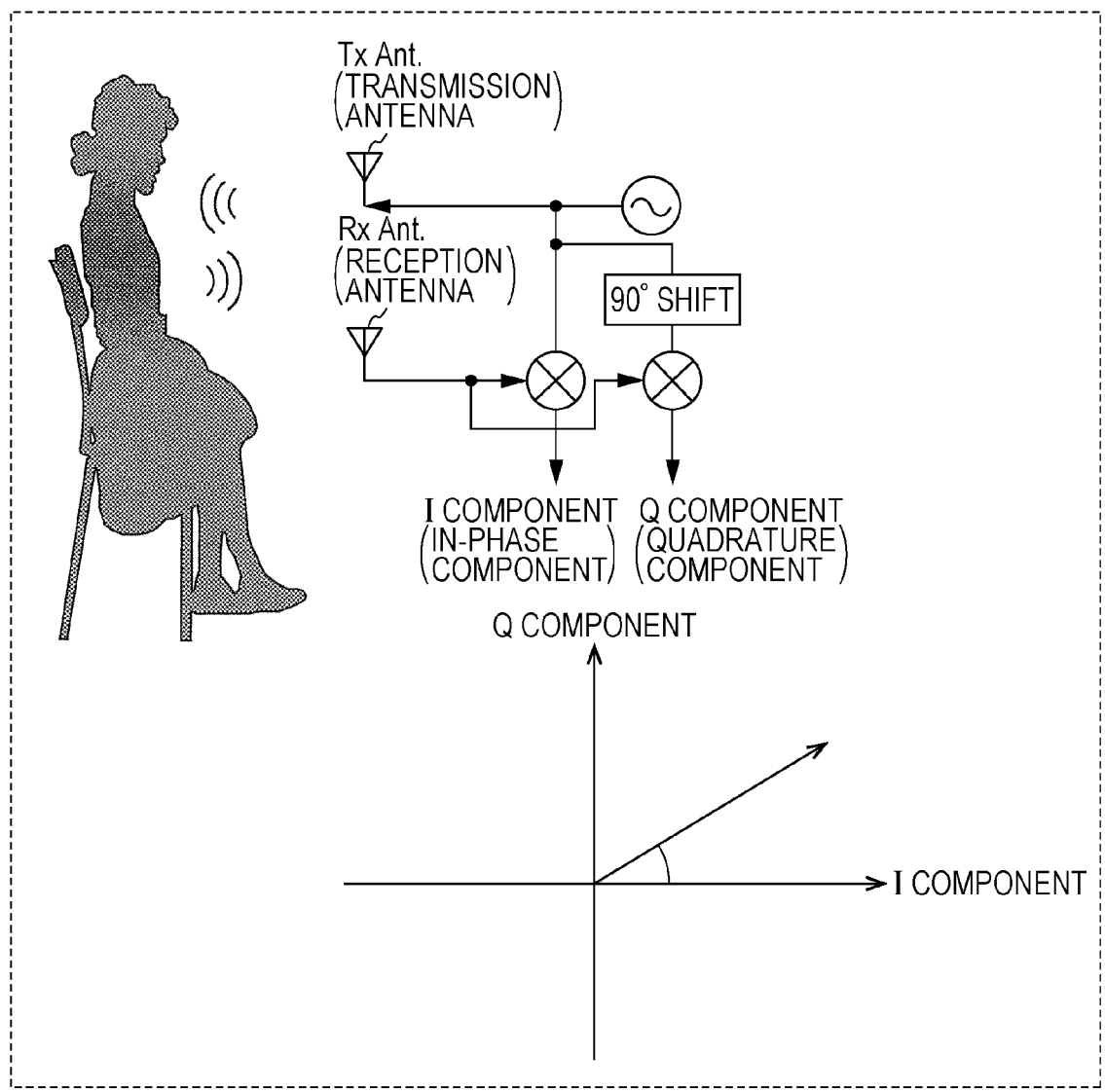
FIG. 6A is an explanatory diagram illustrating the principle of calculation of a heartbeat timing in Embodiment 1.

FIG. 6A is an explanatory diagram illustrating the principle of calculation of a heartbeat timing in the present embodiment.

The millimeter-wave acquiring section 103 causes the transmitting section 113A to transmit a predetermined frequency signal or a predetermined pulse wave and causes the receiving section 113B to receive a signal reflected by a reflection object. The transmitted signal is frequency-modulated, amplitude-modulated, or code-modulated so that a timing of transmission of the signal is clear. Then, a distance is measured on the basis of a difference in arrival time. In the present embodiment, for example, a change of body movement of the chest of a person that occurs due to heart contraction or pulsation is detected on the basis of millimeter-ter waves reflected by the chest of the person. Since movement such as a heartbeat or breathing is extremely small, the change of the distance is calculated by using a signal phase difference in addition to the difference in arrival time. The distance is calculated by using expressions (1) through (5).

$$r(t)=A(t)\cos(2\pi f_0(t-2d/c)) \quad (1)$$

where r(t) is a reflected signal.

An in-phase component (I) and an orthogonal component (Q) of this signal are expressed by the expressions (2) and (3), respectively, and the phase is calculated by the expression (4).

$$I(t)=A(t)\cos(4\pi f_0 d/c) \quad (2)$$

$$Q(t)=A(t)\sin(4\pi f_0 d/c) \quad (3)$$

$$\text{phase}=(4\pi f_0 d/c)=\tan^{-1}(Q/I) \quad (4)$$

The distance is calculated by the expression (5) on the basis of the phase of the expression (4), the distance 2d over which the signal travels back and forth, the speed of light c, the wavelength $2\pi f$, and the like.

$$d=c/4\pi f_0 \tan^{-1}(Q/I) \tag{5}$$

FIG. 6B is a first explanatory diagram for explaining calculation of a heartbeat timing in the present embodiment. Specifically, FIG. 6B is a diagram illustrating a change of body movement (distance) of the chest.

FIG. 6B illustrates a change of the phase of a wave reflected by the chest of a person that is obtained by using a spread spectrum radar using a 26 GHz band. The spread spectrum radar can freely set a relation between distance resolution and a maximum detection distance by adjusting a chip rate and a code period of a PN code. For example, it is thus possible to grasp a subtle change of the chest by adjusting the range to the chest. In FIG. 6B, the horizontal axis represents a time, and the vertical axis represents a phase change. As is clear from FIG. 6B, the distance changes in accordance with a heartbeat with which the heart contracts.

Heartbeat Timing Calculating Section 104

See FIG. 1 again. The heartbeat timing calculating section 104 calculates a timing of a heartbeat on the basis of information on a phase change. A timing of a heartbeat can be calculated, for example, by a predetermined peak search method as in FIG. 4.

FIG. 7 is a second explanatory diagram for explaining calculation of a heartbeat timing in the present embodiment. Specifically, FIG. 7 is a diagram illustrating heartbeat timings obtained by peak search. In FIG. 7, the horizontal axis represents a time, and the vertical axis represents a phase change as in FIG. 6. Obtained peaks are indicated by the white circles.

FIG. 8 is an explanatory diagram for explaining calculated heartbeat timings in the present embodiment. FIG. 8 is a diagram for explaining that the obtained timings are due to heartbeats.

An electrocardiograph was attached to the vicinity of the heart of a person, and thus a heartbeat timing, called an R-wave, of the person to which the electrocardiograph was attached was measured. In addition to measurement of a heartbeat timing using the electrocardiograph, measurement of a heartbeat timing using a millimeter wave was performed in which a heartbeat timing was calculated on the basis of a phase change. A transition of an interval between heartbeat timings measured by using the electrocardiograph and a transition of an interval between heartbeat timings measured by using a millimeter wave are illustrated as a graph in FIG. 8. In FIG. 8, the white circles each indicate an interval (heartbeat interval) between heartbeat timings measured by using the electrocardiograph, and the black rectangles each indicate a heartbeat interval measured by using a millimeter wave. In FIG. 8, the horizontal axis represents a time, and the vertical axis represents the duration (millisecond) of a pulse wave interval.

As illustrated in FIG. 8, a time interval between heartbeats (so-called RRI (R-R Interval)) is not constant and fluctuates between approximately 600 ms and 950 ms. Furthermore, as is clear from FIG. 8, heartbeat intervals having an extremely high time correlation with RRIs measured by using the electrocardiograph are also obtained on the basis of the phase change of the millimeter wave. This shows that a timing of a heartbeat that occurs due to heart contraction can be detected with relatively high accuracy by using a phase change of a millimeter wave.

Blood-Pressure Determining Section 105

See FIG. 1 again. The blood-pressure determining section 105 determines the blood pressure of a user on the basis of a time difference (called a pulse wave propagation period) between a timing of a pulse wave obtained by the pulse-wave timing calculating section 102 and a timing of a heartbeat obtained by the heartbeat timing calculating section 104. More specifically, the blood-pressure determining section 105 determines the blood pressure of a user on the basis of a time difference between a timing of a heartbeat and a timing of a pulse wave corresponding to the heartbeat. The expression "pulse wave corresponding to the heartbeat" refers to a relation between a heartbeat and a pulse wave that occurs due to the heartbeat.

In general, it is said that there is a correlation between blood pressure and a time interval (pulse wave propagation period) from a point in time at which blood starts to flow due to heart contraction to a point in time at which the blood reaches a fingertip or the like. Specifically, the pulse wave propagation period becomes shorter as the blood pressure becomes higher, and the pulse wave propagation period becomes longer as the blood pressure becomes lower. A method for determining blood pressure by expressing this relation between the blood pressure and the pulse wave propagation period by using a predetermined approximate expression is conventionally known. The predetermined approximate expression may be a linear function, a combination of a plurality of linear functions, or a quadratic or higher-order function.

In the present embodiment, blood pressure is determined, for example, by using the following expression (6) as the predetermined approximate expression:

$$P=\alpha t+\beta \tag{6}$$

In the expression (6), t is the pulse wave propagation period, and $\alpha$ and $\beta$ are coefficients (parameters). In the present embodiment, for example, the coefficient $\alpha$ is set to −0.8, and the coefficient $\beta$ is set to 250.

FIG. 9 is an explanatory diagram for explaining determination of blood pressure based on a pulse-wave timing and a heartbeat timing in the present embodiment. In the schematic view of FIG. 9, the vertical axis represents a phase change of a millimeter wave and a luminance change in an image, and the horizontal axis represents a time.

In FIG. 9, timings of heartbeats calculated on the basis of a change of the phase of a millimeter wave are indicated by the white rectangles. The timings of the heartbeats are h1, h2, h3, and h4. In FIG. 9, pulse-wave timings calculated on the basis of a change of the luminance in the image are indicated by the white circles. The pulse wave timings are t1, t2, t3, and t4.

As illustrated in FIG. 9, there is a predetermined time difference between a timing of a heartbeat and a timing of a pulse wave. The blood-pressure determining section 105 determines blood pressure on the basis of this time difference. For example, a time difference between the time h1 and the time t1 is 170 ms. Therefore, the blood-pressure determining section 105 determines that the blood pressure is 114 mmHg (=−0.8×170+250) according to the expression (6).

Note that the blood-pressure determining section 105 may use a value obtained by performing statistical processing on a plurality of pulse wave propagation periods. The statistical processing is, for example, processing for obtaining an average, processing for obtaining a median, or the like. For example, in a case where the processing for obtaining an average is performed as the statistical processing, the average is 170 ms because measured four pulse wave propagation periods are 170 ms, 171 ms, 169 ms, and 171 ms. Therefore, it is determined that the blood pressure is 114 mmHg. There are cases where the pulse wave and heartbeat timings have an error, and there are also cases where timings cannot be accurately measured due to the influence of noise under a routine environment. In view of this, more robust blood pressure measurement can be performed by using a plurality of pulse wave propagation periods.

Presenting Section 106

See FIG. 1 again. The presenting section 106 presents blood pressure determined by the blood-pressure determining section 105. The presenting section 106 presents the blood pressure determined by the blood-pressure determining section 105 by displaying the determined blood pressure on a display screen. Note that the presenting section 106 corresponds to a first presenting section or a second presenting section.

Figure 10A:
FIG. 10A is a first explanatory diagram for explaining presentation of blood pressure in Embodiment 1.

FIG. 10A is a first explanatory diagram for explaining presentation of blood pressure in the present embodiment. As illustrated in FIG. 10A, the presenting section 106 presents "114 mmHg", which is the blood pressure determined by the blood-pressure determining section 105.

Figure 10B:
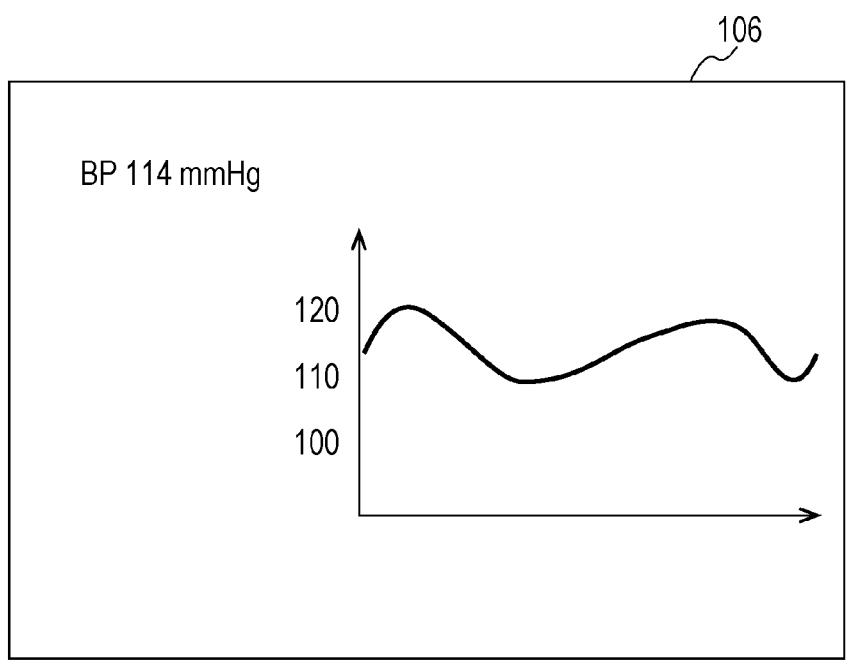
FIG. 10B is a second explanatory diagram for explaining presentation of blood pressure in Embodiment 1.

Note that the blood pressure continuously fluctuates. Therefore, the presenting section 106 may present a transition of the blood pressure. FIG. 10B is a second explanatory diagram for explaining presentation of blood pressure in the present embodiment. As illustrated in FIG. 10B, a time-series change of the blood pressure is shown as a graph in addition to "114 mmHg", which is the determined current blood pressure. The blood pressure markedly fluctuates due to various factors such as stress, smoking, awakening, and sleeping. It is therefore necessary to grasp not only blood pressure at a certain point in time, but also trend of blood pressure in order to maintain health. For example, even a person who usually has relatively low blood pressure may momentarily get high blood pressure, for example, under stress, during smoking, or at the time of awakening. This person himself or herself is not aware of this phenomenon. This is called masked hypertension and is becoming a problem in recent years. The non-contact blood-pressure measuring device 110 is a technique that makes it possible to measure blood pressure in a non-contact manner by using an image and a millimeter wave and to easily measure a transition of blood pressure, which continuously changes over passage of time. It is possible to maintain and promote health of a user by using a result of measurement by the non-contact blood-pressure measuring device 110.

An operation flow of the non-contact blood-pressure measuring device 110 according to the present embodiment described above is described below with reference to FIGS. 11, 12, and 13.

Figure 11:
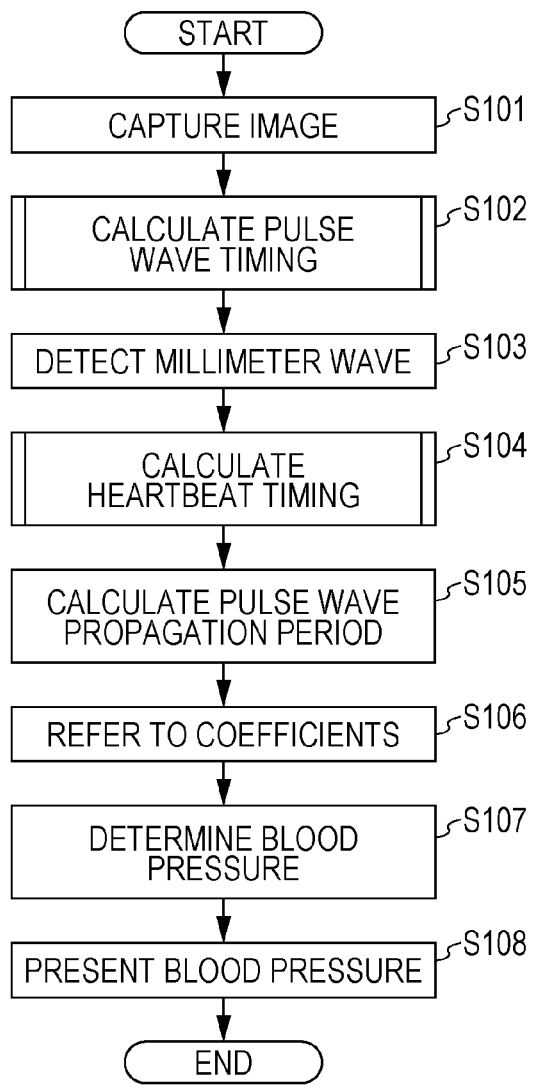
FIG. 11 is a flow chart illustrating flow of blood pressure measuring processing in the non-contact blood-pressure measuring device according to Embodiment 1.

FIG. 11 is a flow chart illustrating a flow of blood pressure measuring processing of the non-contact blood-pressure measuring device 110 according to the present embodiment.

First, the image acquiring section 101 captures a face image as a skin image (Step S101). Note that the image acquiring section 101 may acquire image data of a face image from another device or the like instead of capturing a skin image.

Next, the pulse-wave timing calculating section 102 calculates a pulse-wave timing on the basis of a change of luminance in the skin image captured by the image acquiring section 101 in Step S101 (Step S102).

Figure 12:
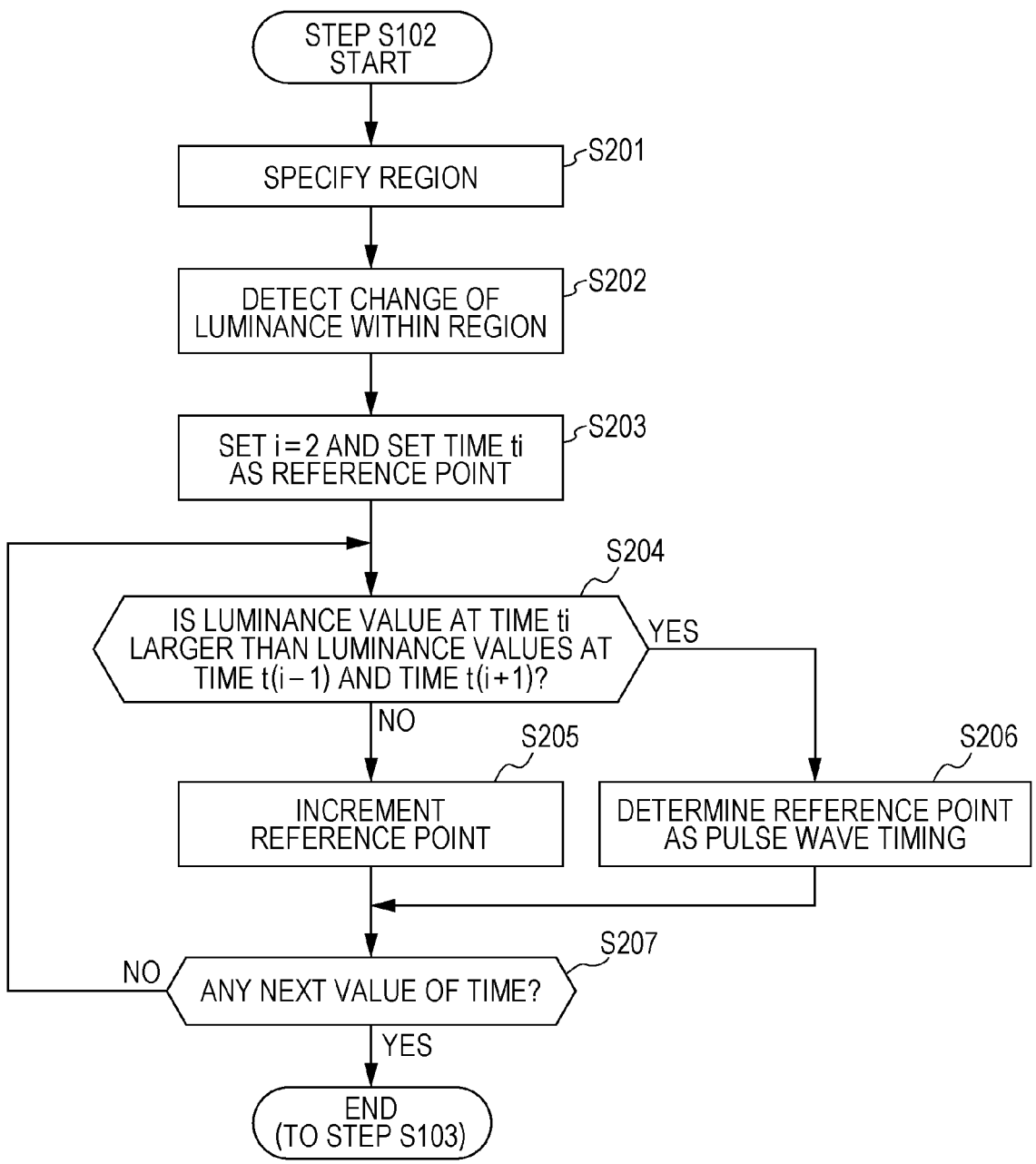
FIG. 12 is a first flow chart illustrating flow of details of the blood pressure measuring processing in the non-contact blood-pressure measuring device according to Embodiment 1.

FIG. 12 is a flow illustrating details of Step S102.

First, the pulse-wave timing calculating section 102 specifies a specific region, such as a cheek, where a change of luminance can be measured (Step S201).

The pulse-wave timing calculating section 102 calculates a change of the luminance in the region (Step S202).

The pulse-wave timing calculating section 102 calculates a pulse-wave timing by a method such as a peak search method. Specifically, the pulse-wave timing calculating section 102 sets i=2 and sets a time ti (i.e., time t2) as a reference point (Step S203). Note that i is a variable which is an index indicative of the reference point. The same applies hereinafter.

The pulse-wave timing calculating section 102 performs a comparison operation for comparing a luminance value at the time ti with a luminance value at a time t (i−1), which is one time point earlier than the reference point set in Step S203, and with a luminance value at a time t (i+1), which is one time point later than the reference point set in Step S203 (Step S204).

In a case where it is determined in Step S204 that the luminance value at the time ti is larger than both of the luminance value at the time t (i−1) and the luminance value at the time t (i+1) (Yes in Step S204), it is determined that the reference point is a local peak, and thus the reference point is specified as a pulse-wave timing (Step S206).

Meanwhile, in a case where it is determined in Step S204 that the luminance value at the time ti is smaller than any of the luminance value at the time t (i−1) and the luminance value at the time t (i+1) (No in Step S204), the index i indicative of the reference point is incremented (Step S207). Then, the luminance value at the incremented reference point is compared with a luminance value at a time which is one time point earlier than the reference point and a luminance value at a time which is one time point later than the reference point (return to Step S204). In a case where the reference point reaches a final point of the change of the luminance (Yes in Step S207), the processing returns to the main flow (to Step S103).

See FIG. 11 again. Next (or in parallel with capturing of the image), the millimeter-wave acquiring section 103 detects a millimeter wave (Step S103). Note that the millimeter-wave acquiring section 103 may acquire data of a millimeter wave from another device or the like instead of detecting a millimeter wave.

The heartbeat timing calculating section 104 calculates a heartbeat timing on the basis of a change of the phase of the detected millimeter wave (Step S104).

Figure 13:
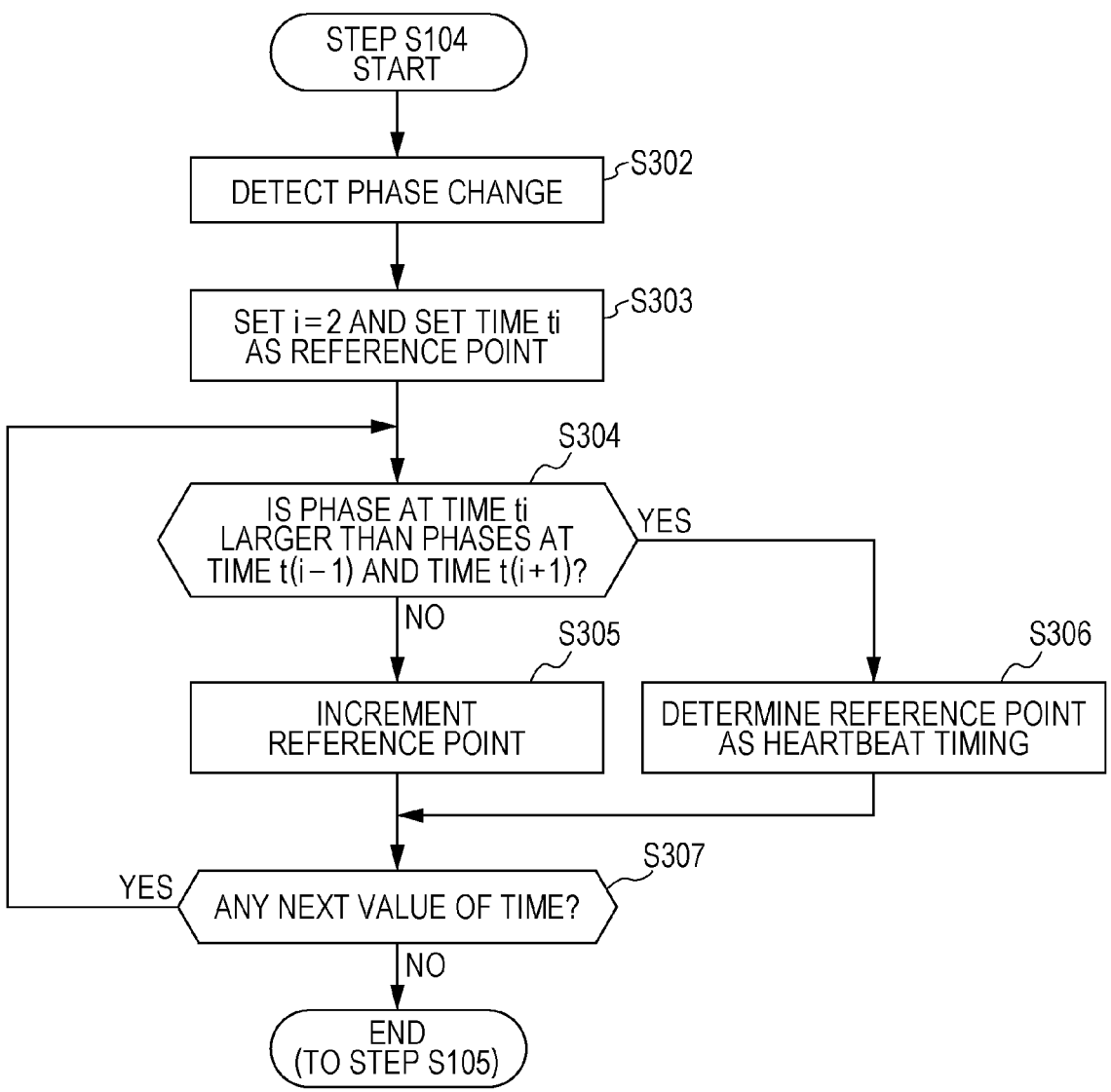
FIG. 13 is a second flow chart illustrating flow of details of the blood pressure measuring processing in the non-contact blood-pressure measuring device according to Embodiment 1.

FIG. 13 is a flow illustrating the details of Step S104.

First, the heartbeat timing calculating section 104 calculates a change of the phase of a wave reflected from a chest (Step S302).

The heartbeat timing calculating section 104 calculates a heartbeat timing by a method such as a peak search method. Specifically, the heartbeat timing calculating section 104 sets i=2 and sets a time ti (i.e., time t2) as a reference point (Step S303).

The heartbeat timing calculating section 104 performs a comparison operation for comparing a phase of the millimeter wave at the time ti with a phase of the millimeter wave at a time t (i−1), which is one time point earlier than the reference point set in Step S303, and with a phase of the millimeter wave at a time t (i+1), which is one time point later than the reference point set in Step S303 (Step S304).

In a case where it is determined in Step S304 that the phase of the millimeter wave at the time ti is larger than both of the phase of the millimeter wave at the time t (i−1) and the phase of the millimeter wave at the time t (i+1) (Yes in Step S304), it is determined that the reference point is a local peak, and thus the reference point is specified as a pulse-wave timing (Step S306).

Meanwhile, in a case where it is determined in Step S304 that the phase of the millimeter wave at the time ti is smaller than any of the phase of the millimeter wave at the time t (i−1) and the phase of the millimeter wave at the time t (i+1) (No in Step S304), the index i indicative of the reference point is incremented (Step S307). Then, a phase of the millimeter wave at the incremented reference point is compared with a phase of the millimeter wave at a time which is one time point earlier than the reference point and a phase of the millimeter wave at a time which is one time point later than the reference point (return to Step S304). In a case where the reference point reaches a final point of the signal whose phases changes (Yes in Step S307), the processing returns to the main flow (to Step S105).

See FIG. 11 again. The blood-pressure determining section 105 calculates a time difference (pulse wave propagation period) between the pulse-wave timing calculated by the pulse-wave timing calculating section 102 and the heartbeat timing calculated by the heartbeat timing calculating section 104 (Step S105).

The blood-pressure determining section 105 refers to parameters (the coefficients $\alpha$ and $\beta$) for determining blood pressure on the basis of the pulse wave propagation period (Step S106) and determines blood pressure (Step S107).

The presenting section 106 presents the determined blood pressure (Step S108).

Through the series of processing described above, the non-contact blood-pressure measuring device 110 can measure the blood pressure of a user.

Hereinafter, modifications of the constituent elements in the present embodiment are described.

Parameters (Models) of Blood-Pressure Determining Section

There are cases where the relation between a pulse wave propagation period and blood pressure differs from person to person and there are also cases where the relation between a pulse wave propagation period and blood pressure differs depending on the height, weight, body fat percentage, age, and the like. Furthermore, there are cases where the coefficients $\alpha$ and $\beta$ are relatively high for a user with high blood pressure. In view of this, an arrangement is also possible in which a plurality of models corresponding to these pieces of information, i.e., a plurality of sets of $\alpha$ and $\beta$ in the present example are stored, and a used model is switched among these models depending on an individual.

Figure 14:
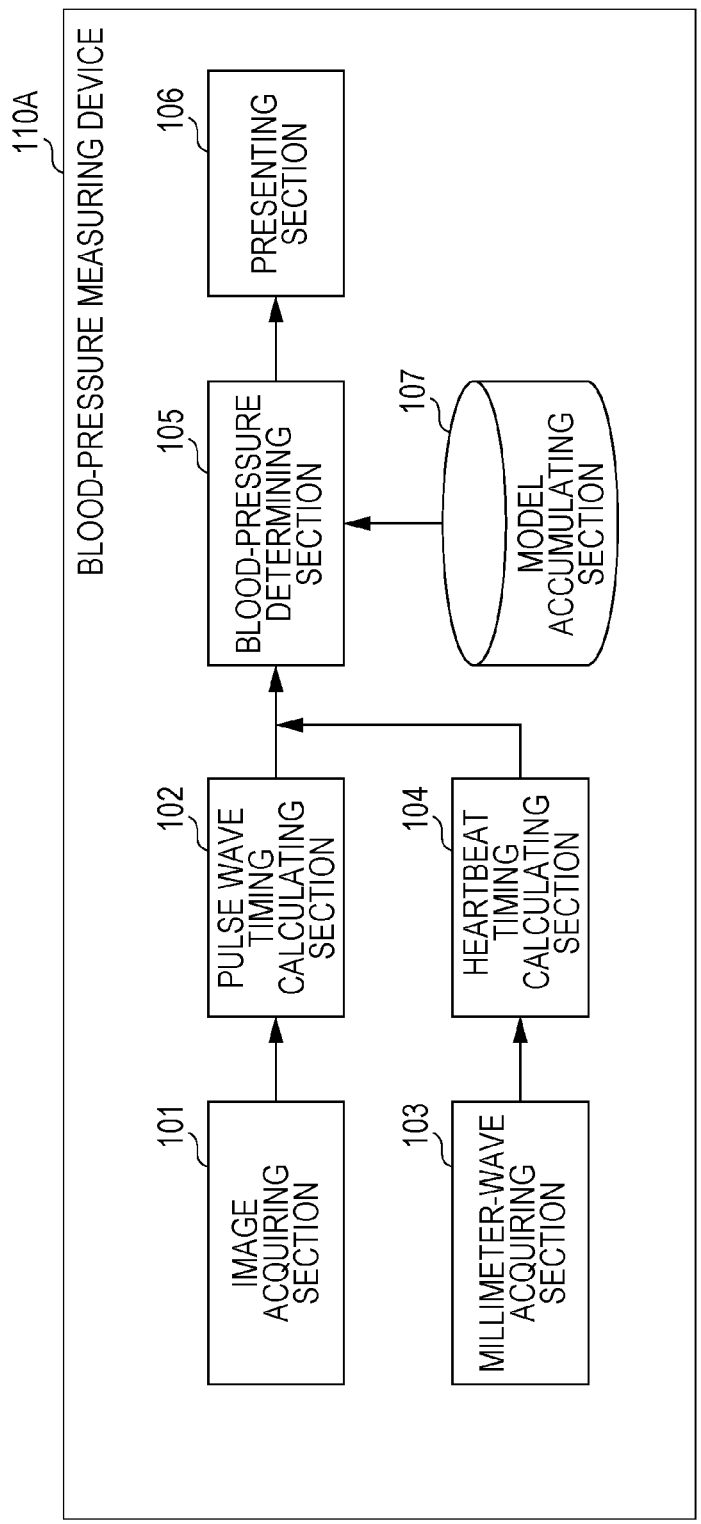
FIG. 14 is a second system configuration diagram of the non-contact blood-pressure measuring device according to Embodiment 1.

FIG. 14 is a second system configuration diagram of a non-contact blood-pressure measuring device according to the present embodiment (a second system configuration diagram of a non-contact blood-pressure measuring device 110A). The non-contact blood-pressure measuring device 110A includes a model accumulating section 107 in addition to the constituent elements of the non-contact blood-pressure measuring device 110.

The model accumulating section 107 accumulates therein models concerning a pulse wave propagation period used to determine blood pressure. In the present embodiment, the model accumulating section 107 accumulates therein values of the coefficients $\alpha$ and $\beta$.

FIG. 15 is an explanatory diagram for explaining an example of the models accumulated in the model accumulating section 107 of the present embodiment. The model accumulating section 107 accumulates therein a plurality of models. For example, assume that a user whose usual blood pressure is 139 mmHg or lower is a standard type. In the case of a standard type, a coefficient $\alpha$ of −0.8 and a coefficient $\beta$ of 250 are used. Furthermore, assume that a user whose usual blood pressure is 140 mmHg or higher is a high blood pressure type. In the case of a high blood pressure type, a coefficient $\alpha$ of −0.9 and a coefficient $\beta$ of 280 are used. These plurality of models are accumulated in the model accumulating section 107.

Figure 16:
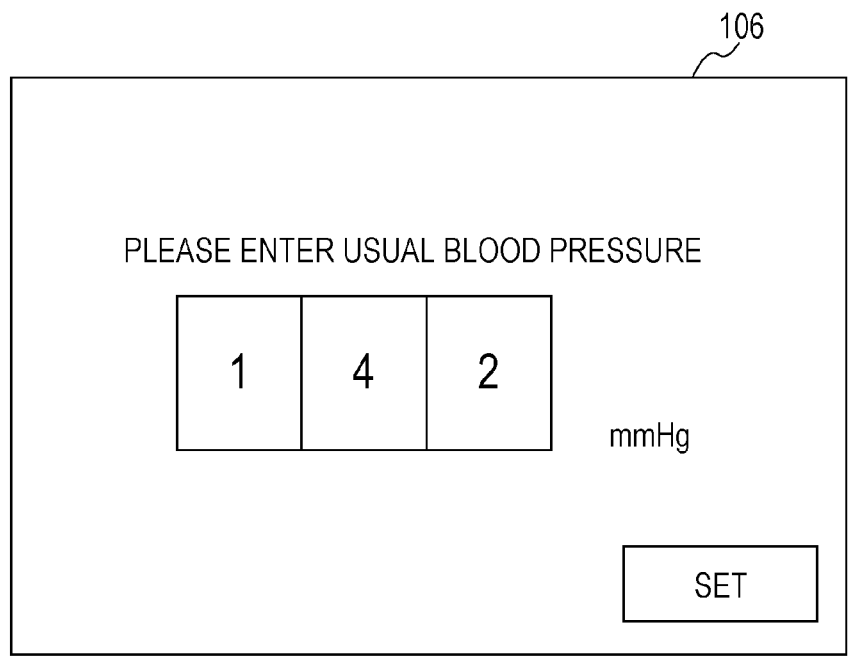
FIG. 16 is an explanatory diagram illustrating an example of setting of usual blood pressure in the non-contact blood-pressure measuring device according to Embodiment 1.

FIG. 16 is an explanatory diagram for explaining an example of setting of usual blood pressure in the non-contact blood-pressure measuring device 110A according to the present embodiment. In FIG. 16, "142 mmHg" has been input as setting of usual blood pressure. Therefore, blood pressure is determined on the basis of a pulse wave propagation period by using the coefficient $\alpha$ of −0.9 and the coefficient $\beta$ of 280, which are coefficients for the high blood pressure type.

Note that it is also possible to switch only the coefficient $\alpha$ by using usual blood pressure and newly calculate the coefficient $\beta$. For example, in the case of a user of the standard type whose usual blood pressure is 139 mmHg or lower as in FIG. 15, the coefficient $\alpha$ is set to −0.8, whereas in the case of a user of the high blood pressure type whose usual blood pressure is 140 mmHg or higher, the coefficient $\alpha$ is set to −0.9. Assume that 142 mmHg has been input as usual blood pressure and that the pulse wave propagation period calculated by the non-contact blood-pressure measuring device 110A is 170 milliseconds. In this case, the coefficient $\beta$ can be calculated as follows according to the expression (6): (142−170×(−0.9))=293. Hereinafter, the blood-pressure determining section 105 may determine blood pressure by using this coefficient.

Since there are differences among individuals in terms of determination of blood pressure based on a pulse wave propagation period, it is possible to more accurately determine blood pressure by adjusting parameters or models on the basis of usual blood pressure. Furthermore, since a pulse wave propagation period can be measured in a time-series manner, not only momentary blood pressure, but also a time-serial fluctuation of blood pressure can be easily measured. This makes it possible to easily measure continuously changing blood pressure. It is therefore possible to grasp the trend of blood pressure over passage of time, for example, it is possible to grasp the trend of annually increasing blood pressure. This leads to management of health and early detection of abnormality.

Note that the expression used to determine blood pressure is not limited to the expression (6) and can be a polynomial that takes parameters such as the weight and body fat percentage into consideration. Use of such a polynomial that takes parameters such as the weight and body fat percentage into consideration allows an improvement in accuracy of blood pressure measurement.

Note that the non-contact blood-pressure measuring device 110A may further include an accepting section (not illustrated) that accepts profile information including at least one of the height, weight, age, and blood pressure of a user. The blood-pressure determining section 105 may determine a candidate to be used to determine blood pressure from among candidates stored in the model accumulating section 107 on the basis of the profile information accepted by the accepting section and then determine blood pressure by using a relational expression including the determined candidate.

Note that switching of the coefficient $\alpha$ and $\beta$ by using models as described above is performed in Step S106 of FIG. 11. That is, in Step S106, the blood-pressure determining section 105 determines blood pressure by referring to the models (the coefficient α and β in the present example) accumulated in the model accumulating section 107.

Color Component, Target Region, Analysis Method, and Filter for Calculation of Pulse-Wave Timing Although a case where a pulse-wave timing is calculated by using G out of RGB has been described above, the present embodiment is not limited to this. A pulse-wave timing may be calculated by using R, B, or a combination of R, G, and B. For example, an independent component analysis method may be used in which an RGB signal is input and a pulse-wave timing is calculated on the basis of extracted signals. Since an image captured under a routine environment contains noise due to scattering light or various factors, a heartbeat component cannot always be calculated accurately on the basis of only a change of the luminance of G.

The independent component analysis method is a technique for, in a case where a plurality of input signals exist at different ratios in a plurality of sensors, stochastically separating and extracting the original input signals on the basis of the values of the plurality of sensors assuming that the input signals are independent. It can be considered that a pulse wave component is contained not only in G but also in R and B together with other noise. Therefore, the pulse wave component can be separated and extracted by using RGB by the component analysis method.

Figure 17:
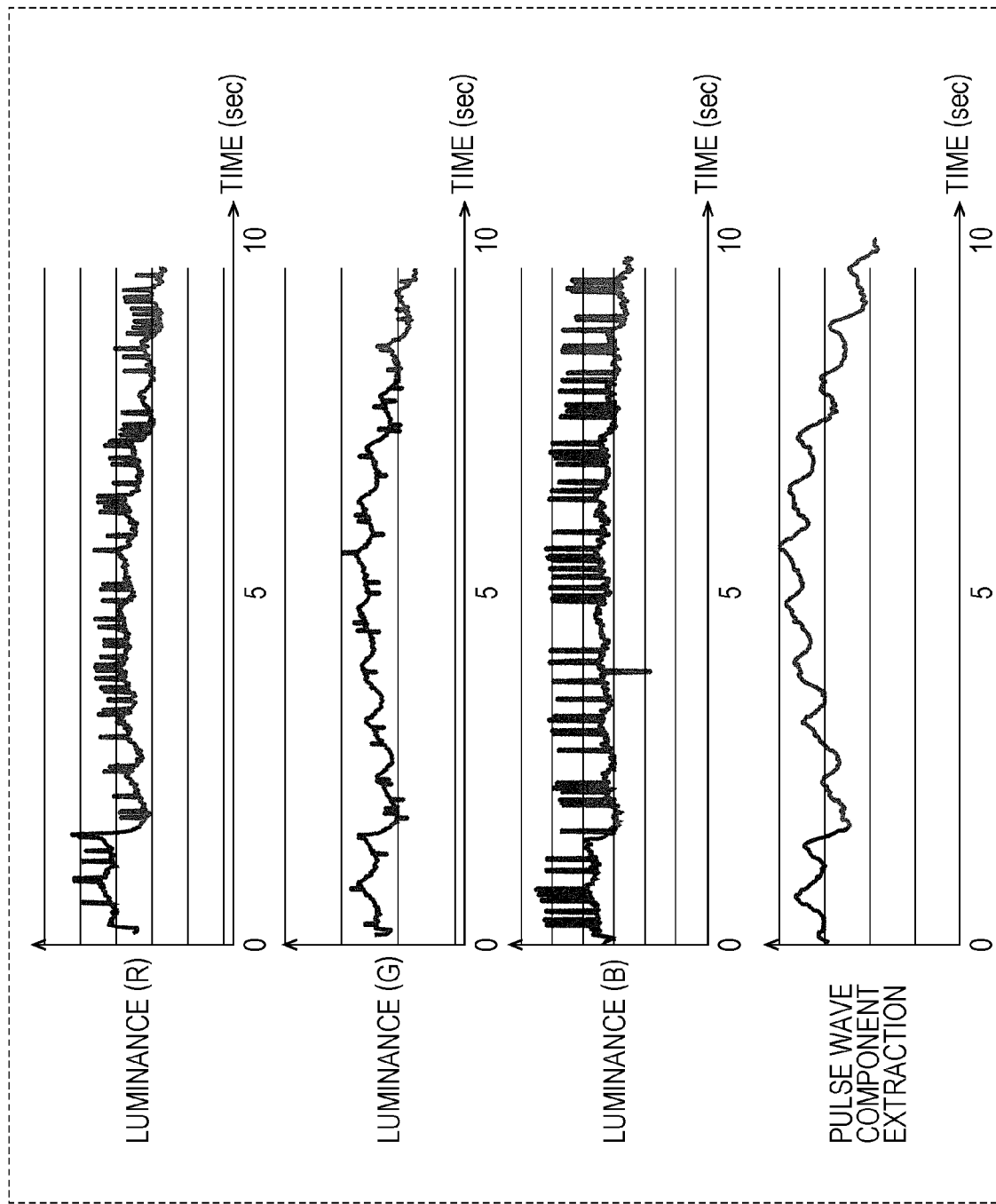
FIG. 17 is an explanatory diagram for explaining calculation of a pulse-wave timing in Embodiment 1.

FIG. 17 is an explanatory diagram for explaining calculation of a pulse-wave timing in the present embodiment. FIG. 17 is a diagram illustrating a change of the luminance of each of RGB in a cheek region of a face image obtained by capturing an actual face as in FIG. 3. In FIG. 17, the horizontal axis represents a time, and the vertical axis represents a change of luminance. The lowermost graph is a graph obtained by applying a low-pass filter to a signal obtained by using RGB by the independent component analysis method. As is clear from this graph, a periodical change caused by a pulse wave that is expressed as a change of luminance of each of RGB is accurately extracted.

The pulse-wave timing calculating section 102 may calculate a pulse-wave timing by using the signal of the extracted pulse wave component in the lowermost graph by a method such as a peak search method.

The pulse-wave timing calculating section 102 may extract a change of luminance caused by a pulse wave in a plurality of different regions (for example, a right cheek, a left cheek, and a forehead) of the face, where a change of luminance is likely to occur due to a pulse wave, by using a so-called statistical signal processing, such as independent component analysis or principal component analysis, and filtering.

In a case where the present device is used under a routine environment, there is a possibility that a captured image contain noise due to various factors such as scattering light and movement of a user. Therefore, the aforementioned method is effective, for example, in a case where a pulse-wave timing calculated by using only G is not accurate because of a large influence of noise.

Operation Example and IF

FIGS. 18A through 18D are explanatory diagrams for explaining information presented by the presenting section in the present embodiment.

Figure 18A:
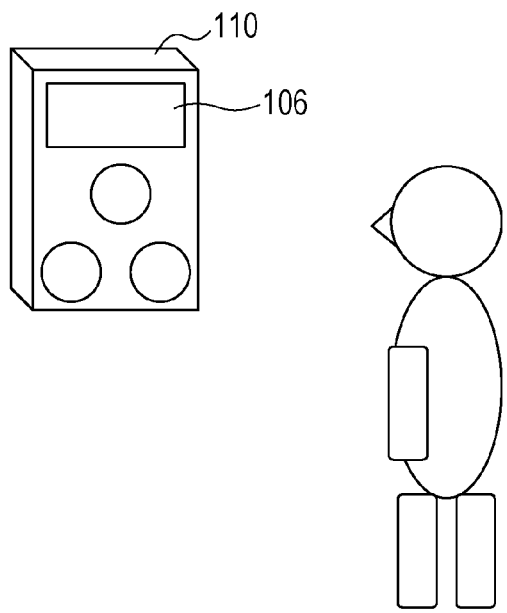
FIG. 18A is a first explanatory diagram for explaining presentation by a presenting section in Embodiment 1.

FIG. 18A illustrates the non-contact blood-pressure measuring device 110 and a user who faces the non-contact blood-pressure measuring device 110.

Figure 18B:
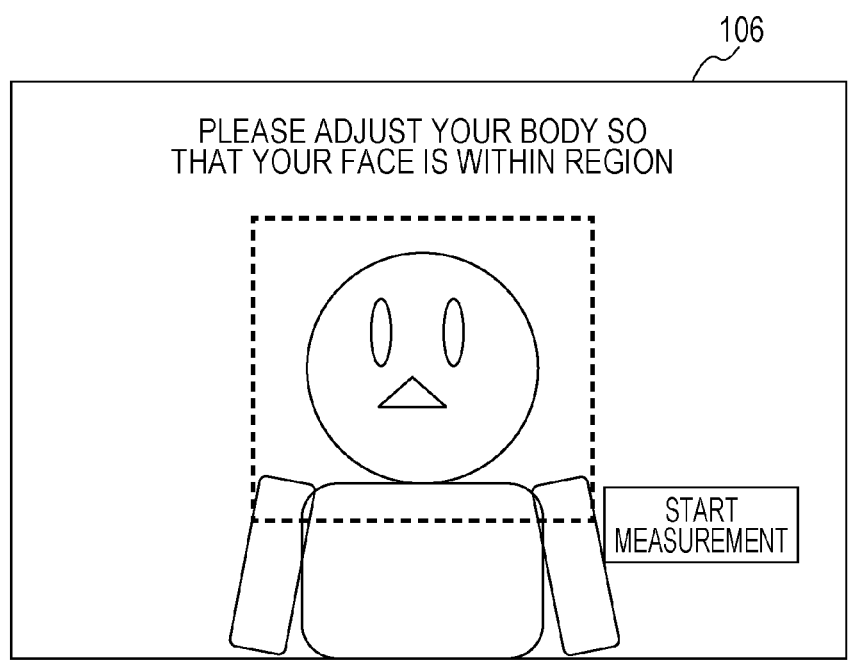
FIG. 18B is a second explanatory diagram for explaining presentation by a presenting section in Embodiment 1.

FIG. 18B illustrates contents displayed on a presentation screen. Specifically, in FIG. 18B, the face and chest of a user, a message, and a frame indicative of a region are displayed. The face and chest of the user are instantaneously displayed when an image of the face and chest of the user is acquired by the image acquiring section 101. The message and the frame indicative of a region are for prompting the user to adjust the body (the face and chest) of the user to an appropriate position. For example, first, a message such as "PLEASE ADJUST YOUR BODY SO THAT YOUR FACE IS LOCATED WITHIN THE REGION" is presented so as to prompt the user to be located at a predetermined position, angle, and region.

A pulse-wave timing can be more accurately detected on the basis of an image in a case where the luminance of a predetermined region of a face such as a cheek or a forehead is used. Therefore, more accurate detection of a pulse-wave timing is possible in a case where a frame indicative of a region is presented as illustrated in FIG. 18B so as to prompt the user to be located at a predetermined position. Furthermore, a heartbeat timing can be more accurately detected on the basis of a millimeter wave in a case where a signal reflected by a predetermined position such as a front chest is used. Therefore, more accurate detection of a heartbeat timing is possible in a case where a frame indicative of a region is presented as illustrated in FIG. 18B so as to prompt the user to be located at a predetermined position. Although an example in which a pulse wave is detected on the basis of the face image has been described above, a pulse wave may be detected on the basis of an image of another skin region, for example, by presenting a message such as "PLEASE PLACE YOUR HAND WITHIN THE REGION".

Figure 18C:
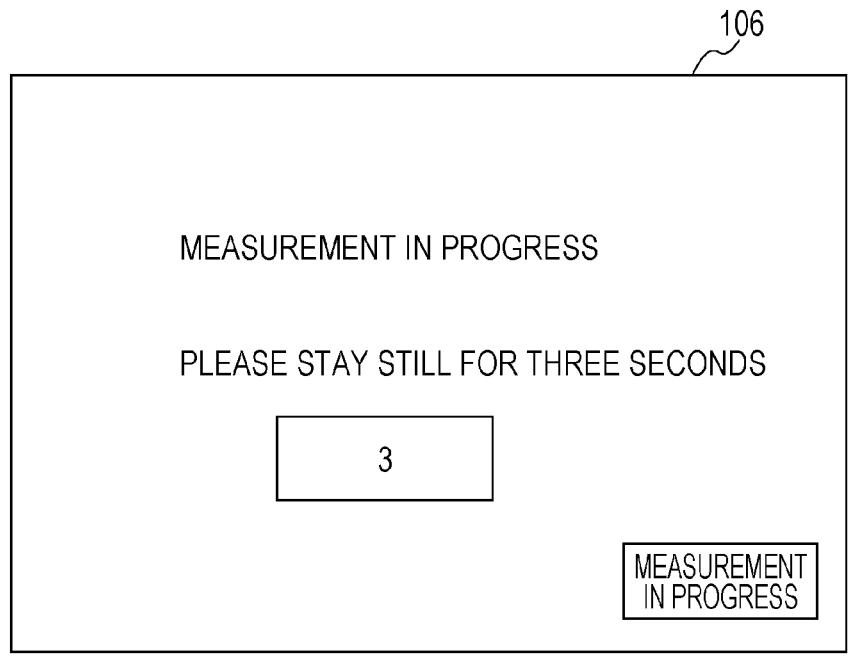
FIG. 18C is a third explanatory diagram for explaining presentation by a presenting section in Embodiment 1.
Figure 18D:
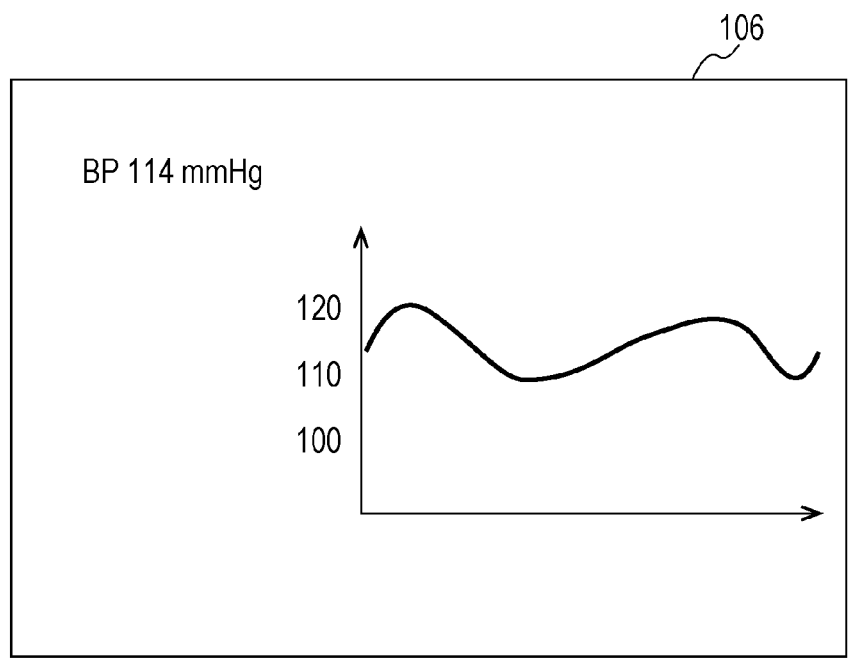
FIG. 18D is a fourth explanatory diagram for explaining presentation by a presenting section in Embodiment 1.

In FIG. 18C, a message "MEASURING IN PROGRESS" is presented in a case where the measurement start button of FIG. 18B is pressed. Note that an arrangement is also possible in which measurement automatically starts after elapse of a predetermined period from a point in time at which the user is located within the region. Since a pulse-wave timing based on an image and a heartbeat timing based on a millimeter wave are sometimes affected by various kinds of environment noise such as a change of light or body movement, it is sometimes desirable that the user stay still and be at rest in order to perform more accurate measurement. In view of this, a message such as "PLEASE STAY STILL FOR THREE SECONDS" that prompts the user to stay still is presented. In general, the rate of pulse waves and the rate of heartbeats are, for example, 80 bpm to 100 bpm. That is, at least one pulse wave and at least one heartbeat occur per second. This means that a pulse wave propagation period, which is needed to determine blood pressure, can be measured in approximately 1 second. In the present example, the message prompting the user to stay still for three seconds is presented because the average of several pulse wave propagation periods is used in consideration of an error and the accuracy. However, the present embodiment is not limited to this. In FIG. 18D, the measurement is finished, and it is determined as a result of the measurement that the blood pressure is "114 mmHg". Furthermore, since the non-contact blood-pressure measuring device 110 can also continuously measure a pulse wave propagation period in a time-series manner and thus measure blood pressure in a time-series manner, a time-series change of blood pressure is presented as a graph together with the current blood pressure.

Figure 19:
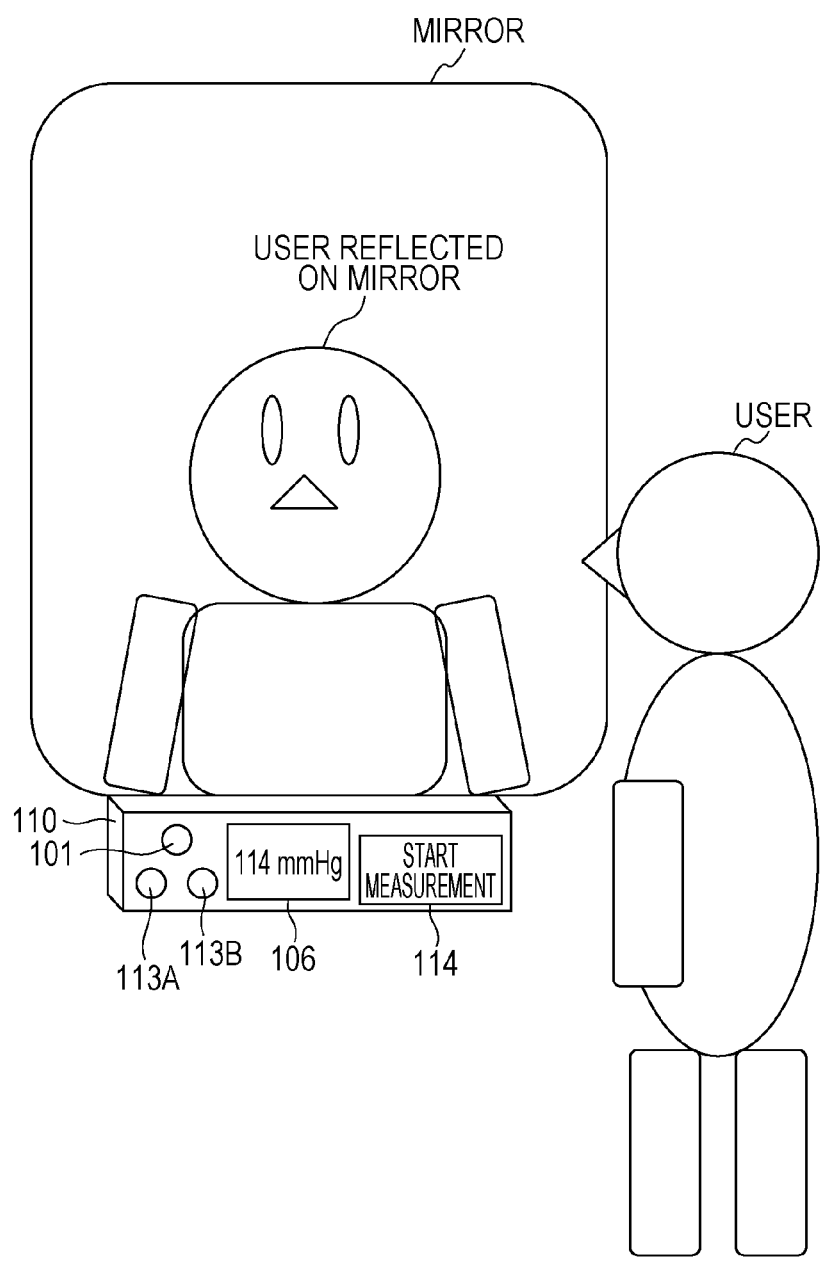
FIG. 19 is a second appearance diagram illustrating a non-contact blood-pressure measuring device according to Embodiment 1.

FIG. 19 is a second appearance diagram of the non-contact blood-pressure measuring device in the present embodiment. Specifically, FIG. 19 is a diagram illustrating an appearance of the non-contact blood-pressure measuring device 110 and an example of a scene of use of the non-contact blood-pressure measuring device 110. In FIG. 19, the non-contact blood-pressure measuring device 110 is provided below a general mirror. The non-contact blood-pressure measuring device 110 has, on the front side thereof, an image acquiring section, a receiving section that receives a millimeter wave, a transmitting section that transmits a millimeter wave, a presenting section that presents information, and an operation button for operating the device. Note that the non-contact blood-pressure measuring device 110 may be provided not below the mirror, but above the mirror, on the left of the mirror, or on the right of the mirror.

In general, a user often has opportunities to stand in front of a mirror in a washroom in daily life, for example, after awakening, before and after taking a bath, or after using a lavatory. In such situations, the user adjusts his or her clothes or recognizes his or her health condition such as a physical condition or the weight from his or her appearance in the mirror while facing the mirror (face-to-face with the mirror). In these situations, the user sometimes stays still and at rest relatively for a predetermined period of time. Such a state of the user is sometimes very suitable for detection of a heartbeat and a pulse wave by the non-contact blood-pressure measuring device 110. That is, very stable data with little noise can be easily acquired. Furthermore, some predetermined indoor spaces such as a washroom are space environments less affected by external scattering light, and therefore very stable data with little noise can be easily acquired in such indoor spaces. Therefore, the non-contact blood-pressure measuring device 110 may be installed in such an environment or may be used together with a mirror in such an environment.

For example, the non-contact blood-pressure measuring device 110 can be used in a manner such that a user presses the operation button in front of a mirror before or after taking a bath or when washing his or her face and thus measures his or her blood pressure in subsequent several seconds. Alternatively, an arrangement is also possible in which when a user stands in front of a mirror, the blood pressure is automatically measured by the non-contact blood-pressure measuring device 110. Since the non-contact blood-pressure measuring device 110 can very easily measure blood pressure in a non-contact manner, the blood pressure of a user can be routinely measured without placing a burden on the user. Furthermore, a behavior such as standing in front of a mirror provided in such an environment, for example, after awakening, when taking a bath, or when using a lavatory is a daily behavior. That is, it is possible to very easily and routinely measure blood pressure, for which it is said that daily regular measurement is important, without involving a user's complicated action or operation, thereby contributing promotion of user's health. Furthermore, the blood pressure can be easily measured every day in a relatively fixed time period such as before taking a bath. This makes it possible to perform measurement that is effective from the perspective of blood pressure measurement and health management.

It is said that blood pressure markedly changes before and after taking a bath or when urinating. Furthermore, it is medically said that some users temporarily get high blood pressure at the time of awakening or at early morning and that there is a correlation between early-morning high blood pressure and myocardial infarction. Since blood pressure continuously fluctuates, and not only a person with high blood pressure, but also a person with normal blood pressure sometimes rapidly develop high blood pressure, it is necessary from the perspective of health maintenance to grasp not only usual blood pressure, but also a time-series change of blood pressure.

By using the non-contact blood-pressure measuring device 110 as described above, it is possible to easily measure blood pressure at times when blood pressure changes such as early morning, before and after taking a bath, or after using a lavatory, thereby achieving effective health management of a user. Note that the usage example is not limited to this, and the non-contact blood-pressure measuring device 110 may be, for example, placed beside a bed, on a ceiling of a bedroom, or on a wall. This makes it possible to easily measure blood pressure during sleeping and at the time of awakening. Alternatively, the non-contact blood-pressure measuring device 110 may be placed or installed in a living room or close to a television set so that blood pressure of a user who is resting in the living room or watching TV is measured. In such a case where a user is resting in a living room or watching TV, the user, in some cases, is at rest or stays still, and the user's face and chest are, in many cases, facing the device. This increases the possibility that a signal which is less affected by noise can be measured, thereby making it possible to accurately measure blood pressure.

Figure 20A:
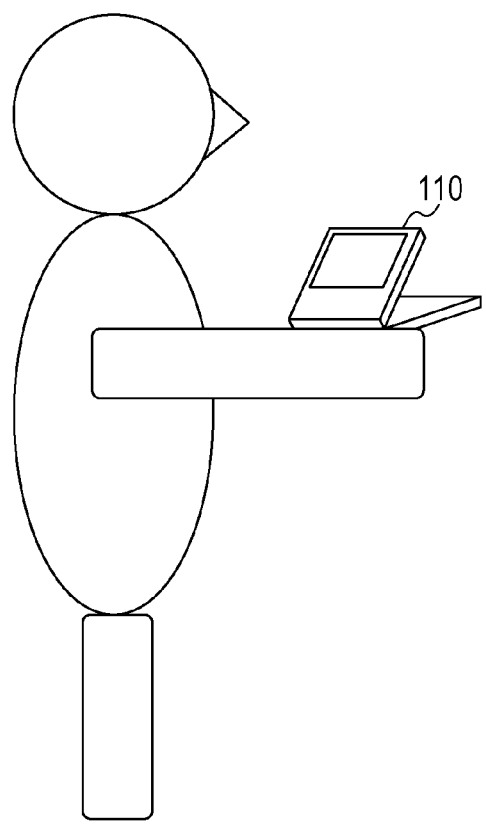
FIG. 20A is an explanatory diagram illustrating how the non-contact blood-pressure measuring device according to Embodiment 1 is used by a user.
Figure 20B:
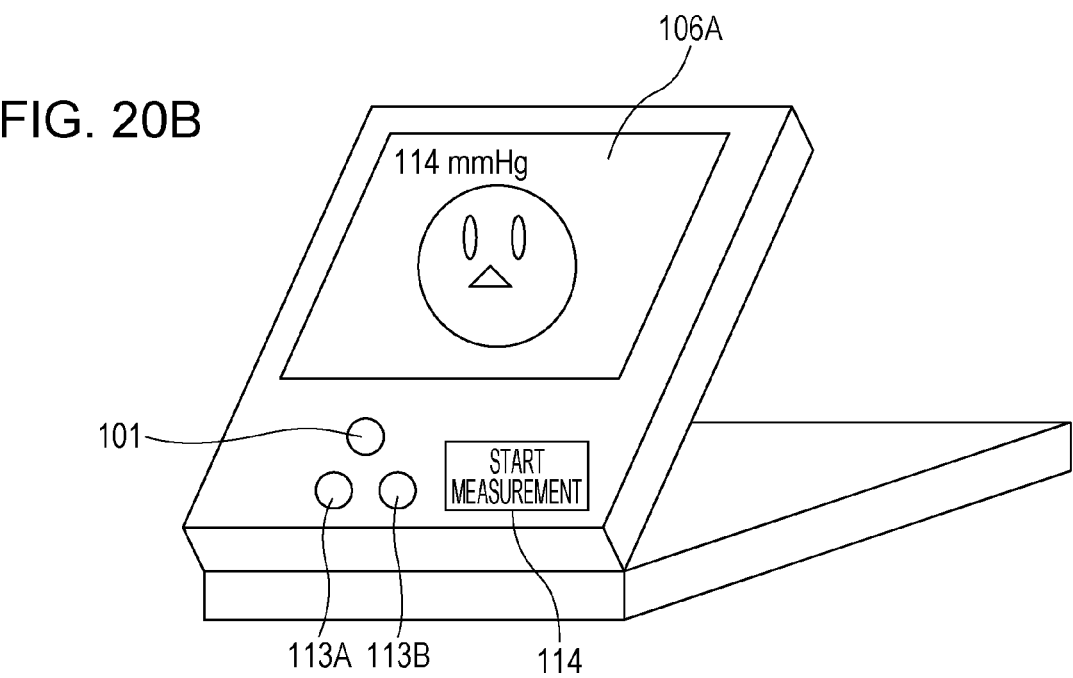
FIG. 20B is a second explanatory diagram of a second example of appearance of the non-contact blood-pressure measuring device according to Embodiment 1.

FIG. 20A is an explanatory diagram illustrating how the non-contact blood-pressure measuring device according to the present embodiment is used by a user. Although the appearance diagram of FIG. 19 illustrates a type of blood-pressure measuring device installed or placed indoors, the non-contact blood-pressure measuring device 110 may be a small portable type blood-pressure measuring device for measuring blood pressure when necessary. For example, a user may usually carry the non-contact blood-pressure measuring device 110 and routinely measure blood pressure by holding the non-contact blood-pressure measuring device 110 in his or her hand or placing the non-contact blood-pressure measuring device 110 at a predetermined position on a desk as illustrated in FIG. 20A. FIG. 20B illustrates an example of appearance of the non-contact blood-pressure measuring device 110. The non-contact blood-pressure measuring device 110 of FIG. 20B has, for example, a hand-mirror-shape and includes a presenting section 106A, an image acquiring section 101, a millimeter-wave acquiring section 103 including a transmitting section 113A and a receiving section 113B, an operation button 114, and the like. In a case where the presenting section 106A has a mirror (half mirror) therein, it is possible to switch between a mirror mode and a mode in which information is presented by the non-contact blood-pressure measuring device 110. With the arrangement, it is possible to easily measure blood pressure when necessary, thereby achieving daily health management.

It is also possible to employ an arrangement in which an image acquired by the image acquiring section 101 is presented on the presenting section 106A instantaneously (in real time) so that the image acquiring section 101 can be also used like a mirror, instead of using a physical mirror.

Modification 1 of Embodiment 1

In Embodiment 1, a non-contact blood-pressure measuring device that measures blood pressure by using information on subtle movement of a heart detected by a radar such as a millimeter wave and information on a subtle change of a color of a portion, such as a face or a hand, where skin is exposed has been described. In order to accurately measure blood pressure on the basis of these subtle signals, measurement needs to be performed during a period in which a change of a posture of a subject, especially a change of body movement of the chest is small. Furthermore, more accurate measurement of a change of blood flow is possible in a case where a change of a region used for measurement of a pulse wave, i.e., a portion where skin is exposed is smaller.

In view of this, in the present modification, a non-contact blood-pressure measuring device including a posture measuring section that measures a posture of a subject by using information of a visible image acquired by the image acquiring section 101 in addition to the system configuration of FIG. 1 is described. This blood-pressure measuring device controls a timing of measurement of a pulse wave propagation period by using posture information of the subject.

Figure 20C:
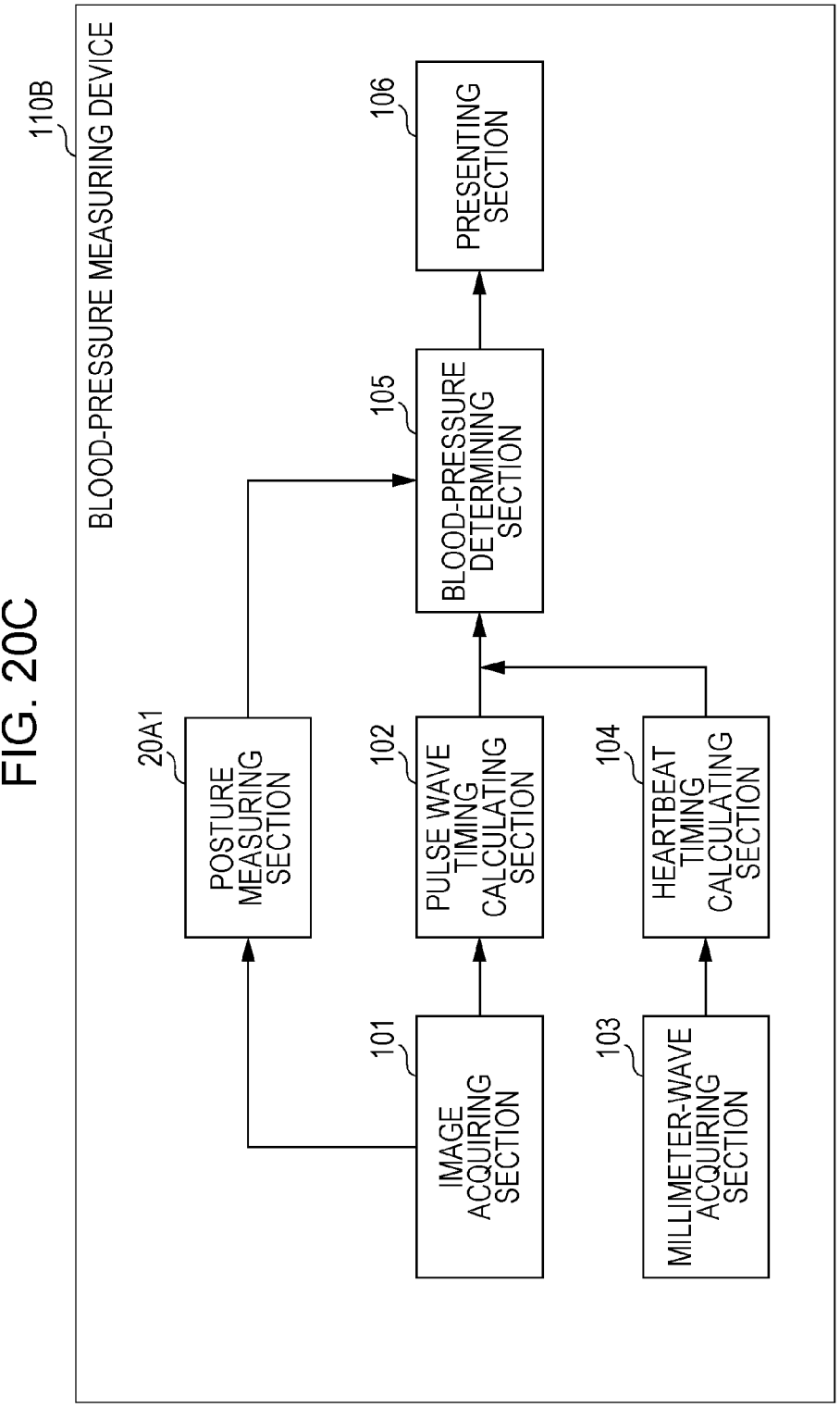
FIG. 20C is a block diagram illustrating a configuration of a non-contact blood-pressure measuring device according to Modification 1 of Embodiment 1.

FIG. 20C is a block diagram illustrating a configuration of a non-contact blood-pressure measuring device 110B according to the present modification. In FIG. 20C, operations of modules other than a posture measuring section 20A1 are similar to those in Embodiment 1, and detailed description thereof is omitted.

The posture measuring section 20A1 measures a posture of a user by measuring the amount of movement of each portion of the user on the basis of an image acquired by the image acquiring section 101. In particular, the posture measuring section 20A1 extracts regions such as a face region and a hand region where skin is exposed and a pulse wave can be measured and then measures the amount of movement in each of the regions. Furthermore, the posture measuring section 20A1 measures the amount of movement of an image of a chest region in order to measure movement of the heart (see FIG. 20D).

Then, the blood-pressure determining section 105 determines the blood pressure of the user on the basis of a time difference between (i) a pulse-wave timing calculated on the basis of a skin image acquired by the image acquiring section 101 during a period in which the amount of a change measured by the posture measuring section 20A1 is equal to or smaller than a predetermined threshold value and (ii) a heartbeat timing calculated on the basis of a radio wave acquired by the millimeter-wave acquiring section 103 during this period.

FIG. 20E is an explanatory diagram for explaining a method for determining a measurement timing in the present modification. FIG. 20E illustrates a time sequence of the amounts of movement of the respective regions within a predetermined period. The interval A in FIG. 20E is an example of an interval in which movement of the face is relatively small and movement of the chest region is relatively large. For example, during the interval A, the user is facing the front or in a certain direction but is moving his or her body. Alternatively, during the interval A, the user is not moving his or her body but is moving his or her arm so as to block the chest or move the chest accordingly. In this case, a pulse wave can be sometimes extracted on the basis of a face image, but, in many cases, a heartbeat timing cannot be accurately extracted because a signal of a millimeter wave reflected by the chest region is buried in noise. If blood pressure is measured by using the signal in this interval A, the measurement result is not always accurate. This sometimes causes misunderstanding of the user. This is very unpractical for the user.

Meanwhile, the interval C in FIG. 20E is an example of an interval in which movement of the chest region is small, but movement of the face is relatively large. For example, during the interval C, the user is staying still on a sofa, in front of a mirror, in front of a television set, or in a room such as a bedroom but is jerking his or her head this way or that or is chatting so that a skin region of the face is moving accordingly. In this case, a heartbeat can be sometimes extracted on the basis of a signal of a millimeter wave reflected by the chest region, but a heartbeat timing cannot be accurately extracted because a pulse wave, which is detected on the basis of a face image, is buried in noise. As in the interval A, the measurement result is not always accurate in the interval C. This sometimes causes misunderstanding of the user. This is very unpractical for the user.

In contrast to these intervals, the interval B is an example of an interval in which both of movement of the chest region and movement of the skin region are relatively small. For example, it is possible to employ an arrangement in which a threshold value is set for the amount of movement of each region, and blood pressure is measured in a case where both of the movement of the chest region and the amount of movement of the skin region are equal to or smaller than the respective threshold values. With the arrangement, it is possible to accurately measure blood pressure. Alternatively, it is also possible to employ an arrangement in which blood pressure is measured in the background, and the blood pressure is displayed for the user in a case where the amount of movement of each region is equal to or smaller than a threshold value.

In particular, assuming that the non-contact blood-pressure measuring device 110B is used under a routine environment, a period in which both of a skin region such as the face of the user and the chest of the user are still is limited. However, since the non-contact blood-pressure measuring device 110B is capable of measuring blood pressure on the basis of several (at least one) time differences, it is unnecessary for the user to stop movement of the face and chest for a long period. With the present arrangement, it is possible to accurately measure blood pressure by extracting a period of time in which the amounts of movement of the portions needed for measurement of blood pressure are small although each region of the subject is moving and then measuring blood pressure by using a pulse wave propagation period obtained during this period of time.

A pulse-wave timing calculating section can extract a timing of a pulse wave with relatively high accuracy by tracking the position of the skin region even in a case where the user is moving his or her body. Meanwhile, a change by a heartbeat that appears in a millimeter wave is very small and is therefore susceptible to slight movement of the body and noise. Therefore, in many cases, the pulse-wave timing is more accurate, and the heartbeat timing is more inaccurate. In view of this, a heartbeat timing calculating section may calculate a timing of a heartbeat on the basis of a pulse-wave timing.

Specifically, the heartbeat timing calculating section may calculate a heartbeat timing included in a predetermined time range determined on the basis of a pulse-wave timing. The predetermined time range is a time range before the pulse-wave timing. The predetermined time range is, for example, a time range of not less than 50 ms to not more than 300 ms before the pulse-wave timing.

A time range before a pulse-wave timing is used because a heartbeat occurs in accordance with movement of the heart, and then a pulse wave reaches a portion such as the face of the user.

Processing of the heartbeat timing calculating section is described below with reference to FIG. 9. In FIG. 9, a pulse-wave timing (t3) has been calculated. The pulse-wave timing (t3) is considered accurate, and a heartbeat timing (h3) included in a predetermined period before the pulse-wave timing (t3) is specified.

The heartbeat data illustrated in FIG. 9 is data with little noise. However, a millimeter wave signal that is actually measured includes a lot of peaks that are not heartbeat timings due to slight movement of the user, breathing of the user, or noise. By obtaining a peak caused by a heartbeat on the basis of a timing of a pulse wave, it is possible to reduce the risk of erroneous detection of a peak. That is, use of a timing of a pulse wave increases the possibility that a peak caused by a heartbeat can be detected from among a lot of peaks. As a result, it is possible to detect a heartbeat timing with high accuracy without being affected by movement of the user, noise, and the like.

In a case where movement of the heart is measured by using a Doppler effect of a millimeter wave as in the present embodiment, it is preferable that the measurement be performed during a period in which forward and backward body movement of the user is small. This is because contracting and expanding movement of the heart is more evident in the forward-backward direction of the chest.

Figure 20F:
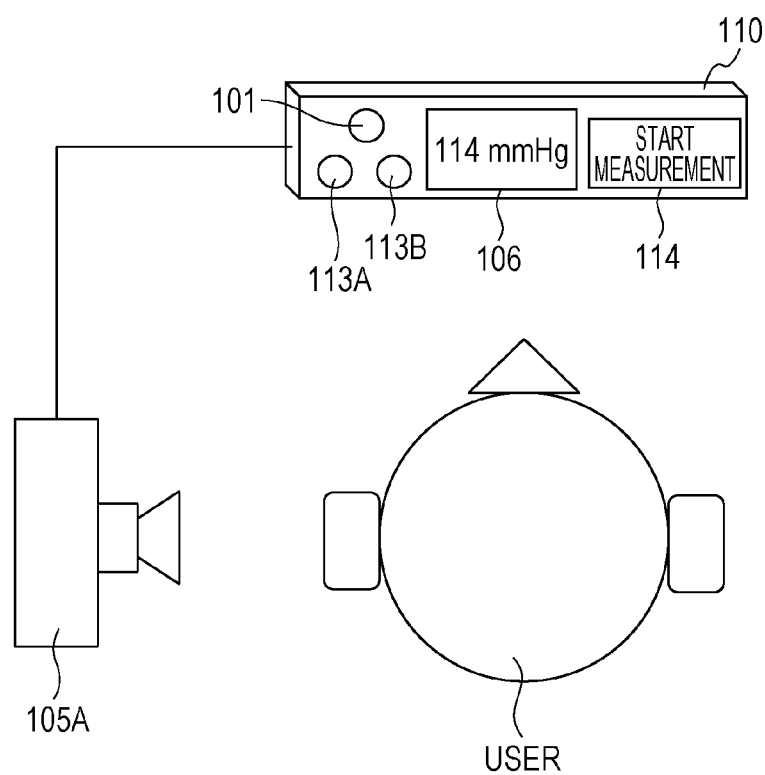
FIG. 20F is an explanatory diagram illustrating an image-capturing section for posture fluctuation measurement in Modification 1 of Embodiment 1.

In view of this, it is preferable that an acquiring section for posture measurement 105A, which is an image-capturing section that measures a posture from the side of the user as illustrated in FIG. 20F, be provided in order to accurately detect forward and backward body movement of the user which becomes noise. That is, body movement is detected from the side of the user, and blood pressure is measured in a case where the body movement is small as in FIG. 20E. Meanwhile, an image used for measurement of a pulse wave can be any image of a portion where user's skin is exposed and therefore can be a captured image of a side of the user's face. It is therefore possible to achieve more accurate measurement by employing the arrangement in which a direction in which a millimeter wave for measurement of the heart is transmitted and received and a direction in which an image of the user is captured by the acquiring section for posture measurement 105A are orthogonal to each other as illustrated in FIG. 20F.

Although FIG. 20F illustrates a case where the user's body faces the millimeter-wave acquiring section and where the camera is provided on the side of the user's body, it is also possible to employ an arrangement in which the millimeter-wave acquiring section is provided on the side of the user's body and where the user's body is facing the camera. That is, a direction in which the millimeter-wave acquiring section receives a millimeter wave and a direction in which an image is captured by the camera are orthogonal to each other.

Figure 20G:
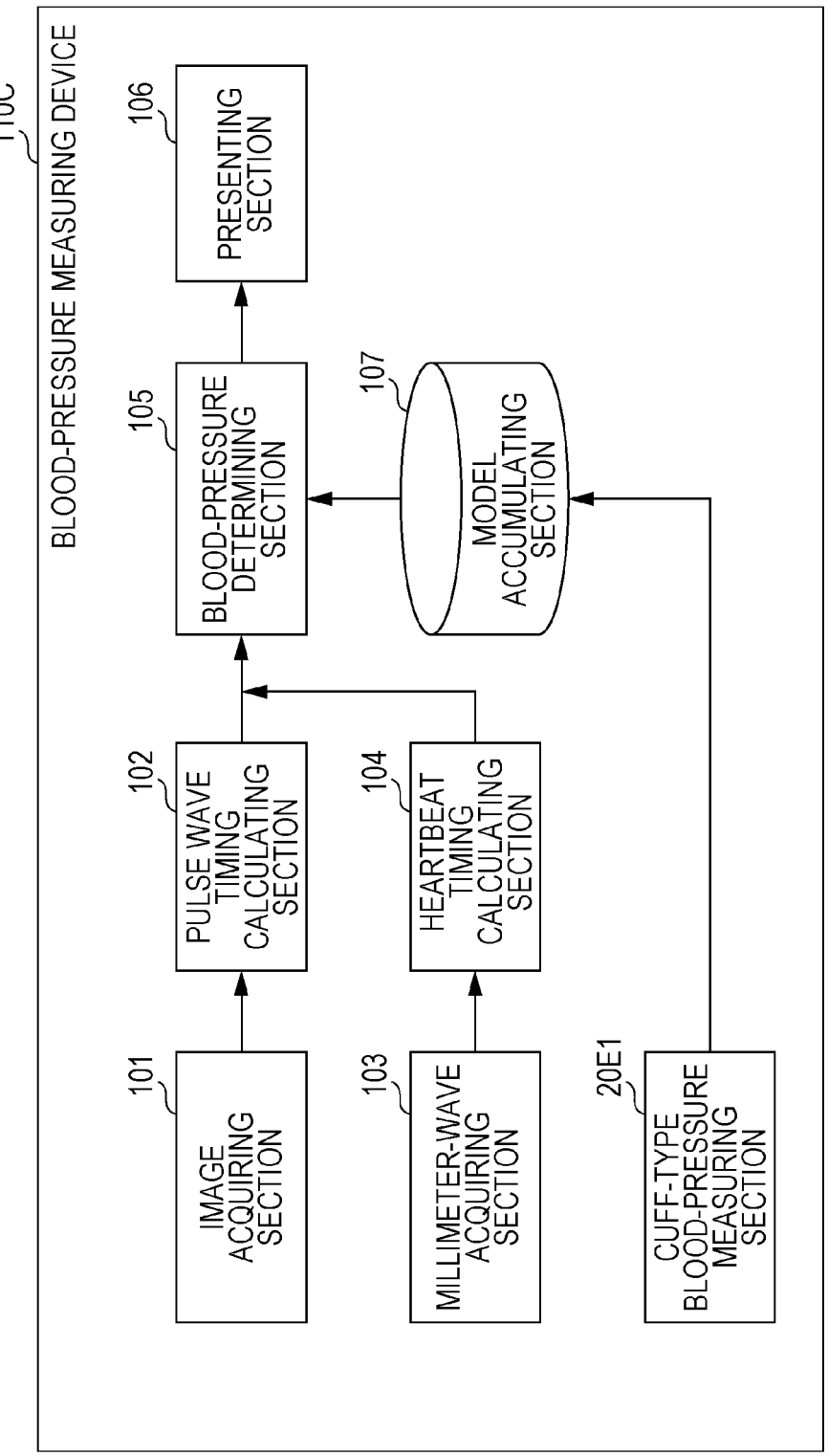
FIG. 20G is a block diagram illustrating a configuration of a non-contact blood-pressure measuring device according to Modification 2 of Embodiment 1.
Figure 20I:
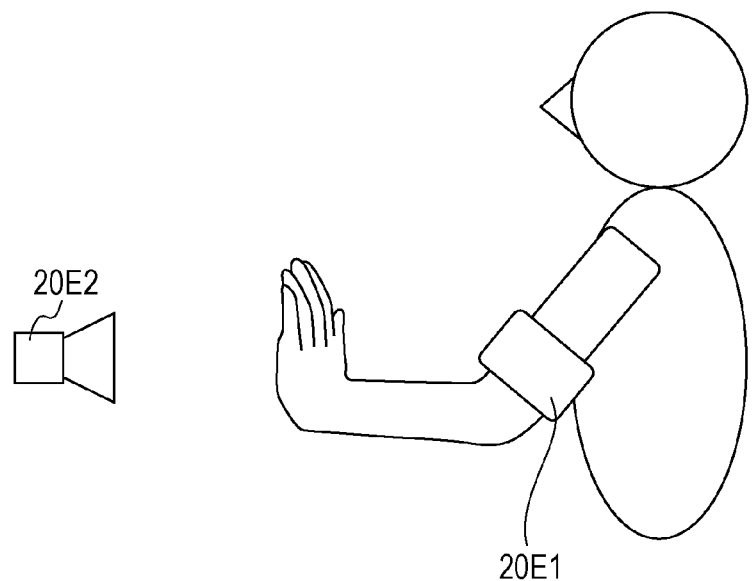
FIG. 20I is a schematic view illustrating an example of how a non-contact blood-pressure measuring device according to Modification 2 of Embodiment 1 is used by a user.
Figure 20J:
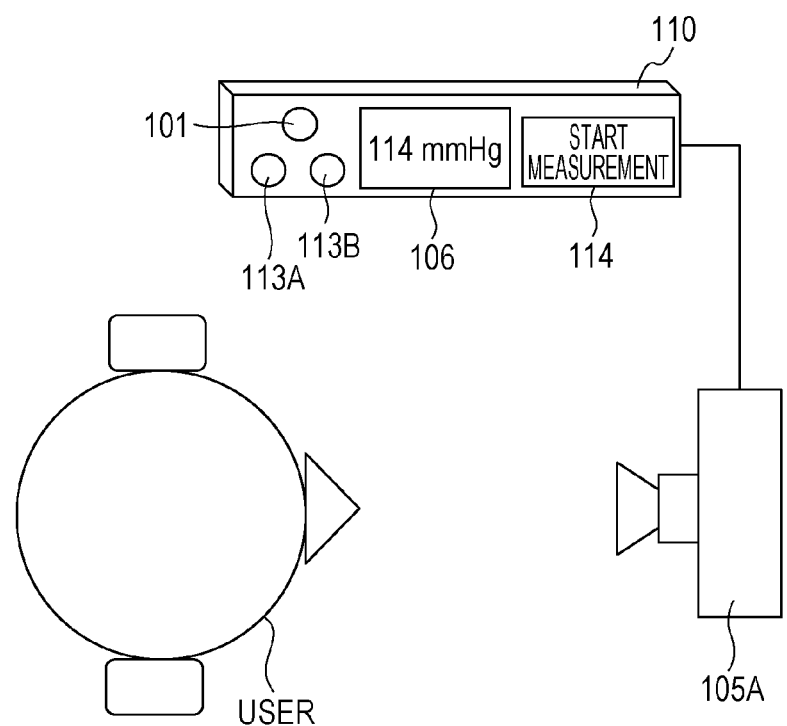
FIG. 20J is a schematic view illustrating an example of how a non-contact blood-pressure measuring device according to Modification 2 of Embodiment 1 is used by a user.

FIG. 20J illustrates an example in which the millimeter-wave acquiring section is provided on the side of the user's body and the user's body is facing the camera.

For example, the millimeter-wave acquiring section and the camera may be disposed on the basis of the presenting section 106. The presenting section 106 has a display surface on which information is presented to the user.

In FIGS. 20F and 20J, the millimeter-wave acquiring section is arranged such that a millimeter wave receiving section is disposed to receive a millimeter wave in a direction perpendicular to the presentation surface, and the camera captures an image in a direction parallel with the presentation surface.

Pulsation in the vicinity of the chest caused by a beat of the heart can be detected not only from the front direction, but also from the side or from an oblique direction, for example. In particular, large movement of the chest or the abdomen occurs in the front direction of the body due to breathing. Therefore, by detecting a heartbeat from the side or from an oblique direction, it is possible to more accurately detect a pulsation caused by a beat of the heart while suppressing the influence of breathing.

Meanwhile, in a case where large movement of the body occurs in a forward-backward direction with respect to a millimeter wave (in this case, sideways movement for the user), it is difficult to detect the body movement by using a millimeter wave. In this case, a heartbeat timing may be detected from a millimeter wave in a case where sideways movement (forward-backward direction for the millimeter wave) is small by detecting movement of the user by using the camera that faces the user. Alternatively, a heartbeat timing detected in a case where sideways movement is small may be preferentially used as a heartbeat timing with high reliability. This makes it possible to perform more accurately measurement.

Note that a direction in which the millimeter-wave acquiring section 103 transmits and receives a millimeter wave and a direction in which the acquiring section for posture measurement 105A captures an image may be any directions that are not identical to each other and need not necessarily be orthogonal to each other. That is, the acquiring section for posture measurement 105A for measuring a posture need not necessarily be disposed on the side of the user and may be disposed, for example, diagonally in front of the user or diagonally from behind the user.

It is desirable that a signal of a heartbeat measured by a millimeter wave be measured from the left side of the user where the heart is closer. This is because the left side of the user is closer to the heart of the user.

Furthermore, it is desirable that a millimeter wave be measured from an oblique direction or from the side of the user in order to suppress a component caused by breathing.

Figure 20K:
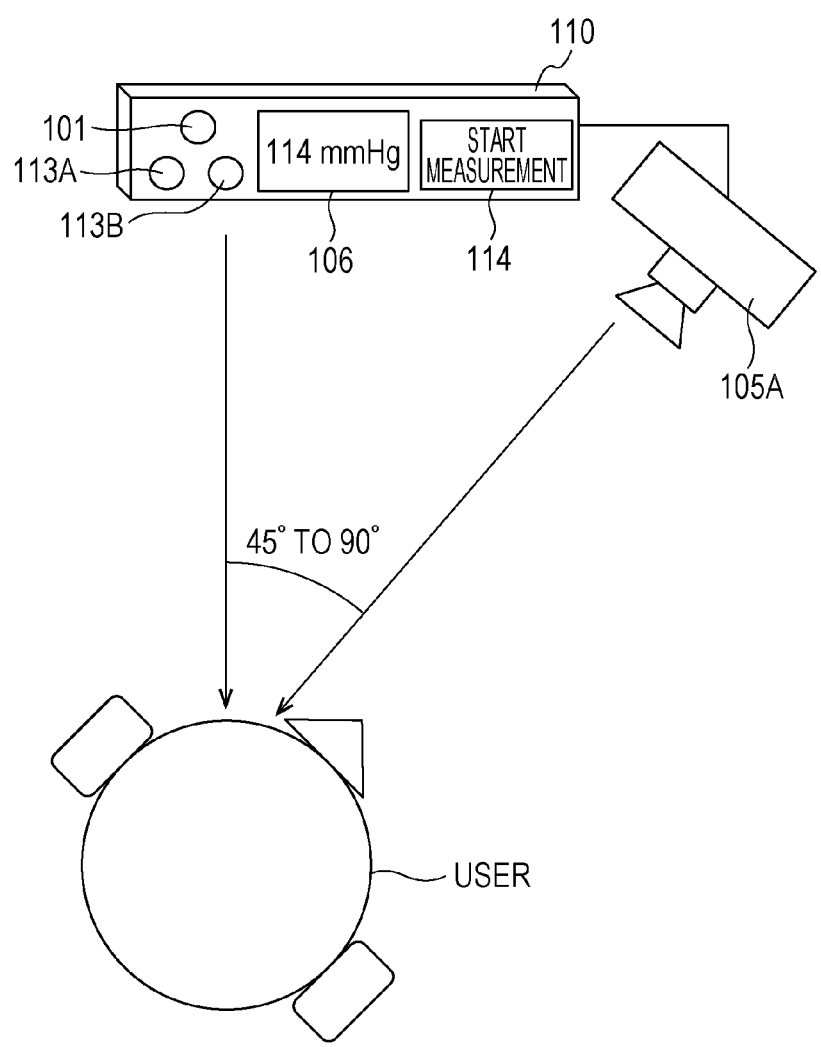
FIG. 20K is a schematic view illustrating an example of how a non-contact blood-pressure measuring device according to Modification 2 of Embodiment 1 is used by a user.

In a case where a pulse wave is detected on the basis of an image, it is desirable that the image be captured from the front direction in which measurement of a skin region of the face is easier. In view of this, the millimeter-wave acquiring section 103 and the acquiring section for posture measurement 105A may be disposed, for example, within a range from 45 degrees to 90 degrees as illustrated in FIG. 20K. That is, it is possible to employ an arrangement in which the millimeter wave receiving section is disposed so as to receive a millimeter wave in a direction orthogonal to the display surface, and the camera is disposed so as to capture an image at an angle of 45 degrees with respect to the direction orthogonal to the display surface.

Modification 2 of Embodiment 1

The non-contact blood-pressure measuring device 110 of Embodiment 1 determines, for each individual, a variable for determining blood pressure on the basis of user's usual blood pressure entered by the user as illustrated in FIG. 16. In order to further increase the accuracy of blood pressure, it is desirable that movement of the user's heart and a pulse wave during measurement of blood pressure by a cuff-type device for measuring blood pressure (cuff-type blood pressure measurement) be measured.

FIG. 20G is a block diagram illustrating a configuration of a non-contact blood-pressure measuring device according to the present modification.

A non-contact blood-pressure measuring device 110C according to the present modification includes a cuff-type blood pressure measuring section 20E1 in addition to the system configuration of FIG. 1. When calculating coefficients for each individual, the non-contact blood-pressure measuring device 110C determines parameters accumulated in a model accumulating section 107 by using a value measured by the cuff-type blood pressure measuring section 20E1. Note that the non-contact blood-pressure measuring device 110C may use, as parameters, standard coefficients calculated by using results of cuff-type blood pressure measurement performed for a plurality of persons.

FIG. 20H is an explanatory diagram for explaining a timing at which parameters are determined in the present modification. In FIG. 20H, the horizontal axis represents a time, and (a), (b), and (c) are a timing of a heartbeat, a timing of a pulse wave, and a timing at which parameters are determined, respectively.

In general, in a cuff-type blood pressure measurement method, blood flow of an arm is stopped by using a cuff, and then blood pressure is measured by using a pulsation (pulse wave) of a blood vessel wall that occurs in the process of depressurizing the cuff. In the process of depressurizing the cuff, the pulse wave rapidly rises at a certain point in time. Then, the pulse wave rapidly declines, and from a certain point in time, the pulse wave does not change much anymore. The pressure of the cuff at the point in time at which the pulse wave rapidly rises is referred to as a maximum blood pressure (systolic blood pressure), and the pressure of the cuff at the point in time at which the pulse wave becomes unchanging is referred to as a minimum blood pressure (diastolic blood pressure).

In view of this, parameters are determined by using a pulse wave propagation period between a timing t_high at which the maximum blood pressure after the start of depressurization of the cuff is measured and a timing t_low at which the minimum blood pressure is measured. Specifically, parameters are determined by using a timing h3 of a heartbeat and a timing t3 of a pulse wave between the timing t_high and the timing t_low. This makes it possible to more accurately determine parameters suitable for each individual.

In the above description, parameters are determined by using a heartbeat and a pulse wave between t_high and t_low. However, it is also possible that parameters be determined on the basis of timings that are relatively close to the above timings. In other words, the blood-pressure determining section 105 may determine predetermined parameters included in the expression (6) on the basis of (i) a time difference determined on the basis of a pair of pulse-wave and heartbeat timings included in a period from a first timing, which is a timing at which the maximum blood pressure is measured by the cuff-type blood pressure measuring section 20E1, to a second timing, which is a timing at which the minimum blood pressure is measured by the cuff-type blood pressure measuring section 20E1, (ii) a time difference determined on the basis of a pair of pulse-wave and heartbeat timings that is closest to the first timing, and (iii) a time difference determined on the basis of a pair of pulse-wave and heartbeat timings that is closest to the second timing, among pairs of pulse-wave and heartbeat timings that correspond to each other.

FIG. 20I is a schematic view illustrating an example of how the non-contact blood-pressure measuring device according to the present modification is used by a user.

In the cuff-type blood pressure measurement method, in many cases, blood pressure is measured by attaching a cuff to an upper arm of a user. In view of this, in order to further improve the accuracy of measurement, an image acquiring section 101 may acquire a skin image of a portion, such as a palm, that is located anterior to the cuff-type blood pressure measuring section (a portion pressing the arm of the user) as illustrated in FIG. 20I. By thus measuring blood flow of the portion, such as a palm, that is located anterior to the cuff-type blood pressure measuring section on the basis of the image, it is possible to further improve the accuracy of measurement.

Embodiment 2

In the present embodiment, a non-contact blood-pressure measuring device that improves accuracy of a heartbeat timing obtained from a millimeter wave by using an acquired image is described.

Figure 21:
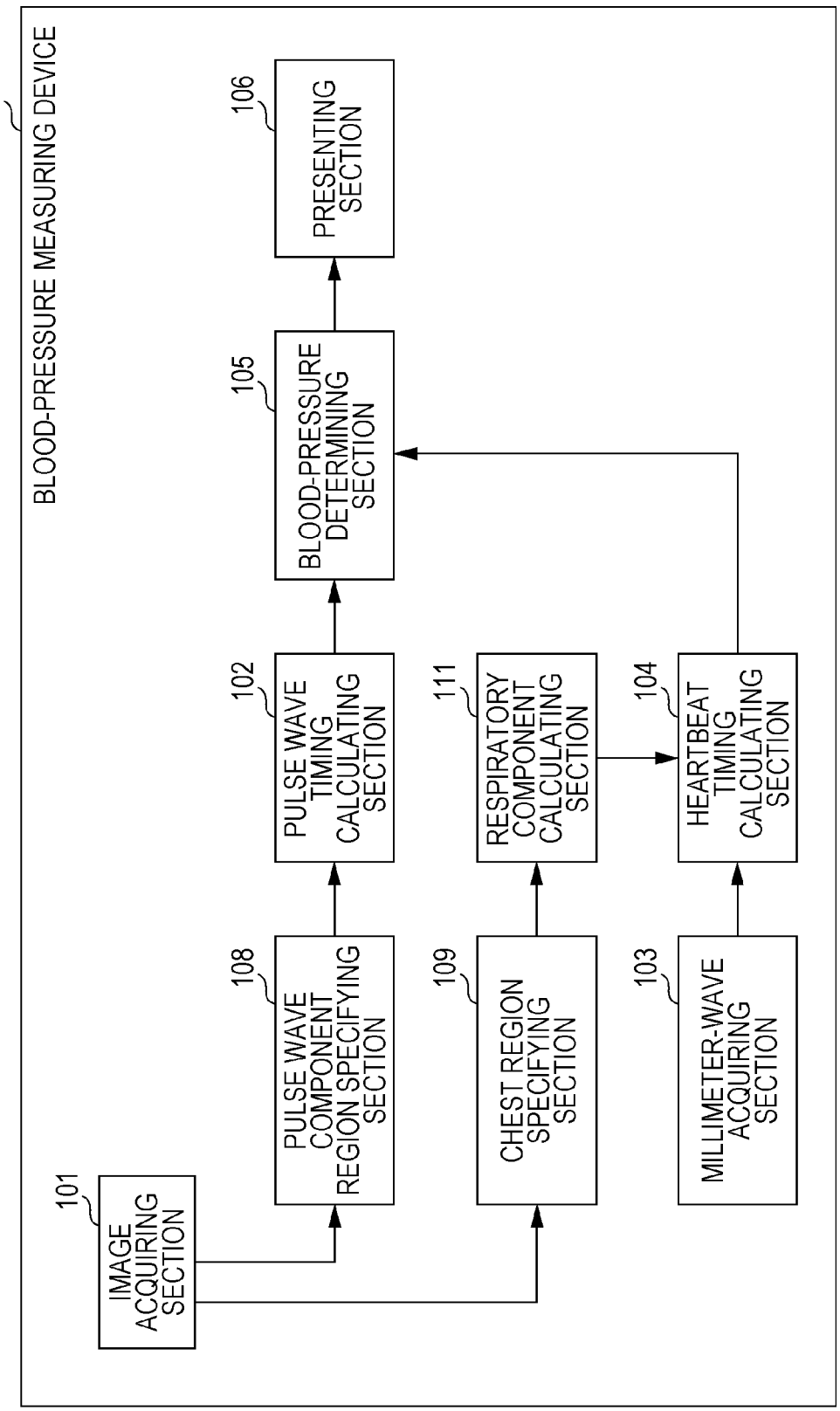
FIG. 21 is a block diagram illustrating a configuration of a non-contact blood-pressure measuring device according to Embodiment 2.

FIG. 21 is a block diagram illustrating a configuration of a non-contact blood-pressure measuring device according to the present embodiment.

A non-contact blood-pressure measuring device 110 includes a pulse wave component region specifying section 108, a chest region specifying section 109, and a respiratory component calculating section 111 in addition to the constituent elements of Embodiment 1.

The pulse wave component region specifying section 108 specifies a region, such as a face, a forehead, or a cheek, for calculation of a pulse-wave timing in an image captured by an image acquiring section 101 such as a camera.

Figure 22A:
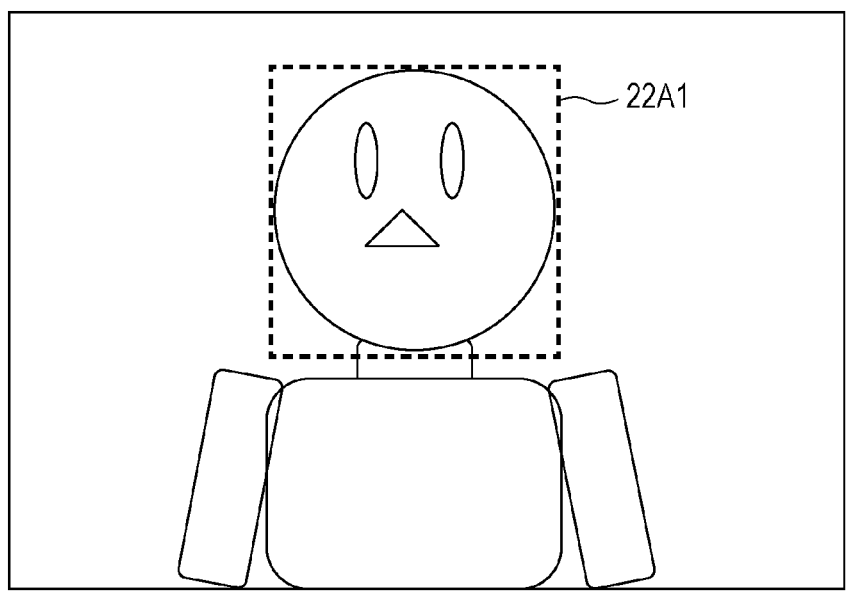
FIG. 22A is a first explanatory diagram for explaining processing for specifying a pulse wave component region in the non-contact blood-pressure measuring device according to Embodiment 2.
Figure 22B:
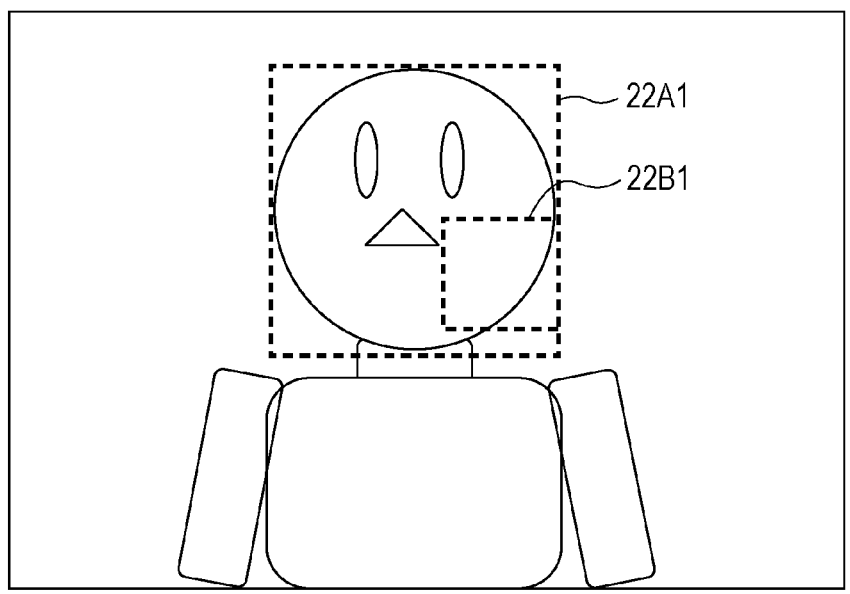
FIG. 22B is a second explanatory diagram for explaining processing for specifying a pulse wave component region in the non-contact blood-pressure measuring device according to Embodiment 2.

FIGS. 22A and 22B are explanatory diagrams for explaining processing for specifying a pulse wave component region in the non-contact blood-pressure measuring device according to the present embodiment. The processing for specifying the region is described with reference to FIG. 22A. FIG. 22A illustrates an image captured by the image acquiring section 101. In the present embodiment, a case where a cheek, which is one of regions where a change of luminance is likely to occur due to a pulse wave, is used as a region in which a pulse wave component is extracted is described.

The pulse wave component region specifying section 108 specifies a region of the face from the captured image. Note that various pattern recognition techniques such as a face recognition technique using Harr-like feature points are known as a face recognition technique, and details of a face recognition technique used in the present embodiment is not limited in particular. In FIG. 22A, the specified face region is indicated by the broken-line frame 22A1.

The pulse wave component region specifying section 108 specifies, as a cheek region, a predetermined region (for example, a lower right quarter) from the face region. In FIG. 22B, the specified cheek region is indicated by the broken-line frame 22B1. Note that in a case where a forehead is used, it is, needless to say, possible to change a region in which a pulse wave component is extracted by changing the position and the size of the specified region (for example, an upper quarter). Alternatively, color spectrum information may be used instead of a specific portion such as a forehead or a cheek. In this case, a flesh-color region may be extracted from the whole face. Alternatively, a combination of the specific region and the flesh-color region may be used. This makes it possible to extract a pulse wave in accordance with a user's state irrespective of a direction of the face.

The pulse-wave timing calculating section 102 calculates a timing of a pulse wave on the basis of a change of the luminance in the image as in Embodiment 1. In the present modification, the pulse-wave timing calculating section 102 calculates a timing of a pulse wave by using the region specified by the pulse wave component region specifying section 108. This processing is similar to that in Embodiment 1, and therefore description thereof is omitted.

The chest region specifying section 109 specifies a chest region from the image captured by the image acquiring section 101.

Figure 23A:
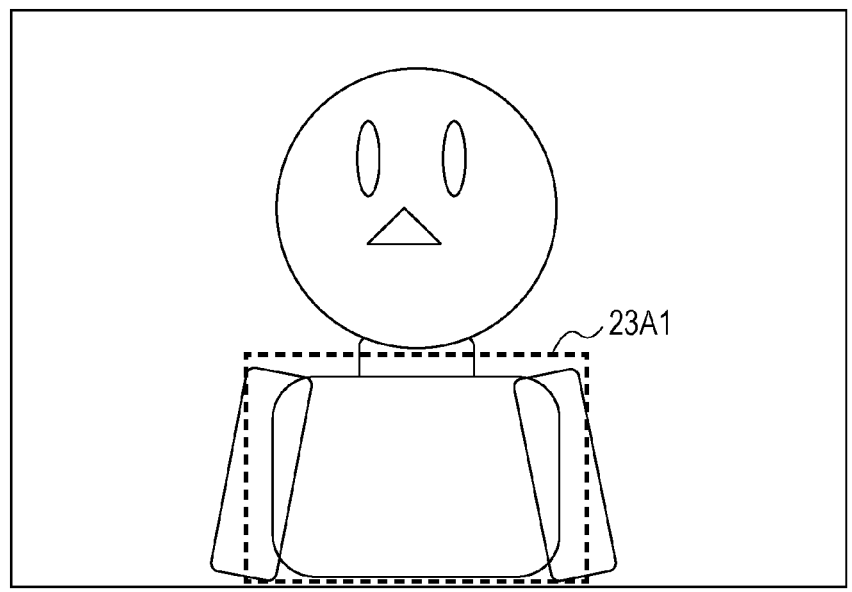
FIG. 23A is a first explanatory diagram for explaining processing for specifying a chest region in the non-contact blood-pressure measuring device according to Embodiment 2.
Figure 23B:
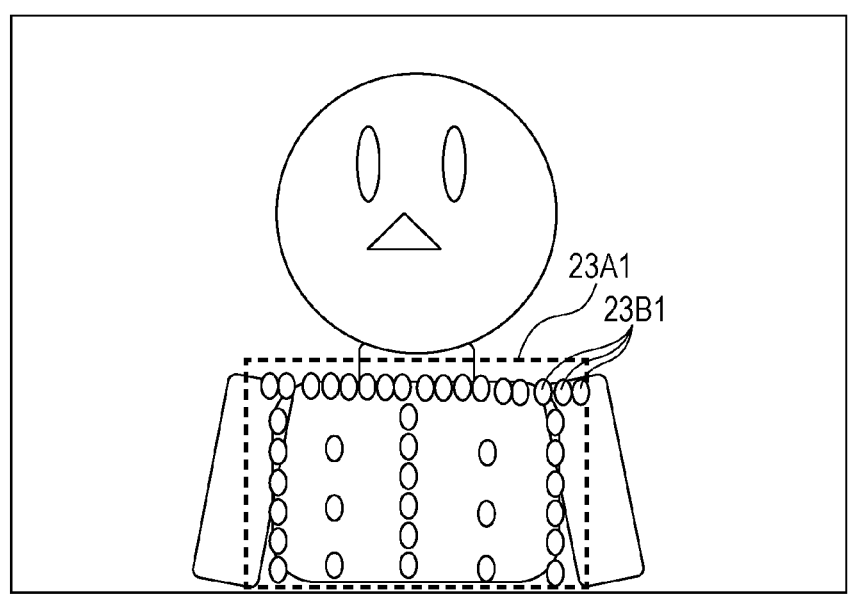
FIG. 23B is a second explanatory diagram for explaining processing for specifying a chest region in the non-contact blood-pressure measuring device according to Embodiment 2.

FIGS. 23A and 23B are explanatory diagrams for explaining processing for specifying a chest region in the non-contact blood-pressure measuring device according to the present embodiment.

FIG. 23A is a diagram for explaining processing for specifying a chest region. FIG. 23A illustrates a captured image as in FIG. 22A. For example, a predetermined region (for example, a region that is below the face region and is two times as wide as the width of the face region and ½ times as long as the length of the face region) is specified as the chest region on the basis of the specified face region. In FIG. 23A, the specified chest region is indicated by the broken-line frame 23A1.

The respiratory component calculating section 111 calculates a respiratory component by using an image within the region specified by the chest region specifying section 109. For example, the respiratory component calculating section 111 calculates a respiratory component by using optical flows of predetermined feature points within the chest region. The optical flow feature points obtained within the chest region are indicated by the white circles 23B1.

An optical flow is a concept expressing, as a vector, the magnitude and direction of movement of predetermined feature points, a group of feature points, or a predetermined object in a time-series image such as a moving image. As a method for extracting feature points, various methods such as a Lucas-Kanade method are known. Features are arbitrarily selected or automatically selected by using a predetermined threshold value or parameter indicative of adequacy as feature points such as trackability (i.e., obtainability of corresponding points on a next image).

For example, in the case of an image of the chest of a person as illustrated in FIG. 23B, a boundary between the background and the person (in a case where the person is wearing a cloth, a boundary between the background and the cloth) and, because of the influence of environment light, especially a shoulder part are automatically obtained as feature points. Furthermore, in a case where the person is wearing a cloth, feature points are often automatically obtained on lines along a seam and a crease, a part specific to a design (for example, on a line along a body shape of the chest in a case where the person is wearing a striped shirt), a button part, and the like. By using the optical flows of these feature points, the respiratory component calculating section 111 calculates a respiratory component.

Figure 24A:
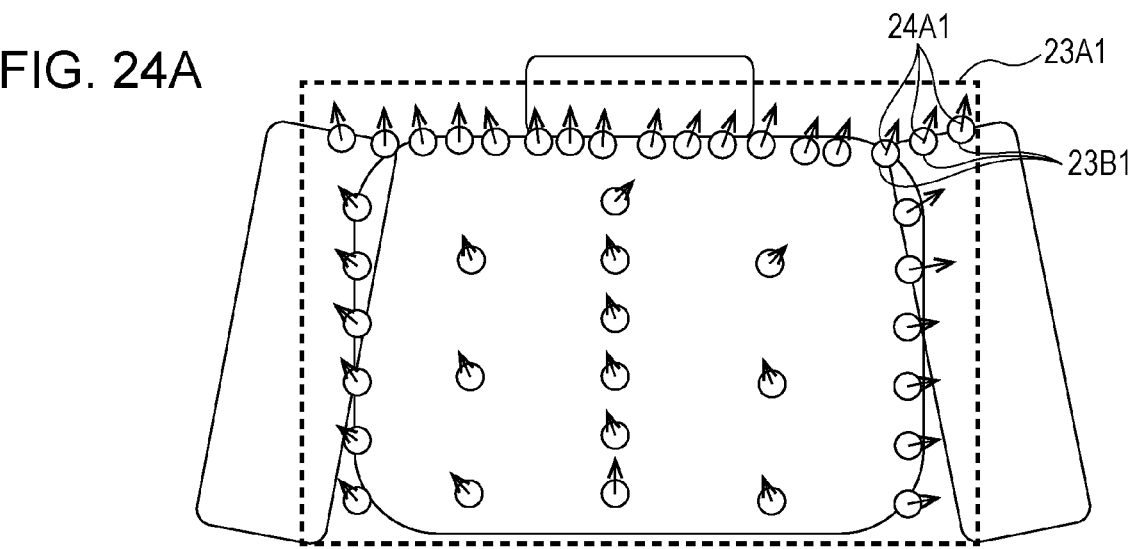
FIG. 24A is a first explanatory diagram for explaining calculation of a respiratory component in the non-contact blood-pressure measuring device according to Embodiment 2.
Figure 24B:
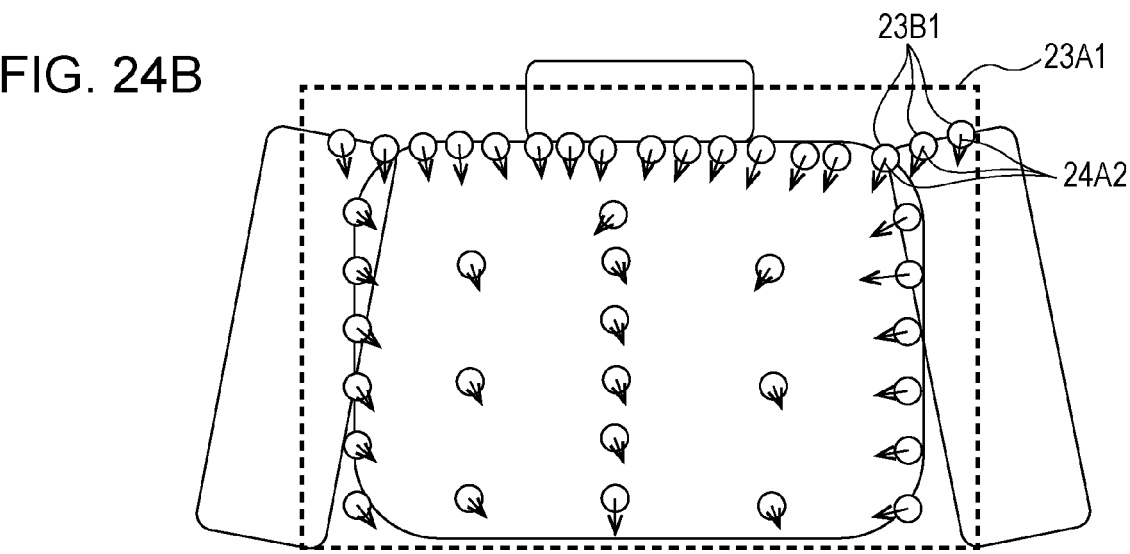
FIG. 24B is a second explanatory diagram for explaining calculation of a respiratory component in the non-contact blood-pressure measuring device according to Embodiment 2.
Figure 24C:
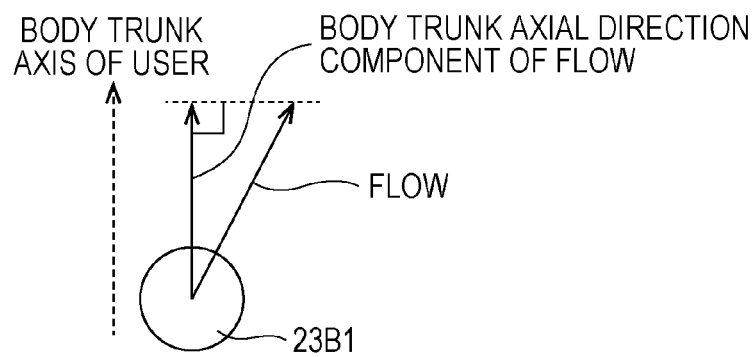
FIG. 24C is a third explanatory diagram for explaining calculation of a respiratory component in the non-contact blood-pressure measuring device according to Embodiment 2.

FIGS. 24A, 24B, and 24C are explanatory diagrams for explaining calculation of a respiratory component in the non-contact blood-pressure measuring device according to the present embodiment. Specifically, FIGS. 24A and 24B are enlarged views of the chest region 23A1 illustrated in FIG. 23B and obtained feature points 23B1 and illustrate a relation between breathing and the optical flows.

When a user breathes, the feature points move in a predetermined direction and with a predetermined magnitude in accordance with breathing. FIG. 24A illustrates movement (flows) 24A1 of the feature points 23B1 during inhalation of the user. In accordance with the user's inhalation, feature points in the vicinity of the shoulder move upward, and feature points in the vicinity of the chest move in a direction in which the chest expands.

FIG. 24B illustrates flows 24A2 of the feature points 23B1 during user's exhalation. As is clear from FIG. 24B, in accordance with the user's exhalation, the feature points in the vicinity of the shoulder move downward, and the feature points in the vicinity of the chest move in a direction in which the chest contracts.

For example, the total sum of body trunk axial direction components of the flows (movement vectors) of the feature points (cosine components of the flows (an upward direction is a positive direction, and a downward direction is a negative direction)) are calculated as a respiratory component. Use of the body trunk axial direction components makes it possible to remove body movement and noise components that are irrelevant with breathing. It is therefore possible to accurately extract movement caused by breathing.

Figure 25:
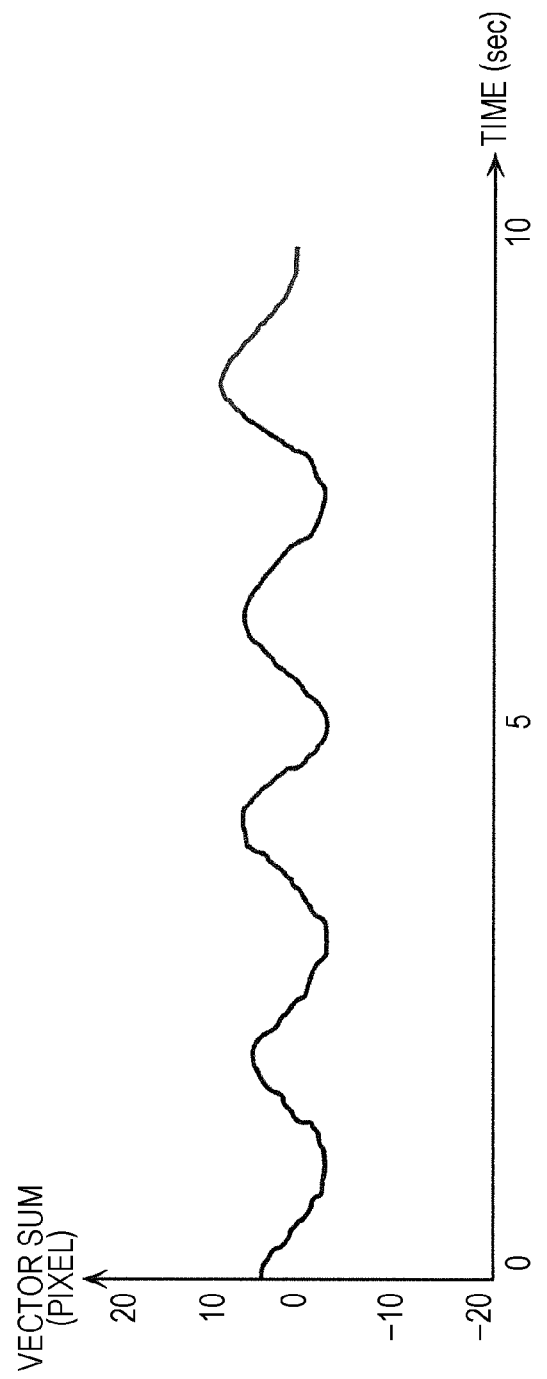
FIG. 25 is an explanatory diagram of a respiratory component calculated by the non-contact blood-pressure measuring device according to Embodiment 2.

FIG. 25 is an explanatory diagram for explaining a respiratory component calculated by the non-contact blood-pressure measuring device according to the present embodiment. Specifically, FIG. 25 is a graph showing the total sum of magnitudes of the flows of the feature points that have been subjected to low-pass filtering to remove noise. As is clear from FIG. 25, periodicity corresponding to breathing is obtained.

As in Embodiment 1, a heartbeat timing calculating section 104 calculates a heartbeat timing on the basis of a reception signal detected by a millimeter-wave acquiring section 103. Furthermore, in the present embodiment, the heartbeat timing calculating section 104 calculates a heartbeat timing by removing the influence of breathing by using the respiratory component calculated by the respiratory component calculating section 111.

In a case where the user is deeply breathing, movement of the chest caused by breathing is also detected in a signal of a millimeter wave that is reflected by the chest of the user and is then detected by the millimeter-wave acquiring section 103.

Figure 26:
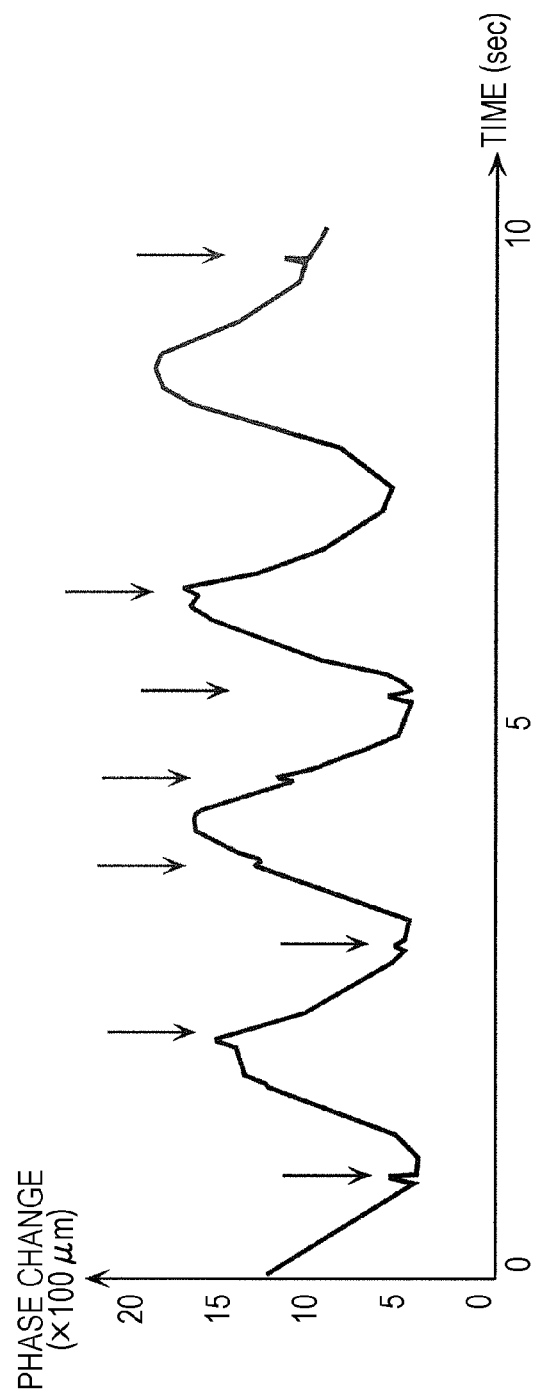
FIG. 26 is a first explanatory diagram for explaining calculation of a pulse-wave timing in the non-contact blood-pressure measuring device according to Embodiment 2.

FIG. 26 is a first explanatory diagram for explaining calculation of a pulse-wave timing in the non-contact blood-pressure measuring device according to the present embodiment. Specifically, FIG. 26 illustrates a millimeter wave signal during breathing. FIG. 26 is a graph showing a millimeter wave reception signal that is obtained while a user is deeply breathing in a constant cycle for approximately 10 seconds and that has been subjected to low-pass filtering. In FIG. 26, the horizontal axis represents a time (sec), and the vertical axis represents a phase change (100 µm). As is clear from FIG. 26, a periodical signal is obtained due to breathing.

Experiments conducted by the inventors of the present invention revealed that the amplitude caused by breathing is approximately 1 mm to 3 mm. Meanwhile, a change caused by a heartbeat is approximately 0.1 mm to 0.2 mm. Therefore, a heartbeat is sometimes buried in breathing, or it is sometimes difficult to obtain a peak of a heartbeat. In FIG. 26, small peaks indicated by the arrows are phase changes caused by heartbeats but are smaller than peaks caused by breathing as illustrated in FIG. 26. Furthermore, as is clear from FIG. 26, the peaks caused by heartbeats are buried or very small during inhalation and exhalation.

In view of this, in the present embodiment, a heartbeat timing is calculated by using a respiratory signal obtained by the respiratory component calculating section 111.

For example, a heartbeat timing is calculated by using a timing less affected by breathing, such as a predetermined period around the end of inhalation (a peak part of the periodic signal) or a predetermined period around the end of exhalation (a bottom part of the periodic signal). In the following description, an example in which the predetermined interval around the end of inhalation (a peak part of the periodic signal) is used is described.

Figure 27:
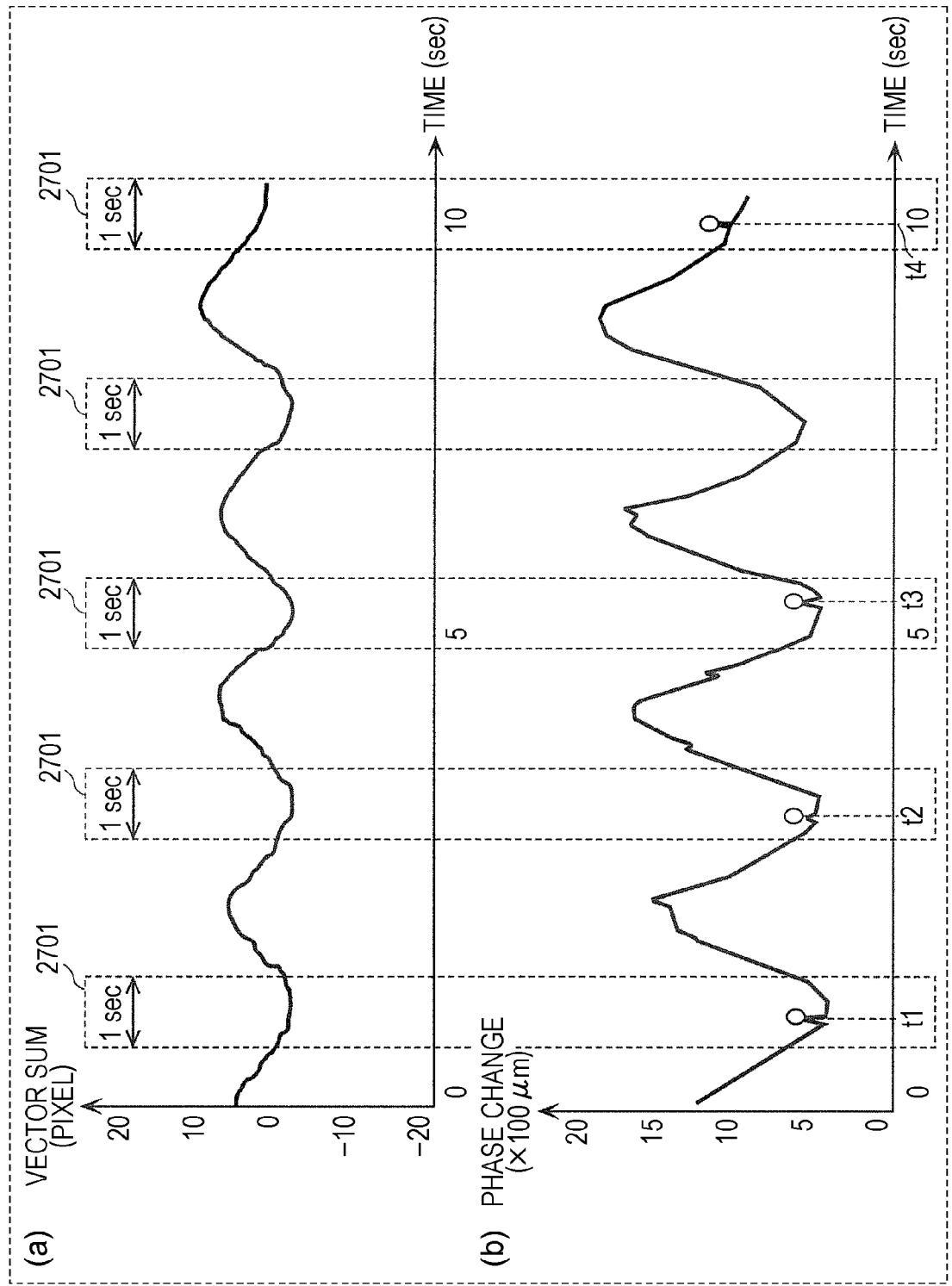
FIG. 27 is a second explanatory diagram for explaining calculation of a pulse-wave timing in the non-contact blood-pressure measuring device according to Embodiment 2.

FIG. 27 is a second explanatory diagram for explaining calculation of a pulse-wave timing in the non-contact blood-pressure measuring device according to the present embodiment. Specifically, FIG. 27 is a diagram for explaining calculation of a heartbeat timing. (a) of FIG. 27 illustrates a respiratory component obtained by the respiratory component calculating section 111 as in FIG. 25. (b) of FIG. 27 illustrates a signal detected by the millimeter-wave acquiring section 103 as in FIG. 26. In FIG. 27, the horizontal axis represents a time, and temporal synchronization is achieved between the moving image captured by the image acquiring section 101 and the millimeter wave detected by the millimeter-wave acquiring section 103. Since (a) and (b) of FIG. 27 illustrates states of the same user sensed during breathing, respiratory components are in synchronization with each other.

First, a bottom and a predetermined interval are specified from the periodic signal of the respiratory component obtained by the respiratory component calculating section 111 illustrated in (a) of FIG. 27. For example, the bottom is specified by a peak search method, and an interval of ±0.5 seconds from the bottom (1 second in total) is determined as the predetermined interval. This is because the rate of heartbeat is generally 80 bpm and it is therefore highly likely that at least one heartbeat is included in 1 second and because movement of the chest is smaller in the predetermined interval around the end of exhalation and the predetermined interval around the end of inhalation than during inhalation or exhalation, and therefore changes caused by heartbeats are easier to be detected as peaks in these predetermined intervals.

Note that a method for specifying the interval is not limited to this and can be frequency analysis or a correlation method. Since breathing is routinely performed in a relatively periodical manner, peak and bottom intervals can be efficiently specified. Furthermore, an interval with little amplitude fluctuation may be specified by trend extraction. This makes it possible to specify an interval with little respiratory fluctuation even in a case where the periodic signal has a relatively large fluctuation.

Next, a heartbeat timing is detected within the interval by using a signal detected by the millimeter-wave acquiring section 103. In a case where a heartbeat occurs around the end of exhalation or during a period in which the major trend of the signal is a bottom, the chest slightly moves accordingly, and as a result, a peak of the heartbeat sometimes appears. For example, as in Embodiment 1, a heartbeat timing is calculated by a peak search method. For example, t1, t2, t3, and t4 in (b) of FIG. 27 are obtained heartbeat timings.

Calculation of a heartbeat timing in the present embodiment has been described above. Processing for determining blood pressure by using a time difference between the obtained heartbeat timing and the pulse-wave timing obtained on the basis of a change of luminance in the image by the pulse-wave timing calculating section 102 is similar to that in Embodiment 1. That is, blood pressure is determined by the blood-pressure determining section 105 and is then presented on the presenting section 106.

An operation flow according to the present embodiment is described below with reference to FIGS. 28, 29, and 30. The overall flow is similar to that in Embodiment 1, and similar steps are given identical reference signs.

Figure 28:
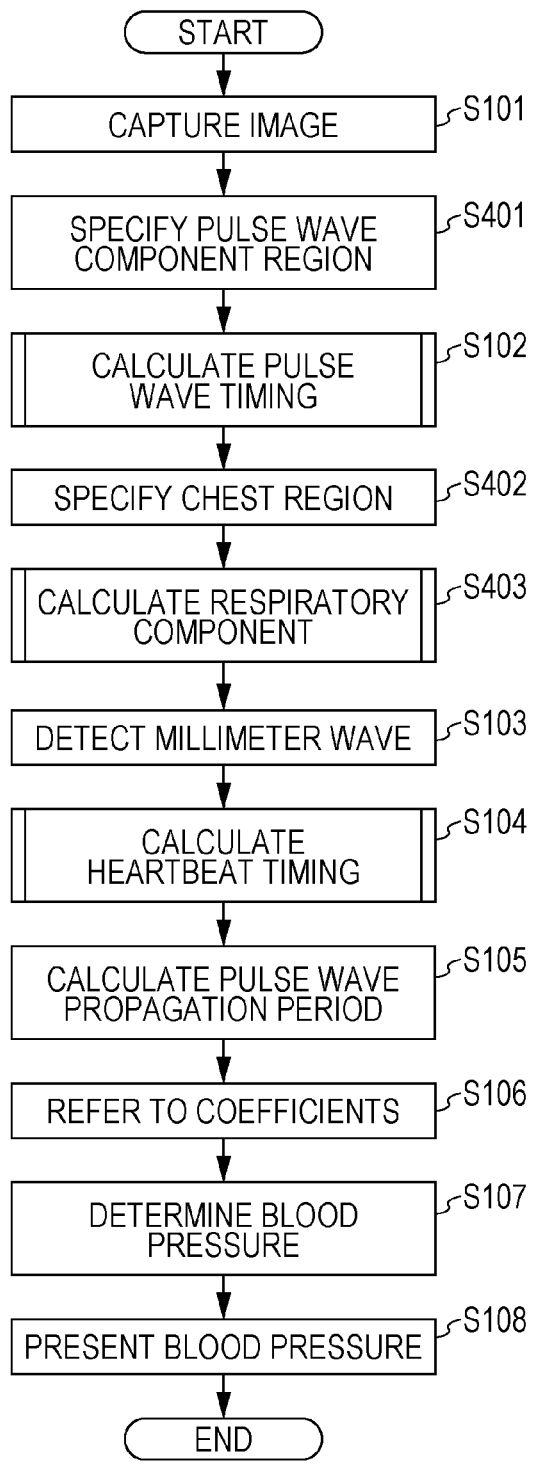
FIG. 28 is a flow chart illustrating flow of blood pressure measuring processing in the non-contact blood-pressure measuring device according to Embodiment 2.

FIG. 28 is a flow chart illustrating a flow of blood pressure measuring processing in the non-contact blood-pressure measuring device according to the present embodiment. In this flow chart, a step of specifying a region in which a pulse wave component is extracted (Step S401), a step of specifying a chest region (Step S402), and a step of calculating a respiratory component (Step S403) are added in addition to the steps of the flow chart of FIG. 11.

First, the image acquiring section 101 captures, as a skin image, an image of a face (Step S101).

Next, the pulse wave component region specifying section 108 specifies a region (for example, a region such as a cheek) in which a pulse wave is extracted (Step S401).

Next, the pulse-wave timing calculating section 102 calculates a pulse-wave timing on the basis of a change of the luminance within the region specified in Step S401 (Step S102). Details of the flow are similar to those in FIG. 12, and description thereof is omitted.

Next (or in parallel with the step of specifying the pulse wave region), the chest region specifying section 109 specifies a chest region (Step S402). Then, the respiratory component calculating section 111 calculates a respiratory component (Step S403).

Figure 29:
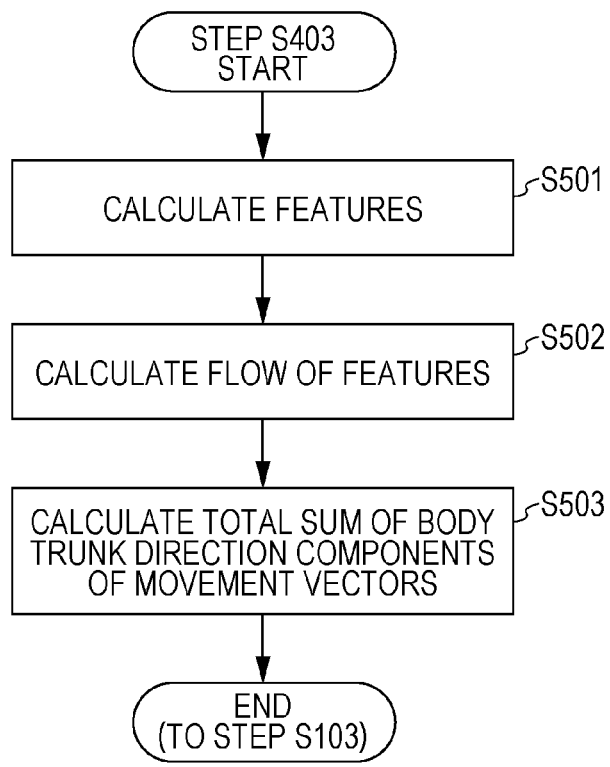
FIG. 29 is a first flow chart illustrating flow of details of the blood pressure measuring processing in the non-contact blood-pressure measuring device according to Embodiment 2.

FIG. 29 is a flow illustrating the details of Step S403.

First, the respiratory component calculating section 111 calculates feature points (Step S501). For example, the respiratory component calculating section 111 calculates feature points along a boundary line between the person and the background and a shoulder line (because corresponding points can be easily obtained).

Next, the respiratory component calculating section 111 calculates flows (movement vectors) of the feature points that are obtained in accordance with body movement of the user (Step S502).

Next, the respiratory component calculating section 111 calculates the total sum of body trunk axial direction components of the movement vectors (Step S503). A periodic signal thus obtained is a signal based on breathing.

See FIG. 28 again. Next, the millimeter-wave acquiring section 103 detects a millimeter wave (Step S103).

The heartbeat timing calculating section 104 calculates a heartbeat timing on the basis of a phase change of the detected millimeter wave (Step S104).

Figure 30:
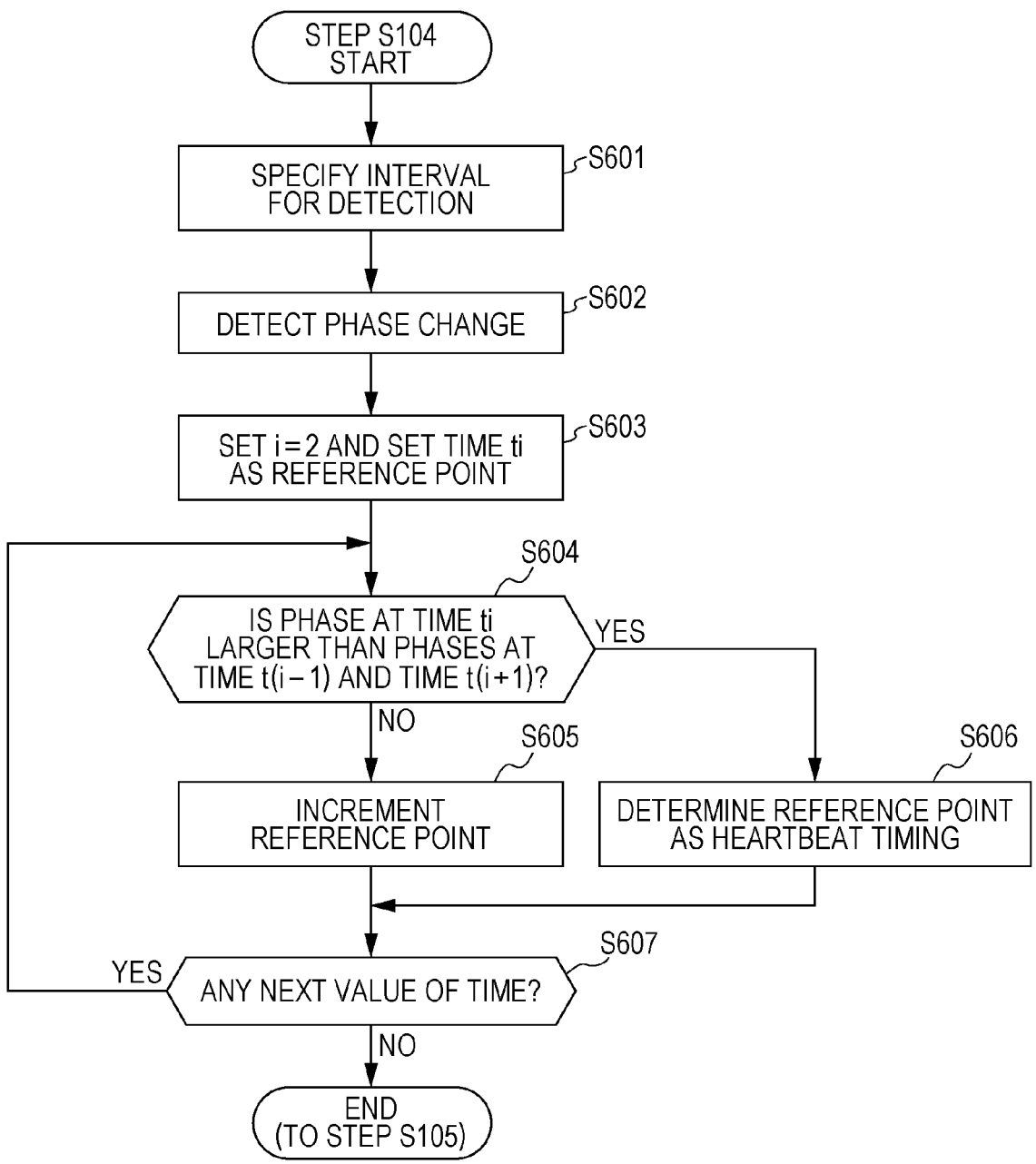
FIG. 30 is a second flow chart illustrating flow of details of the blood pressure measuring processing in the non-contact blood-pressure measuring device according to Embodiment 2.

FIG. 30 is a flow chart illustrating the details of Step S104.

First, the heartbeat timing calculating section 104 specifies a bottom interval of the periodic signal, which is, for example, an interval around the end of exhalation, on the basis of the respiratory component obtained by the respiratory component calculating section 111 (Step S601). In the present embodiment, a heartbeat timing is calculated within this interval by a method such as a peak search method.

Next, the heartbeat timing calculating section 104 calculates a phase change of a wave reflected from the chest (Step S602).

Then, the heartbeat timing calculating section 104 calculates a heartbeat timing within the interval by a method such as a peak search method. Specifically, the heartbeat timing calculating section 104 sets i=2 and sets a time ti (i.e., time t2) as a reference point (Step S603).

The heartbeat timing calculating section 104 performs a comparison operation of comparing a phase of the millimeter wave at the time ti with a phase of the millimeter wave at a time t (i−1), which is one time point earlier than the reference point set in Step S603, and with a phase of the millimeter wave at a time t (i+1), which is one time point later than the reference point set in Step S603 (Step S604).

In a case where it is determined in Step S604 that the phase of the millimeter wave at the time ti is larger than both of the phase of the millimeter wave at the time t (i−1) and the phase of the millimeter wave at the time t (i+1) (Yes in Step S604), it is determined that the reference point is a local peak, and the reference point is specified as a heartbeat timing (Step S606).

Meanwhile, in a case where it is determined in Step S604 that the phase of the millimeter wave at the time ti is smaller than any of the phase of the millimeter wave at the time t (i−1) and the phase of the millimeter wave at the time t (i+1) (No in Step S604), an index i indicative of the reference point is incremented (Step S607). Then, a phase of the millimeter wave at the incremented reference point is compared with a phase of the millimeter wave at a time which is one time point earlier than the reference point and a phase of the millimeter wave at a time which is one time point later than the reference point (return to Step S604).

After the end of the interval, peak search is performed in a similar manner in a next interval, and in a case where a final point of the signal is reached (Yes in Step S307), the processing returns to the main flow (to Step S105).

See FIG. 28 again. The blood-pressure determining section 105 calculates a time difference (pulse wave propagation period) between the pulse-wave timing calculated by the pulse-wave timing calculating section 102 and the heartbeat timing calculated by the heartbeat timing calculating section 104 (Step S105).

The blood-pressure determining section 105 refers to parameters (coefficients α and β) in models accumulated in the model accumulating section 107 (Step S106) and determines blood pressure (Step S107).

The presenting section 106 presents the determined blood pressure (Step S108).

In the above description, a case where the optical flow feature points are arbitrary points within the chest region has been described. However, the present embodiment is not limited to this. For example, it is possible to employ an arrangement in which edges are extracted from an image by a method such as Canny edge detection, a shoulder line is extracted on the basis of a difference between a person and the background by a method such as Hough conversion, and then feature points are extracted on the shoulder line.

Figure 31A:
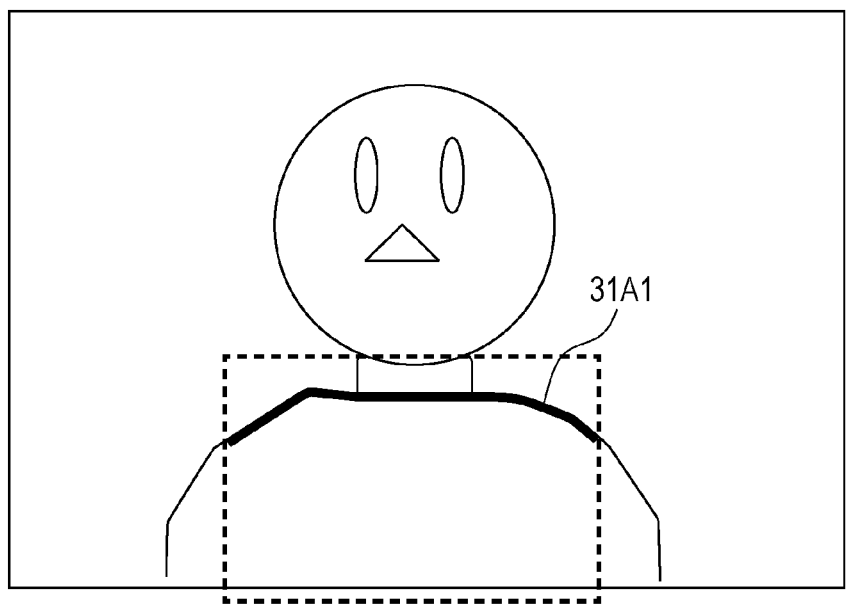
FIG. 31A is a first explanatory diagram for explaining processing for specifying a shoulder region in the non-contact blood-pressure measuring device according to Embodiment 2.
Figure 31B:
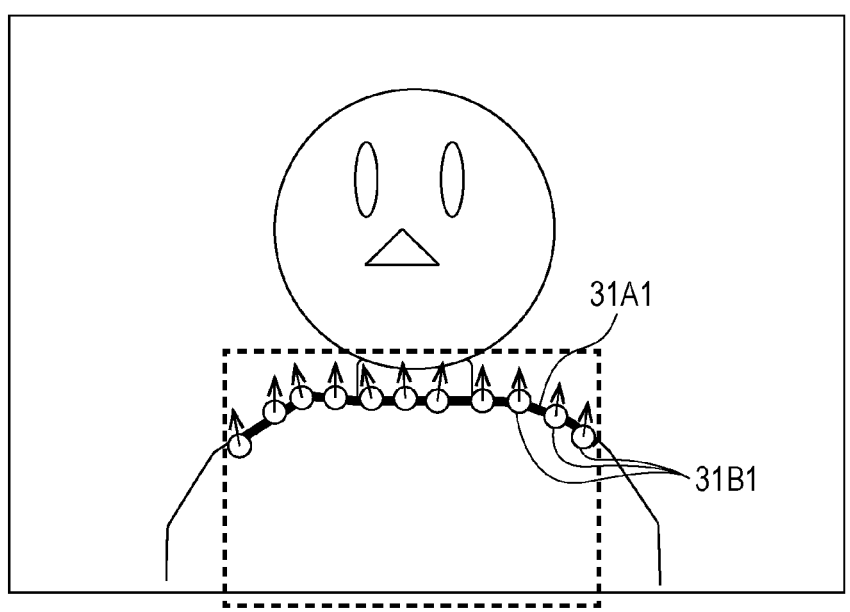
FIG. 31B is a second explanatory diagram for explaining processing for specifying a shoulder region in the non-contact blood-pressure measuring device according to Embodiment 2.

FIGS. 31A and 31B are explanatory diagrams for explaining processing for specifying a shoulder region in the non-contact blood-pressure measuring device according to the present embodiment. In FIG. 31A, a shoulder line 31A1 of the user is extracted as a bold line by edge extraction. FIG. 31B illustrates feature points 31B1 obtained on the line 31A1. The total sum of upward and downward movement vectors of the feature points 31B1 is regarded as a respiratory component.

When a person breathes, especially a shoulder line slightly moves upward and downward in accordance with breathing. In view of this, feature points are calculated on the shoulder line and in the vicinity of the shoulder line, and movement vectors of these feature points are used as a respiratory component. This makes it possible to remove the influence of movement that is irrelevant with breathing (for example, sideways movement or movement in a depth direction), thereby making it possible to accurately calculate a respiratory component.

In the above description, a case where an interval less influenced by breathing is specified, and a heartbeat timing is calculated within the specified interval on the basis of a millimeter wave signal has been described. However, the present embodiment is not limited to this. Since the amplitude (1 mm to 3 mm) and the cycle (several tens of times per minute at most) of breathing are largely different from the amplitude (0.1 mm to 0.3 mm) and the cycle (for example, 80 bpm) of a heartbeat, a heartbeat timing may be calculated by using these pieces of information. For example, since the peak width of a heartbeat is approximately 0.5 seconds to 1 second, a more robust heartbeat timing calculation is possible by using information on the peak width in peak search.

Furthermore, for example, a heartbeat timing may be calculated after a respiratory component is removed by an adaptive filter such as LMS (Least Mean Square). It can be considered that a signal of a respiratory component from the chest that is obtained on the basis of an image is mainly a signal of breathing and contains almost no subtle signal of a heartbeat (excluding other noise signals). For example, in a case where a user is wearing a cloth, there is almost no possibility that the cloth moves due to a beat of the heart and the movement of the cloth appears as a signal in an image. Even in a case where the user is not wearing a cloth or even in a case where a skin region is used, movement caused by a beat of the heart is not generally detected on the basis of information obtained from the resolution of an image as compared with the resolution of a millimeter wave. Meanwhile, a signal of a millimeter wave contains both a respiratory component and a heartbeat component. Since a millimeter wave penetrates a cloth and is capable of detecting slight movement on an actual chest surface, the millimeter wave contains both a respiratory component and a heartbeat component. That is, the same phenomenon of breathing is detected by different sensor media, i.e., an image and a millimeter wave at the same timing.

In view of this, an adaptive filter is applied while using one of the sensor media (for example, the millimeter wave) as an input and using the other one of the sensor media (for example, the image) as reference data. This removes the same component (respiratory component), and the heartbeat component which exists only in the one of the sensor media (the millimeter wave) remains. A heartbeat timing may be calculated on the basis of a signal thus obtained by the adaptive filter.

It is also possible to employ an arrangement in which a frequency is calculated from a respiratory component obtained on the basis of an image, a notch filter for removing the frequency is applied to a millimeter wave signal, and a heartbeat timing is calculated from a signal thus obtained.

Under a routine environment, a signal obtained from a millimeter wave contains both a respiratory component and a heartbeat component. By obtaining a signal mainly containing only a respiratory component or frequency information from an image, it is possible to remove the influence of breathing and to accurately calculate a heartbeat timing on the basis of the signal from which the influence of breathing has been removed.

Information concerning a timing of breathing may be presented on the presenting section 106 so as to prompt a user to breathe in a predetermined manner.

Figure 32A:
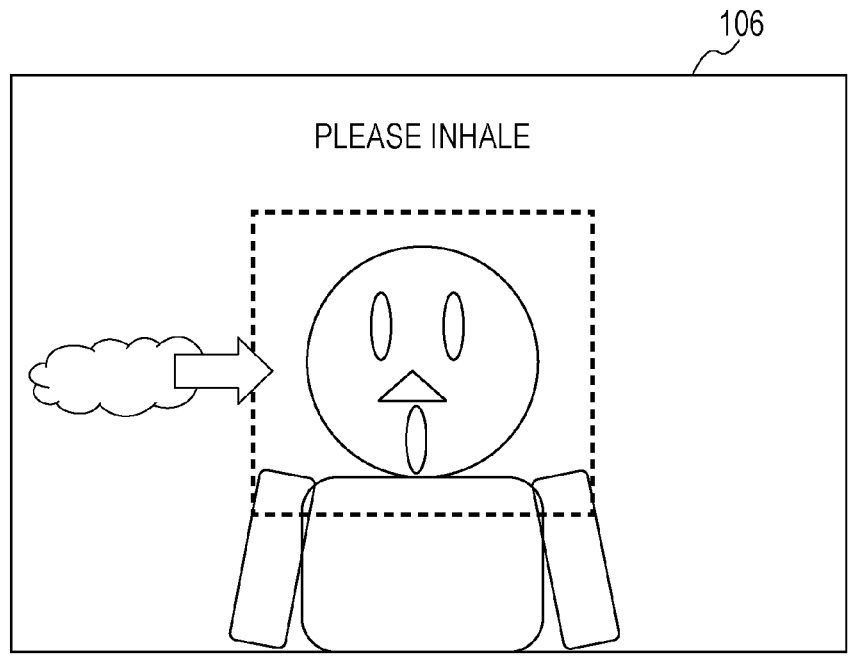
FIG. 32A is an explanatory diagram of first presentation prompting a timing of breathing in the non-contact blood-pressure measuring device according to Embodiment 2.
Figure 32B:
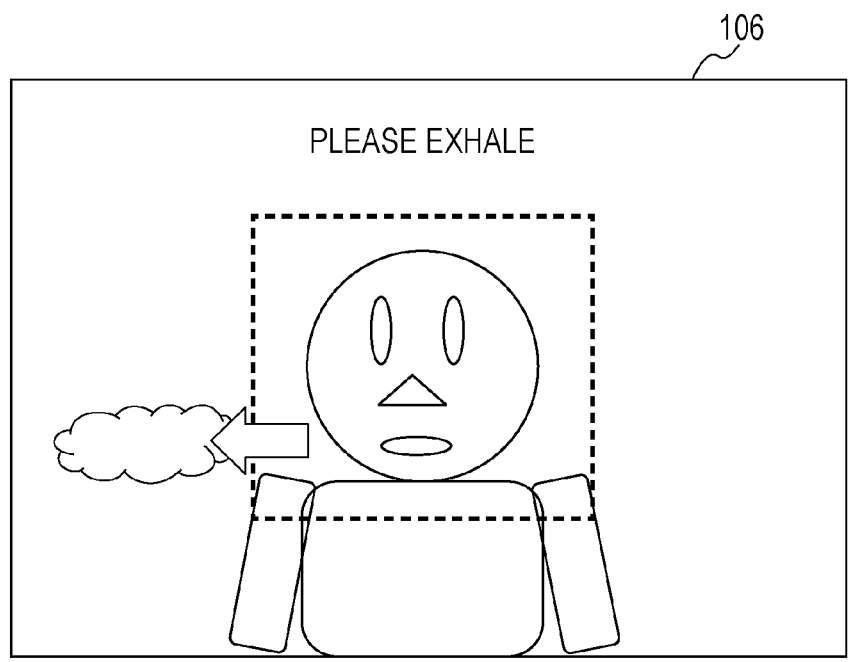
FIG. 32B is an explanatory diagram of second presentation prompting a timing of breathing in the non-contact blood-pressure measuring device according to Embodiment 2.

FIGS. 32A and 32B are explanatory diagrams for explaining first presentation prompting a user to breathe at a designated timing in the non-contact blood-pressure measuring device according to the present embodiment.

In FIG. 32A, a message "PLEASE INHALE" is presented. In FIG. 32B, a message "PLEASE EXHALE" is presented. Measurement of blood pressure is performed in a manner such that a user breathes at a presented timing while watching such a message. Meanwhile, the heartbeat timing calculating section 104 calculates a heartbeat timing by using an interval less affected by breathing such as an interval around the end of inhalation or an interval around the end of exhalation assuming that a signal according to the presented timing of breathing, which is known, is detected.

Note that the presenting section 106 may further present a message such as "PLEASE HOLD YOUR BREATH FOR THREE SECONDS" so as to prompt the user to hold his or her breath for a predetermined interval. By thus prompting the user to breathe in a manner suitable for calculation of a heartbeat timing, it is possible to more accurately calculate a heartbeat timing.

In general, the pulse rate is 60 to 70 beats at rest, and therefore a pulse wave propagation time can be measured at the rate of one time in approximately 1 second. That is, in an ideal state, blood pressure can be successively measured every second. This allows the user to check how blood pressure changes depending on a breathing state. Furthermore, the user can visually check how much the blood pressure improves due to deep breathing or the like. That is, the non-contact blood-pressure measuring device has advantages of being capable of completing one measurement in a short period of time and being capable of measuring a transition of blood pressure by successively performing measurement plural times.

Processing in Imaginary Space of Millimeter Wave

In the millimeter-wave signal processing in Embodiment 1, a heartbeat component is obtained on the basis of a phase change. However, a method for obtaining a heartbeat component is not limited to this. An accurate heartbeat component with a higher SN ratio may be obtained by adding the following signal processing.

FIG. 26 illustrates a heartbeat component during breathing, which represents the distance obtained by the expression (5).

Figure 33A:
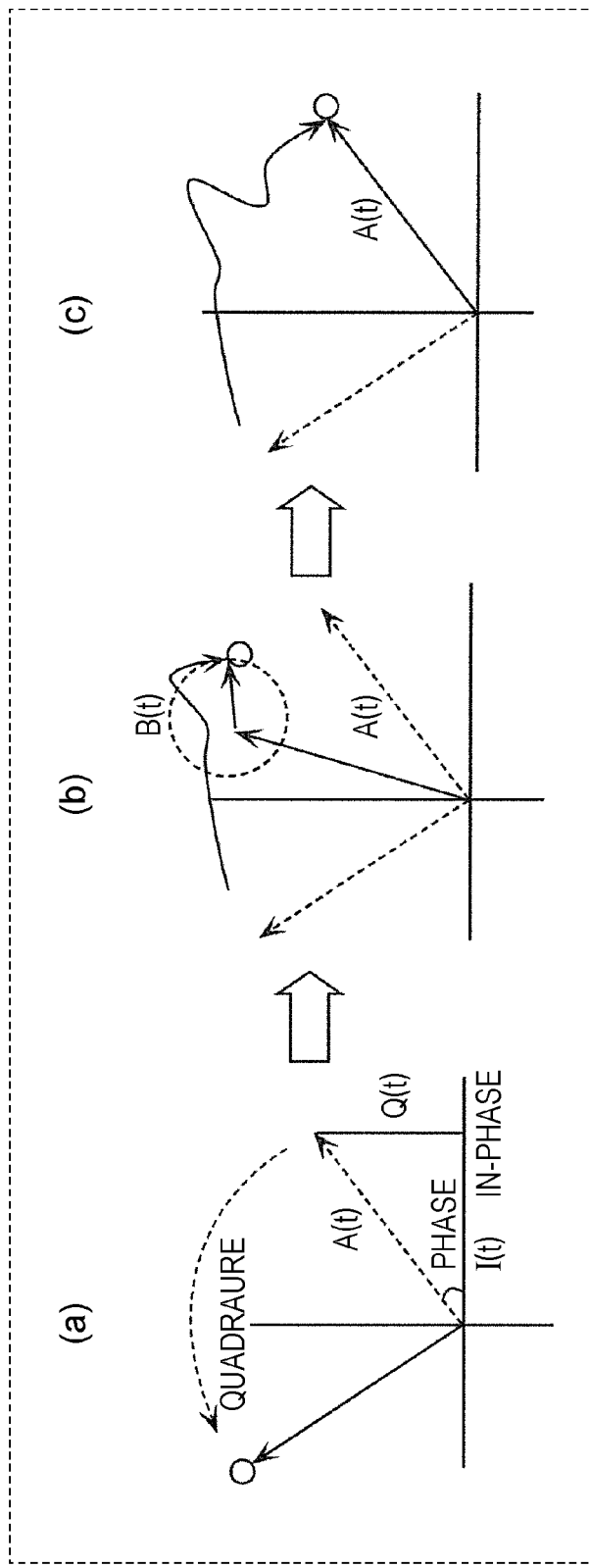
FIG. 33A is a first schematic view illustrating a temporal change of a heartbeat on a complex plane in Embodiment 2.

FIG. 33A is a first schematic view illustrating a temporal change of a heartbeat on a complex plane in the present embodiment. FIG. 33A is a schematic view modeling movement of a heartbeat during breathing on a complex plane before conversion into the distance.

The amplitude A(t) of a reflected wave depends on the strength, size, or shape of a reflection surface. In a case where the reflected wave is a wave reflected by the chest of a person, it can be considered that the magnitude of A(t) is almost constant and hardly changes in accordance with breathing. Accordingly, the vector exhibits a predetermined rotary action (moves back and forth in an arc) on the complex plane while keeping the amplitude A almost constant ((a) of FIG. 33A). Meanwhile, a change that occurs due to contraction or expansion of the heart is smaller and more instantaneous than a change that occurs due to breathing, and appears, for example, as indicated by B (t) in (b) of FIG. 33A. A signal is obtained as a vector in which these are added together. Then, the vector exhibits movement based on breathing ((c) of FIG. 33A) again. That is, a body movement signal of breathing and a heartbeat can be considered a model in which a relatively steady rotary vector and an instantaneous vector are added together.

In view of this, for example, a more robust heartbeat component may be obtained by calculating a respiratory component from an in-plane component and a quadrature component in a predetermined interval and then suppressing the calculated respiratory component so as to emphasize an instantaneous heartbeat. For example, a vector suppressing a respiratory component can be obtained by multiplying, by a weight coefficient α, a vector length A' obtained by averaging previous and subsequent predetermined values (n) (expression (8)) and then subtracting the obtained value from an original vector (expression (7)).

$$A'(t)=A(t)-f(n,\alpha) \quad (7)$$

$$f(n,\alpha)=\alpha\Sigma_{k=t-n/2}^{k=t+n/2}A(k)/n \quad (8)$$

Figure 33B:
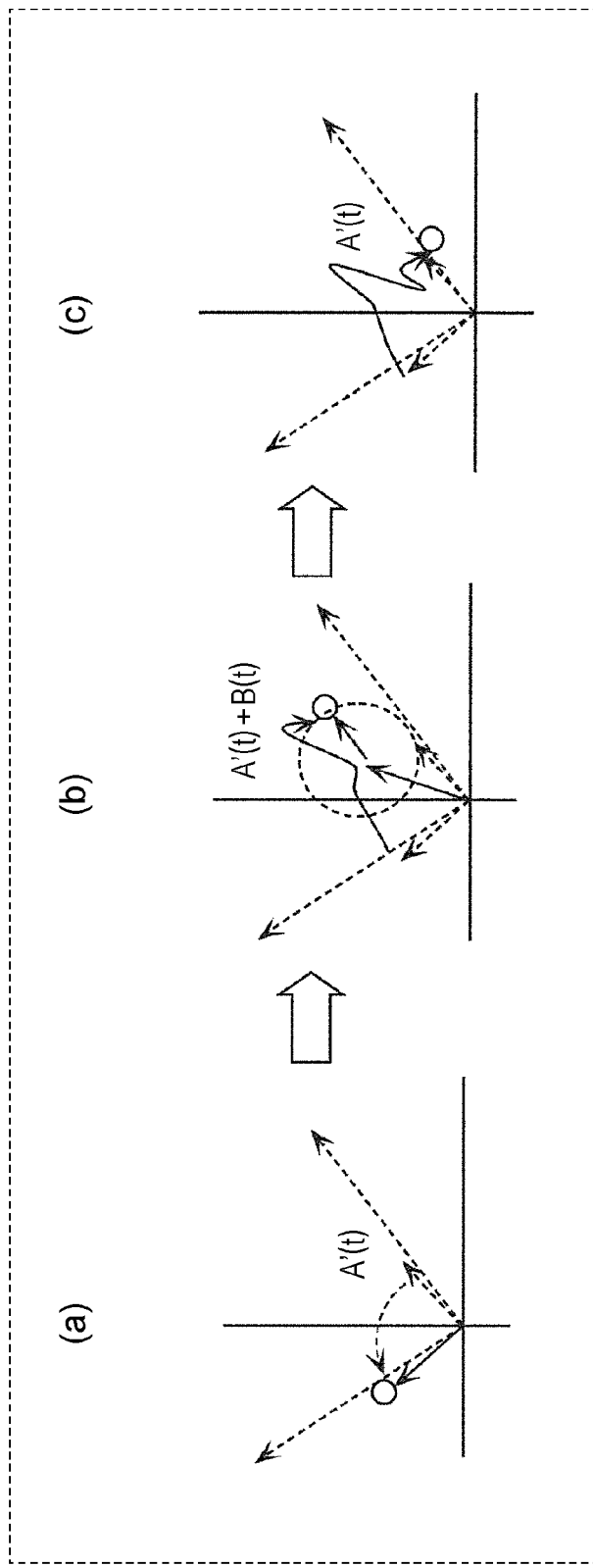
FIG. 33B is a second schematic view illustrating a temporal change of a heartbeat on a complex plane in Embodiment 2.
Figure 34:
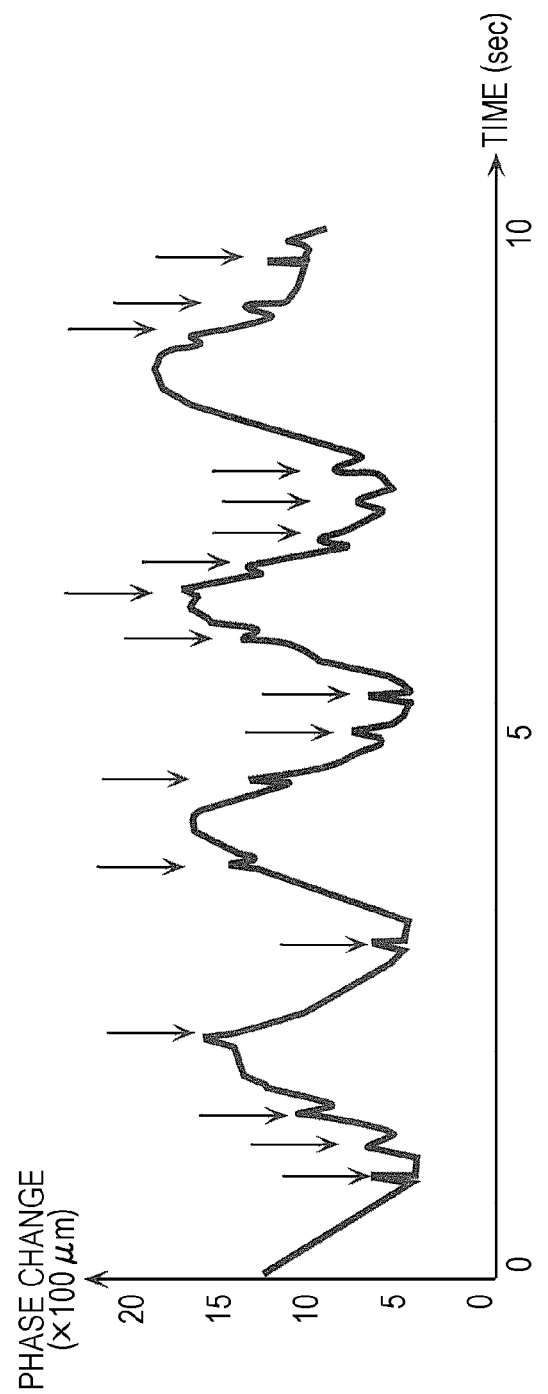
FIG. 34 is a third explanatory diagram for explaining calculation of a pulse-wave timing in the non-contact blood-pressure measuring device according to Embodiment 2.
Figure 35:
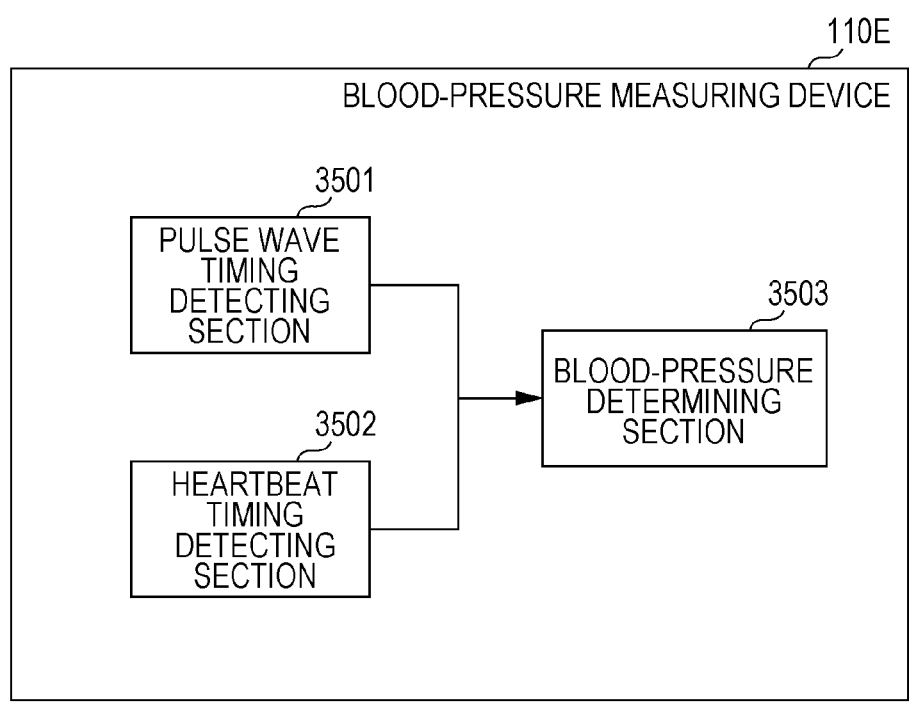
FIG. 35 is a block diagram illustrating a modification of the non-contact blood-pressure measuring devices of the embodiments.

(a) of FIG. 33B is a diagram illustrating vector movement in a case where a respiratory component is suppressed. In (a) of FIG. 33B, A' with a shorter vector length than in (a) of FIG. 33A exhibits a rotary action due to breathing. When a heartbeat occurs, a vector B instantaneously appears ((b) of FIG. 33B). FIG. 34 is a graph after conversion into a distance obtained by calculating a phase from the vector on the complex plane thus obtained.

FIG. 34 is a third explanatory diagram for explaining calculation of a pulse-wave timing in the non-contact blood-pressure measuring device according to the present embodiment.

Since both breathing and a phase change are emphasized on the complex vector plane, a signal in which a heartbeat component is more emphasized than in FIG. 26 is obtained in FIG. 34. Note that techniques other than the aforementioned technique may be used. For example, a vector change caused by breathing may be obtained by using an interval at the time of inhalation or by using a predetermined interval immediately after a large heartbeat is obtained (it can be considered that there is no heartbeat component during this predetermined interval). Alternatively, it is possible to remove a steady component caused by reflection noise and obtain and shift the center of a circle.

Modifications of Embodiments

The non-contact blood-pressure measuring devices according to the above embodiments can be also expressed as follows.

That is, a non-contact blood-pressure measuring device 110E includes a pulse-wave timing detecting section 3501 that detects, as a pulse-wave timing, time information indicative of a time at which time-varying luminance in a skin image of user's skin reaches a peak, a heartbeat timing detecting section 3502 that detects, as a heartbeat timing, time information indicative of a time at which a time-varying distance to the user obtained on the basis of a signal of a radio wave reflected by the user reaches a peak, and a blood-pressure determining section 3503 that determines the blood pressure of the user on the basis of a time difference between the pulse-wave timing and the heartbeat timing.

This produces effects similar to those produced by the non-contact blood-pressure measuring devices of the above embodiments.

In the present disclosure, the computer program or the digital signal may be transmitted via a network or the like represented by an electric communication line, a wireless or wired communication line, and the Internet.

The present disclosure may be a computer system including a microprocessor and a memory, the memory storing the computer program, and the microprocessor operating in accordance with the computer program.

The program or the digital signal may be executed in another independent computer system by transferring the program or the digital signal on the recording medium or by transferring the program or the digital signal via the network or the like.

In the above embodiments, each of the constituent elements may be realized by dedicated hardware or may be realized by execution of a software program suitable for the constituent element. Each of the constituent elements may be realized in a manner such that a program executing section such as a CPU or a processor reads out and executes a software program recorded on a recording medium such as a hard disc or a semiconductor memory. Software realizing the non-contact blood-pressure measuring devices and the like of the above embodiments is the following program.

Specifically, this program causes a computer to execute a non-contact blood-pressure measuring method including an image acquiring step of acquiring a skin image obtained by capturing skin of a user, a pulse-wave timing calculating step of calculating, as a pulse-wave timing, time information indicative of a time at which time-varying luminance in the skin image reaches a peak, a radio wave acquiring step of acquiring a signal of a radio wave reflected by the user, a heartbeat timing calculating step of calculating, as a heartbeat timing, time information indicative of a time at which a time-varying distance to the user obtained on the basis the signal of the radio wave acquired in the radio wave acquiring step reaches a peak, and a blood pressure determining step of determining the blood pressure of the user on the basis of a time difference between the pulse-wave timing and the heartbeat timing.

Furthermore, the above embodiments and modifications may be combined.

In the present disclosure, one or more of the units and devices or one or more of the functional blocks in the block diagram may be realized by one or more electronic circuits including a semiconductor device, a semiconductor integrated circuit (IC), or an LSI (large scale integration). The LSI or the IC may be realized as a single chip or may be realized as a combination of a plurality of chips. For example, functional blocks other than a storage element may be integrated in a single chip. Although the terms "LSI" and "IC" are used, the term varies depending on the degree of integration, and terms "system LSI", "VLSI (very large scale integration)", or "ULSI (ultra large scale integration)" may be used. A Field Programmable Gate Array (FPGA), which can be programmed after production of an LSI, or a reconfigurable logic device, in which reconfiguration of a junction relation in an LSI or set-up of a circuit section in an LSI is possible, can also be used for the same purpose.

Furthermore, one or more of functions or operations of the units, devices, or one or more of the devices can be executed by software processing. In this case, the software is recorded on one or more non-transitory recording media such as a ROM, an optical disc, or a hard disc drive, and in a case where the software is executed by a processing device (processor), the software causes the processing device (processor) and peripheral devices to execute specific functions in the software. A system or a device may include one or more non-transitory recording media on which software is recorded, a processing device (processor), and a needed hardware device such as an interface.

The embodiments disclosed herein are merely illustrative examples and should not be construed as being restrictive in any way. The scope of the present disclosure is indicated not by the above description but by the scope of the claims, and is intended to encompass all modifications within the meaning and the scope equivalent to the scope of the claims.

The present disclosure is applicable especially to a non-contact blood-pressure measuring device and the like.

What is claimed is:

1. A non contact blood-pressure measuring device comprising:
   an image acquirer that acquires a skin image obtained by capturing skin of a user;
   a pulse-wave timing calculator that calculates a temporal change of luminance in the skin image by using the skin image and calculates, as a pulse-wave timing, time information indicative of a time at which the luminance reaches a peak;
   a radio wave acquirer that acquires a signal of a radio wave reflected by the user and received by a reception antenna;
   a heartbeat timing calculator that calculates a temporal change of a distance between the user and the reception antenna by using the signal of the radio wave acquired by the radio wave acquirer and calculates, as a heartbeat timing, time information indicative of a time at which the distance reaches a peak; and
   a blood-pressure determiner that determines blood pressure of the user on the basis of a time difference between the pulse-wave timing and the heartbeat timing.

2. The non-contact blood-pressure measuring device according to claim 1, wherein
   the heartbeat timing calculator calculates, as the heartbeat timing, the time information indicative of a time at which the distance reaches a peak within a predetermined time range before the pulse-wave timing calculated by the pulse-wave timing calculator.

3. The non-contact blood-pressure measuring device according to claim 1, further comprising a posture measurer that measures an amount of change of a posture of the user on the basis of the skin image acquired by the image acquirer, wherein
   the blood-pressure determiner determining the blood pressure on the basis of a time difference between the pulse-wave timing calculated on the basis of the skin image acquired by the image acquirer during a period in which the amount of change measured by the posture measurer is equal to or lower than a predetermined threshold value and the heartbeat timing calculated on the basis of the radio wave acquired by the radio wave acquirer during the period.

4. The non-contact blood-pressure measuring device according to claim 3, wherein
   the image acquirer acquires the skin image obtained by capturing a portion including the skin of the user and a chest of the user;
   the posture measurer measures, as the amount of change, an amount of movement of a skin portion of the skin image or an amount of movement of a chest portion of the skin image; and
   the blood-pressure determiner that determines the blood pressure on the basis of a time difference between the pulse-wave timing calculated on the basis of the skin image acquired by the image acquirer during a period in which the amount of movement of the skin portion or the chest portion measured by the posture measurer is equal to or lower than a predetermined threshold value and the heartbeat timing calculated on the basis of the radio wave acquired by the radio wave acquirer during the period.

5. The non-contact blood-pressure measuring device according to claim 3, wherein
   the image acquirer includes an acquirer for posture measurement that acquires an image obtained by capturing the user from a direction different from a direction in which the radio wave acquirer acquires a radio wave; and
   the posture measurer measures the amount of change on the basis of the image acquired by the acquirer for posture measurement.

6. The non-contact blood-pressure measuring device according to claim 1, wherein
the blood-pressure determiner determines the blood pressure on the basis the time difference between the pulse-wave timing calculated by the pulse-wave timing calculator and the heartbeat timing calculated by the heartbeat timing calculator by using a predetermined relational expression including a predetermined parameter and the time difference.

7. The non-contact blood-pressure measuring device according to claim 6, wherein
the non-contact blood-pressure measuring device further includes a cuff-type blood pressure measurer that measures the blood pressure of the user by using a cuff; and
the blood-pressure determiner determines the predetermined parameter included in the relational expression by using the blood pressure of the user measured by the cuff-type blood pressure measurer.

8. The non-contact blood-pressure measuring device according to claim 7, wherein
the pulse-wave timing calculator calculates a plurality of pulse-wave timings;
the heartbeat timing calculator calculates a plurality of heartbeat timings that correspond to the respective calculated pulse-wave timings; and
the blood-pressure determiner determines the predetermined parameter included in the relational expression on the basis of (i) a time difference determined on the basis of a pair of pulse-wave timing and heartbeat timing included in a period from a first timing at which maximum blood pressure is measured by the cuff-type blood pressure measurer to a second timing at which minimum blood pressure is measured by the cuff-type blood pressure measurer, (ii) a time difference determined on the basis of a pair of pulse-wave timing and heartbeat timing that is closest to the first timing, or (iii) a time difference determined on the basis of a pair of pulse-wave timing and heartbeat timing that is closest to the second timing, among pairs of pulse-wave timing and heartbeat timing that correspond to each other.

9. The non-contact blood-pressure measuring device according to claim 7, wherein
the skin image is a skin image obtained by capturing skin of a portion anterior to a portion at which the cuff-type blood pressure measurer is attached among portions of an arm of the user.

10. The non-contact blood-pressure measuring device according to claim 1, wherein
the pulse-wave timing calculator calculates a plurality of pulse-wave timings;
the heartbeat timing calculator calculates a plurality of heartbeat timings that correspond to the respective calculated pulse-wave timings; and
the blood-pressure determiner calculates a plurality of time differences on the basis of respective pairs of pulse-wave timing and heartbeat timing that correspond to each other and determines the blood pressure on the basis of a value obtained by performing statistical processing on the calculated plurality of time differences.

11. The non-contact blood-pressure measuring device according to claim 6, further comprising:
a model accumulator in which candidates of the predetermined parameter included in the relational expression are stored; and
an acceptor that accepts profile information including at least one of height, weight, age, and blood pressure of the user,
the blood-pressure determiner determining a candidate to be used to determine the blood pressure among the candidates stored in the model accumulator on the basis of the profile information accepted by the acceptor and determines the blood pressure by using the relational expression including the determined candidate.

12. The non-contact blood-pressure measuring device according to claim 1, further comprising a second presenter that presents information designating a position of a body of the user so that the body of the user is located at a position suitable for acquisition of the skin image by the image acquirer and for acquisition of the radio wave by the radio wave acquirer.

13. The non-contact blood-pressure measuring device according to claim 12, wherein
the second presenter further presents, to the user, instruction information instructing the user to stay still, to be at rest, to inhale, or to exhale when the image acquirer acquires the skin image and when the radio wave acquirers acquires the radio wave.

14. The non-contact blood-pressure measuring device according to claim 12, wherein
the second presenter further presents the skin image to the user instantaneously every time the skin image is acquired by the image acquirer.

15. The non-contact blood-pressure measuring device according to claim 1, further comprising:
a skin region specifier that specifies a skin region which is a predetermined skin portion in the skin image acquired by the image acquirer;
a chest region specifier that specifies a chest region which is a chest portion of the user in the skin image acquired by the image acquirer; and
a respiratory component calculator that calculates a respiratory component included in a time-varying movement vector of a feature point within the chest region specified by the chest region specifier,
the pulse-wave timing calculator calculating the pulse-wave timing on the basis of time-varying luminance in the skin region, and
the heartbeat timing calculator calculating the heartbeat timing on the basis of a time-varying distance to the user obtained on the basis of the signal of the radio wave acquired by the radio wave acquirer and the respiratory component calculated by the respiratory component calculator.

16. The non-contact blood-pressure measuring device according to claim 15, wherein
the heartbeat timing calculator calculates the heartbeat timing on the basis of a radio wave acquired by the radio wave acquirer during a predetermined period including a peak or a bottom of the respiratory component that periodically changes over passage of time.

17. The non-contact blood-pressure measuring device according to claim 15, wherein
the heartbeat timing calculator calculates a frequency of the respiratory component that periodically changes over passage of time and calculates the heartbeat timing by filtering a periodical change in a frequency band including the calculated frequency in the signal of the radio wave acquired by the radio wave acquirer.

18. The non-contact blood-pressure measuring device according to claim 15, wherein the heartbeat timing calculator calculates the heartbeat timing by performing adaptive filtering by using the respiratory component and the signal of the radio wave acquired by the radio wave acquirer.

19. The non-contact blood-pressure measuring device according to claim 15, wherein
the chest region specifier further specifies a shoulder line of the user included in the skin image, sets the feature point on the specified shoulder line, and calculates the respiratory component by using the set feature point.

20. A non-contact blood-pressure measuring method comprising:
   (a) acquiring a skin image obtained by capturing skin of a user;
   (b) calculating, as a pulse-wave timing, time information indicative of a time at which time-varying luminance in the skin image reaches a peak;
   (c) acquiring a signal of a radio wave reflected by the user;
   (d) calculating, as a heartbeat timing, time information indicative of a time at which a time-varying distance to the user obtained on the basis of the signal of the radio wave acquired in the (c) acquiring reaches a peak; and
   (e) determining blood pressure of the user on the basis of a time difference between the pulse-wave timing and the heartbeat timing,
   at least one of the (a) acquiring, the (b) calculating, the (c) acquiring, the (d) calculating, and the (e) determining being executed by a circuit.

* * * * *